(12) United States Patent
Wang et al.

(10) Patent No.: US 12,102,737 B2
(45) Date of Patent: *Oct. 1, 2024

(54) DRUG COATED BALLOON CATHETERS FOR NONVASCULAR STRICTURES

(71) Applicant: Urotronic, Inc., Plymouth, MN (US)

(72) Inventors: Lixiao Wang, Henderson, NV (US); Peter Barnett, Shakopee, MN (US)

(73) Assignee: Urotronic, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/214,131

(22) Filed: Jun. 26, 2023

(65) Prior Publication Data

US 2023/0347022 A1 Nov. 2, 2023

Related U.S. Application Data

(63) Continuation of application No. 18/097,690, filed on Jan. 17, 2023, now Pat. No. 11,730,864, which is a
(Continued)

(51) Int. Cl.
*A61L 29/16* (2006.01)
*A61K 31/337* (2006.01)
(Continued)

(52) U.S. Cl.
CPC ............ *A61L 29/16* (2013.01); *A61K 31/337* (2013.01); *A61K 31/439* (2013.01); *A61L 29/08* (2013.01);
(Continued)

(58) Field of Classification Search
None
See application file for complete search history.

(56) References Cited

U.S. PATENT DOCUMENTS

| | | |
|---|---|---|
| 1,686,437 A | 10/1928 | Thomas et al. |
| 5,171,299 A | 12/1992 | Heitzmann et al. |
| (Continued) | | |

FOREIGN PATENT DOCUMENTS

| | | |
|---|---|---|
| CN | 101273926 A | 10/2008 |
| CN | 101610798 A | 12/2009 |
| (Continued) | | |

OTHER PUBLICATIONS

Jun. 19, 2020 declaration for U.S. Appl. No. 16/519,677. (Year: 2019).*
(Continued)

*Primary Examiner* — Dominic Lazaro
(74) *Attorney, Agent, or Firm* — Schwegman, Lundberg & Woessner, P.A.

(57) ABSTRACT

Embodiments of the present invention provide a method of treating a stricture in a nonvascular body lumen such as urethral strictures, benign prostatic hyperplasia (BPH) strictures, ureteral strictures, esophageal strictures, sinus strictures, and biliary tract strictures. Embodiments of the present invention provide a method for treating at least one of benign prostatic hyperplasia (BPH), prostate cancer, asthma, and chronic obstructive pulmonary disease (COPD). The method can include delivering, for example, via drug coated balloon catheters, anti-inflammatory and anti-proliferative drugs (e.g., rapamycin, paclitaxel, and their analogues) and one or more additives.

20 Claims, 2 Drawing Sheets

Related U.S. Application Data continuation of application No. 17/951,321, filed on Sep. 23, 2022, now Pat. No. 11,904,072, which is a continuation of application No. 17/107,136, filed on Nov. 30, 2020, now Pat. No. 11,484,628, which is a continuation of application No. 15/568,614, filed as application No. PCT/US2016/028652 on Apr. 21, 2016, now Pat. No. 10,888,640.

(60) Provisional application No. 62/152,559, filed on Apr. 24, 2015.

(51) Int. Cl.
    *A61K 31/439*     (2006.01)
    *A61L 29/08*     (2006.01)
    *A61M 25/10*     (2013.01)
    *A61P 31/00*     (2006.01)
    *A61P 37/06*     (2006.01)

(52) U.S. Cl.
    CPC ............... *A61P 31/00* (2018.01); *A61P 37/06* (2018.01); *A61L 2300/416* (2013.01); *A61M 25/10* (2013.01); *A61M 2025/105* (2013.01)

(56) References Cited

U.S. PATENT DOCUMENTS

| | | | |
|---|---|---|---|
| 5,263,931 A | 11/1993 | Miller | |
| 5,312,430 A * | 5/1994 | Rosenbluth | A61F 2/958 600/116 |
| 5,314,443 A | 5/1994 | Rudnick | |
| 5,419,763 A | 5/1995 | Hildebrand | |
| 5,423,755 A | 6/1995 | Kesten et al. | |
| 5,562,620 A | 10/1996 | Klein et al. | |
| 5,718,684 A | 2/1998 | Gupta | |
| 5,752,522 A | 5/1998 | Murphy | |
| 5,904,648 A | 5/1999 | Arndt et al. | |
| 6,059,713 A | 5/2000 | Urick et al. | |
| 6,268,390 B1 | 7/2001 | Kunz | |
| 6,306,421 B1 | 10/2001 | Kunz et al. | |
| 6,403,635 B1 | 6/2002 | Kinsella et al. | |
| 6,488,653 B1 | 12/2002 | Lombardo | |
| 6,495,579 B1 | 12/2002 | Hunter | |
| 6,515,009 B1 | 2/2003 | Kunz et al. | |
| 6,530,948 B1 | 3/2003 | Vrba | |
| 6,579,221 B1 | 6/2003 | Peterson | |
| 6,663,881 B2 | 12/2003 | Kunz et al. | |
| 6,730,064 B2 | 5/2004 | Ragheb et al. | |
| 7,803,149 B2 | 9/2010 | Bates et al. | |
| 7,811,622 B2 | 10/2010 | Bates et al. | |
| 7,882,841 B2 * | 2/2011 | Aljuri | A61B 18/1485 606/171 |
| 8,052,668 B2 | 11/2011 | Sih | |
| 8,092,864 B2 | 1/2012 | Isch et al. | |
| 8,241,249 B2 | 8/2012 | Wang | |
| 8,244,344 B2 | 8/2012 | Wang | |
| 8,257,305 B2 | 9/2012 | Speck et al. | |
| 8,366,660 B2 | 2/2013 | Wang | |
| 8,366,662 B2 | 2/2013 | Wang | |
| 8,403,910 B2 | 3/2013 | Wang | |
| 8,404,300 B2 | 3/2013 | Wang | |
| 8,414,525 B2 | 4/2013 | Wang | |
| 8,414,526 B2 | 4/2013 | Wang | |
| 8,414,909 B2 | 4/2013 | Wang | |
| 8,414,910 B2 | 4/2013 | Wang | |
| 8,425,459 B2 | 4/2013 | Wang | |
| 8,430,055 B2 | 4/2013 | Wang et al. | |
| 8,439,868 B2 | 5/2013 | Speck et al. | |
| 8,557,272 B2 | 10/2013 | Zhao | |
| 8,586,125 B2 | 11/2013 | Hossainy et al. | |
| 8,673,387 B2 | 3/2014 | Bates et al. | |
| 8,722,132 B2 | 5/2014 | Labrecque et al. | |
| 9,066,990 B2 | 6/2015 | Speck et al. | |
| 9,242,081 B2 | 1/2016 | Drasler et al. | |
| 9,728,840 B2 | 8/2017 | Shi et al. | |
| 10,245,419 B2 | 4/2019 | Drasler et al. | |
| 10,668,188 B2 | 6/2020 | Wang | |
| 10,675,386 B2 | 6/2020 | Wang | |
| 10,806,830 B2 | 10/2020 | Wang et al. | |
| 10,850,076 B2 | 12/2020 | Wang et al. | |
| 10,881,839 B2 | 1/2021 | Wang et al. | |
| 10,888,640 B2 * | 1/2021 | Wang | A61L 29/08 |
| 10,898,700 B2 * | 1/2021 | Wang | A61M 29/02 |
| 10,987,451 B2 | 4/2021 | Wang et al. | |
| 10,994,103 B2 | 5/2021 | Wang et al. | |
| 10,994,104 B2 * | 5/2021 | Wang | A61M 25/1002 |
| 11,439,801 B2 | 9/2022 | Wang et al. | |
| 11,471,655 B2 | 10/2022 | Wang et al. | |
| 11,471,656 B2 | 10/2022 | Wang et al. | |
| 11,484,628 B2 * | 11/2022 | Wang | A61L 29/16 |
| 11,504,450 B2 | 11/2022 | Wang et al. | |
| 11,648,337 B2 | 5/2023 | Wang et al. | |
| 11,648,338 B2 | 5/2023 | Wang et al. | |
| 11,730,864 B2 | 8/2023 | Wang et al. | |
| 11,826,532 B2 | 11/2023 | Wang et al. | |
| 11,826,533 B2 | 11/2023 | Wang et al. | |
| 11,904,072 B2 | 2/2024 | Wang et al. | |
| 11,925,729 B2 | 3/2024 | Wang et al. | |
| 11,938,287 B2 | 3/2024 | Wang et al. | |
| 11,957,853 B2 | 4/2024 | Wang et al. | |
| 2003/0203991 A1 | 10/2003 | Schottman et al. | |
| 2004/0098019 A1 | 5/2004 | Tomaschko et al. | |
| 2004/0144387 A1 | 7/2004 | Amar | |
| 2004/0267355 A1 | 12/2004 | Scott et al. | |
| 2005/0054978 A1 | 3/2005 | Segal et al. | |
| 2005/0196518 A1 | 9/2005 | Stenzel | |
| 2005/0249770 A1 | 11/2005 | Hunter | |
| 2006/0083768 A1 | 4/2006 | Labrecque et al. | |
| 2007/0005094 A1 | 1/2007 | Eaton et al. | |
| 2007/0009692 A1 | 1/2007 | Wang et al. | |
| 2007/0027523 A1 | 2/2007 | Toner et al. | |
| 2007/0031371 A1 | 2/2007 | Kozlowski | |
| 2007/0088255 A1 | 4/2007 | Toner et al. | |
| 2007/0260178 A1 | 11/2007 | Skerven et al. | |
| 2008/0025952 A1 | 1/2008 | Scheule et al. | |
| 2008/0113035 A1 | 5/2008 | Hunter | |
| 2008/0118544 A1 | 5/2008 | Wang | |
| 2008/0175887 A1 | 7/2008 | Wang | |
| 2008/0245375 A1 | 10/2008 | Trudel | |
| 2008/0255508 A1 | 10/2008 | Wang | |
| 2008/0255509 A1 | 10/2008 | Wang | |
| 2008/0255510 A1 | 10/2008 | Wang | |
| 2008/0276935 A1 | 11/2008 | Wang | |
| 2009/0018565 A1 | 1/2009 | To et al. | |
| 2009/0028920 A1 | 1/2009 | Hodges | |
| 2009/0171241 A1 | 7/2009 | Garcia et al. | |
| 2009/0283206 A1 | 11/2009 | Eskaros et al. | |
| 2010/0015200 A1 | 1/2010 | McClain et al. | |
| 2010/0030183 A1 | 2/2010 | Toner et al. | |
| 2010/0049182 A1 | 2/2010 | Ryan et al. | |
| 2010/0055294 A1 | 3/2010 | Wang et al. | |
| 2010/0076402 A1 | 3/2010 | Mazzone et al. | |
| 2010/0198150 A1 | 8/2010 | Michal et al. | |
| 2010/0209472 A1 | 8/2010 | Wang | |
| 2010/0233228 A1 | 9/2010 | Speck | |
| 2010/0285085 A1 | 11/2010 | Stankus et al. | |
| 2011/0008260 A1 | 1/2011 | Flanagan | |
| 2011/0015664 A1 | 1/2011 | Kangas et al. | |
| 2011/0098683 A1 | 4/2011 | Wiita et al. | |
| 2011/0144578 A1 | 6/2011 | Pacetti et al. | |
| 2011/0159169 A1 | 6/2011 | Wang | |
| 2011/0160575 A1 | 6/2011 | Beyar et al. | |
| 2011/0160658 A1 | 6/2011 | Wang | |
| 2011/0160660 A1 | 6/2011 | Wang | |
| 2011/0166548 A1 | 7/2011 | Wang | |
| 2011/0196340 A1 | 8/2011 | Barry et al. | |
| 2011/0295200 A1 | 12/2011 | Speck et al. | |
| 2011/0300221 A1 | 12/2011 | Kunz et al. | |
| 2012/0029426 A1 | 2/2012 | Wang | |
| 2012/0035530 A1 | 2/2012 | Wang | |
| 2012/0109105 A1 | 5/2012 | Cambronne | |
| 2012/0130174 A1 | 5/2012 | Simmons | |
| 2012/0172796 A1 | 7/2012 | Chappa | |

(56) References Cited

U.S. PATENT DOCUMENTS

| | | |
|---|---|---|
| 2012/0231037 A1 | 9/2012 | Levi et al. |
| 2012/0239001 A1 | 9/2012 | Barry et al. |
| 2012/0296274 A1* | 11/2012 | Slager .................... A61K 9/70 424/443 |
| 2012/0302954 A1 | 11/2012 | Zhao |
| 2012/0316633 A1 | 12/2012 | Flanagan et al. |
| 2013/0197434 A1 | 8/2013 | Wang |
| 2013/0197436 A1 | 8/2013 | Wang |
| 2013/0231638 A1 | 9/2013 | Speck et al. |
| 2013/0245058 A1 | 9/2013 | Hoffmann et al. |
| 2013/0253466 A1 | 9/2013 | Campbell et al. |
| 2013/0253475 A1 | 9/2013 | Wang |
| 2013/0261603 A1 | 10/2013 | Wang |
| 2013/0304029 A1 | 11/2013 | Barry et al. |
| 2014/0005541 A1 | 1/2014 | Bates et al. |
| 2014/0031843 A1 | 1/2014 | Rottenberg et al. |
| 2014/0228751 A1 | 8/2014 | Speck et al. |
| 2014/0228752 A1 | 8/2014 | Speck et al. |
| 2014/0378896 A1 | 12/2014 | Venturelli |
| 2015/0231375 A1 | 8/2015 | Kubo et al. |
| 2015/0273117 A1 | 10/2015 | Wang |
| 2016/0038648 A1 | 2/2016 | Gemborys |
| 2016/0082159 A1 | 3/2016 | Orlowski |
| 2016/0250388 A1 | 9/2016 | Wang |
| 2016/0338793 A1 | 11/2016 | Shohat et al. |
| 2017/0028105 A1 | 2/2017 | Ahlering et al. |
| 2017/0086929 A1 | 3/2017 | Moll et al. |
| 2017/0274179 A1 | 9/2017 | Sullivan et al. |
| 2018/0104383 A1 | 4/2018 | Wang et al. |
| 2019/0015639 A1 | 1/2019 | Wang et al. |
| 2019/0015640 A1 | 1/2019 | Wang et al. |
| 2019/0167854 A1 | 6/2019 | Wang |
| 2019/0344053 A1 | 11/2019 | Wang et al. |
| 2019/0374685 A1 | 12/2019 | Wang et al. |
| 2020/0254148 A1 | 8/2020 | Wang |
| 2020/0360571 A1 | 11/2020 | Wang et al. |
| 2021/0052862 A1 | 2/2021 | Wang et al. |
| 2021/0052863 A1 | 2/2021 | Wang et al. |
| 2021/0052864 A1 | 2/2021 | Wang et al. |
| 2021/0052865 A1 | 2/2021 | Wang et al. |
| 2021/0077666 A1 | 3/2021 | Wang et al. |
| 2021/0113742 A1 | 4/2021 | Wang et al. |
| 2021/0113823 A1 | 4/2021 | Wang et al. |
| 2021/0205502 A1 | 7/2021 | Wang et al. |
| 2021/0228780 A1 | 7/2021 | Wang et al. |
| 2021/0361918 A1 | 11/2021 | Wang et al. |
| 2022/0323653 A1 | 10/2022 | Wang et al. |
| 2022/0323732 A1 | 10/2022 | Wang et al. |
| 2023/0001163 A1 | 1/2023 | Wang et al. |
| 2023/0020891 A1 | 1/2023 | Wang et al. |
| 2023/0050453 A1 | 2/2023 | Wang et al. |
| 2023/0149602 A1 | 5/2023 | Wang et al. |
| 2023/0149672 A1 | 5/2023 | Wang et al. |
| 2023/0173240 A1 | 6/2023 | Wang et al. |
| 2023/0372593 A1 | 11/2023 | Wang et al. |
| 2024/0042183 A1 | 2/2024 | Wang et al. |
| 2024/0042184 A1 | 2/2024 | Flanagan et al. |
| 2024/0165303 A1 | 5/2024 | Wang et al. |
| 2024/0173525 A1 | 5/2024 | Wang et al. |

FOREIGN PATENT DOCUMENTS

| | | |
|---|---|---|
| CN | 101631514 A | 1/2010 |
| CN | 102357278 A | 2/2012 |
| CN | 202191333 U | 4/2012 |
| CN | 102573946 A | 7/2012 |
| CN | 203138758 U | 8/2013 |
| CN | 103328033 A | 9/2013 |
| CN | 103458954 A | 12/2013 |
| CN | 104780859 A | 7/2015 |
| CN | 104936629 A | 9/2015 |
| CN | 107088258 A | 8/2017 |
| CN | 107635593 A | 1/2018 |
| CN | 109414528 A | 3/2019 |
| CN | 111166942 A | 5/2020 |
| CN | 113727750 A | 11/2021 |
| CN | 109414528 B | 6/2022 |
| CN | 115227880 A | 10/2022 |
| EP | 0474906 A1 | 3/1992 |
| EP | 1135165 A1 | 9/2001 |
| EP | 1143968 B1 | 8/2003 |
| EP | 1384840 A1 | 1/2004 |
| EP | 1539266 B1 | 4/2008 |
| EP | 2292225 B1 | 5/2012 |
| EP | 2098230 B1 | 6/2012 |
| EP | 2262547 B1 | 1/2013 |
| EP | 2324866 B1 | 6/2014 |
| EP | 2324867 B1 | 6/2014 |
| EP | 2531229 B1 | 12/2014 |
| EP | 2451496 B1 | 7/2015 |
| EP | 2911711 | 9/2015 |
| EP | 3442612 B1 | 8/2020 |
| JP | H06343597 A | 12/1994 |
| JP | 2001238953 | 9/2001 |
| JP | 2007229499 A | 9/2007 |
| JP | 2008541835 | 11/2008 |
| JP | 2009022759 A | 2/2009 |
| JP | 2010540159 A | 12/2010 |
| JP | 2011024953 | 2/2011 |
| JP | 2012502690 A | 2/2012 |
| JP | 2013001415 A | 1/2013 |
| JP | 2013523209 A | 6/2013 |
| JP | 2014523790 A | 9/2014 |
| JP | 2015536709 A | 12/2015 |
| JP | 2016503330 A | 2/2016 |
| JP | 2016036730 A | 3/2016 |
| JP | 2016518200 A | 6/2016 |
| JP | 2017507741 A | 3/2017 |
| JP | 2018517454 A | 7/2018 |
| JP | 2019137680 A | 8/2019 |
| JP | 2019523032 A | 8/2019 |
| JP | 2019218354 A | 12/2019 |
| JP | 2020049269 A | 4/2020 |
| JP | 2020075155 A | 5/2020 |
| JP | 6833218 B2 | 2/2021 |
| JP | 2021072908 A | 5/2021 |
| JP | 2022521000 A | 4/2022 |
| JP | 2023052847 A | 4/2023 |
| JP | 2023082069 A | 6/2023 |
| WO | WO-9728840 A1 | 8/1997 |
| WO | WO-9803218 A1 | 1/1998 |
| WO | WO-0025848 A2 | 5/2000 |
| WO | WO-0032238 | 6/2000 |
| WO | WO-2011147407 A2 | 12/2001 |
| WO | 2006130194 | 12/2006 |
| WO | WO-2009051614 A1 * | 4/2009 ........... A61K 31/337 |
| WO | WO-2011008393 A2 | 1/2011 |
| WO | WO-2011119159 A1 | 9/2011 |
| WO | WO-2012122023 A2 | 9/2012 |
| WO | WO-2013015941 A1 | 1/2013 |
| WO | WO-2013086698 A1 | 6/2013 |
| WO | WO-2013110158 A1 | 8/2013 |
| WO | WO-2014066085 A1 | 5/2014 |
| WO | WO-2014087395 A1 | 6/2014 |
| WO | WO-2014177678 A1 | 11/2014 |
| WO | WO-2015136106 A1 | 9/2015 |
| WO | WO-2016073294 A1 | 5/2016 |
| WO | WO-2016118923 A1 | 7/2016 |
| WO | WO-2016172343 A1 | 10/2016 |
| WO | WO-2018204782 A1 | 11/2018 |
| WO | WO-2020172560 A1 | 8/2020 |

OTHER PUBLICATIONS

"U.S. Appl. No. 17/843,208, Response filed Jun. 27, 2023 to Non Final Office Action mailed May 25, 2023", 8 pgs.

"U.S. Appl. No. 18/097,698, Response filed Jun. 27, 2023 to Non Final Office Action mailed Apr. 13, 2023", 11 pgs.

"U.S. Appl. No. 17/951,321, Non Final Office Action mailed Jul. 7, 2023", 8 pgs.

(56) References Cited

OTHER PUBLICATIONS

"European Application Serial No. 23166193.5, Response filed Jun. 20, 2023 to Invitation to Remedy Deficiencies mailed Apr. 17, 2023", 6 pgs.
"U.S. Appl. No. 17/843,208, Notice of Allowance mailed Jul. 26, 2023", 11 pgs.
"U.S. Appl. No. 18/097,698, Notice of Allowance mailed Jul. 26, 2023", 11 pgs.
"Declaration for U.S. Appl. No. 16/519,677", (Jun. 19, 2020), 4 pgs.
"Chinese Application Serial No. 202080030597.8, Office Action mailed Jul. 29, 2023", w English translation, 9 pgs.
"U.S. Appl. No. 18/098,370, Response filed Aug. 8, 2023 to Non Final Office Action mailed May 25, 2023", 13 pgs.
"U.S. Appl. No. 17/944,259, Non Final Office Action mailed Aug. 10, 2023", 6 pgs.
"U.S. Appl. No. 17/967,259, Non Final Office Action mailed Aug. 17, 2023", 6 pgs.
"Chinese Application Serial No. 201680029925.6, Notice of Reexamination mailed Aug. 7, 2023", w English Translation, 15 pgs.
"European Application Serial No. 23166049.9, Communication Pursuant to Article 94(3) EPC mailed Aug. 28, 2023", 12 pgs.
"U.S. Appl. No. 17/843,150, Non Final Office Action mailed Aug. 31, 2023", 6 pgs.
"U.S. Appl. No. 18/097,698, Corrected Notice of Allowability mailed Sep. 1, 2023", 9 pgs.
"U.S. Appl. No. 18/098,370, Non Final Office Action mailed Sep. 6, 2023", 6 pgs.
"U.S. Appl. No. 17/951,321, Response filed Sep. 20, 2023 to Non Final Office Action mailed Jul. 7, 2023", 10 pgs.
"Chinese Application Serial No. 201680029925.6, Response filed Sep. 21, 2023 to Office Action mailed Aug. 7, 2023", W English Translation, 47 pgs.
"European Application Serial No. 23166193.5, Extended European Search Report mailed Oct. 4, 2023", 6 pgs.
"U.S. Appl. No. 17/951,321, Notice of Allowance mailed Oct. 12, 2023", 12 pgs.
"U.S. Appl. No. 17/951,321, Corrected Notice of Allowability mailed Oct. 27, 2023", 8 pgs.
"U.S. Appl. No. 17/967,259, Response filed Nov. 9, 2023 to Non Final Office Action mailed Aug. 17, 2023", 8 pgs.
"U.S. Appl. No. 17/843,150, Response filed Nov. 9, 2023 to Non Final Office Action mailed Aug. 31, 2023", 8 pgs.
"U.S. Appl. No. 17/944,259, Response filed Nov. 9, 2023 to Non Final Office Action mailed Aug. 10, 2023", 7 pgs.
"U.S. Appl. No. 17/967,259, Notice of Allowance mailed Nov. 28, 2023", 10 pgs.
"U.S. Appl. No. 17/944,259, Notice of Allowance mailed Nov. 28, 2023", 11 pgs.
"U.S. Appl. No. 17/255,701, Non Final Office Action mailed Nov. 29, 2023", 37 pgs.
"Japanese Application Serial No. 2021-549230, Notification of Reasons for Refusal mailed Nov. 28, 2023", w English Translation, 10 pgs.
"U.S. Appl. No. 18/098,370, Response filed Dec. 4, 2023 to Non Final Office Action mailed Sep. 6, 2023", 8 pgs.
"Japanese Application Serial No. 2023-014484 Non-Final Office Action mailed on Dec. 5, 2023", w English Translation, 3 pgs.
"U.S. Appl. No. 18/098,370, Notice of Allowance mailed Dec. 13, 2023", 10 pgs.
"Declaration for U.S. Appl. No. 16/519,677", (Jun. 19, 2019), 4 pgs.
Bardini, R, "Anastomosis", World J. Surg. 18, (1994), 373-378.
"37 C.F.R. section 1.132 Declaration for U.S. Appl. No. 16/135,436, filed Jan. 13, 2020", (2020), 5 pgs.
"Acetic Acid", ChemSpider, Accessed online on Mar. 13, 2021 at <https://www.chemspider.com/Search.aspx?q=acetic+acidl>, (2021), 2 pgs.
"U.S. Appl. No. 14/438,327, Advisory Action mailed Jul. 18, 2018", 6 pgs.
"U.S. Appl. No. 14/438,327, Corrected Notice of Allowability mailed May 5, 2020", 3 pgs.
"U.S. Appl. No. 14/438,327, Examiner Interview Summary mailed Feb. 12, 2020", 3 pgs.
"U.S. Appl. No. 14/438,327, Final Office Action mailed Apr. 2, 2018", 14 pgs.
"U.S. Appl. No. 14/438,327, Final Office Action mailed May 3, 2017", 10 pgs.
"U.S. Appl. No. 14/438,327, Final Office Action mailed Aug. 9, 2019", 20 pgs.
"U.S. Appl. No. 14/438,327, Non Final Office Action mailed Jan. 7, 2020", 11 pgs.
"U.S. Appl. No. 14/438,327, Non Final Office Action mailed Jan. 28, 2019", 14 pgs.
"U.S. Appl. No. 14/438,327, Non Final Office Action malled Sep. 29, 2017", 11 pgs.
"U.S. Appl. No. 14/438,327, Non Final Office Action mailed Oct. 6, 2016", 10 pgs.
"U.S. Appl. No. 14/438,327, Notice of Allowance mailed Apr. 22, 2020", 10 pgs.
"U.S. Appl. No. 14/438,327, Preliminary Amendment filed Jul. 28, 2015", 9 pgs.
"U.S. Appl. No. 14/438,327, Response filed Feb. 7, 2020 to Non Final Office Action mailed Jan. 7, 2020", 13 pgs.
"U.S. Appl. No. 14/438,327, Response filed Apr. 16, 2019 to Non Final Office Action mailed Jan. 28, 2019", 29 pgs.
"U.S. Appl. No. 14/438,327, Response filed Jun. 1, 2018 to Final Office Action mailed Apr. 2, 2018", 16 pgs.
"U.S. Appl. No. 14/438,327, Response filed Jul. 27, 2017 to Final Office Action mailed May 3, 2017", 13 pgs.
"U.S. Appl. No. 14/438,327, Response filed Aug. 1, 2018 to Advisory Action mailed Jul. 18, 2018 and Final Office Action mailed Apr. 2, 2018", 17 pgs.
"U.S. Appl. No. 14/438,327, Response filed Aug. 24, 2016 to Restriction Requirement mailed Jul. 12, 2016", 9 pgs.
"U.S. Appl. No. 14/438,327, Response filed Dec. 3, 2019 to Final Office Action mailed Aug. 9, 2019", 32 pgs.
"U.S. Appl. No. 14/438,327, Response filled Dec. 15, 2017 to Non Final Office Action mailed Sep. 29, 2017", 16 pgs.
"U.S. Appl. No. 14/438,327, Response filed Dec. 28, 2016 to Non Final Office Action mailed Oct. 6, 2016", 13 pgs.
"U.S. Appl. No. 14/438,327, Restriction Requirement mailed Jul. 12, 2016", 9 pgs.
"U.S. Appl. No. 15/568,614, Corrected Notice of Allowability mailed Nov. 30, 2020", 8 pgs.
"U.S. Appl. No. 15/568,614, Final Office Action mailed May 15, 2020", 25 pgs.
"U.S. Appl. No. 15/568,614, Non Final Office Action mailed Nov. 18, 2019", 22 pgs.
"U.S. Appl. No. 15/568,614, Notice of Allowance mailed Sep. 30, 2020", 10 pgs.
"U.S. Appl. No. 15/568,614, Notice of Non-Responsive Amendment mailed Jul. 1, 2019", 2 pgs.
"U.S. Appl. No. 15/568,614, Response filed Feb. 10, 2020 to Non Final Office Action mailed Nov. 18, 2019", 17 pgs.
"U.S. Appl. No. 15/568,614, Response filed Mar. 20, 2019 to Restriction Requirement mailed Feb. 8, 2019", 8 pgs.
"U.S. Appl. No. 15/568,614, Response filed Jul. 9, 2019 to Non-Responsive Amendment mailed Jul. 1, 2019 & Restriction Requirement mailed Feb. 8, 2019", 8 pgs.
"U.S. Appl. No. 15/568,614, Response filed Jul. 14, 2020 to Final Office Action mailed May 15, 2020", 23 pgs.
"U.S. Appl. No. 15/568,614, Restriction Requirement mailed Feb. 8, 2019", 9 pgs.
"U.S. Appl. No. 16/135,436, Corrected Notice of Allowability mailed Sep. 11, 2020", 7 pgs.
"U.S. Appl. No. 16/135,436, Examiner Interview Summary mailed Apr. 8, 2020", 3 pgs.
"U.S. Appl. No. 16/135,436, Final Office Action mailed Nov. 29, 2019", 41 pgs.
"U.S. Appl. No. 16/135,436, Non Final Office Action mailed Mar. 5, 2020", 48 pgs.
"U.S. Appl. No. 16/135,436, Non Final Office Action mailed Jul. 29, 2019", 38 pgs.

(56) References Cited

OTHER PUBLICATIONS

"U.S. Appl. No. 16/135,436, Notice of Allowance mailed Jul. 10, 2020", 10 pgs.
"U.S. Appl. No. 16/135,436, Notice of Non-Responsive Amendment mailed Mar. 8, 2019", 2 pgs.
"U.S. Appl. No. 16/135,436, Response filed Jan. 13, 2020 to Final Office Action mailed Nov. 29, 2019", 22 pgs.
"U.S. Appl. No. 16/135,436, Response filed Mar. 28, 2019 to Notice of Non-Responsive Amendment mailed Mar. 8, 2019", 10 pgs.
"U.S. Appl. No. 16/135,436, Response filed Apr. 6, 2020 to Non Final Office Action mailed Mar. 5, 2020", 21 pgs.
"U.S. Appl. No. 16/135,436, Response filed Aug. 21, 2019 to Non Final Office Action mailed Jul. 29, 2019", 18 pgs.
"U.S. Appl. No. 16/135,436, Response filed Nov. 14, 2018 to Restriction Requirement mailed Nov. 2, 2018", 10 pgs.
"U.S. Appl. No. 16/135,436, Restriction Requirement mailed Nov. 2, 2018", 7 pgs.
"U.S. Appl. No. 16/135,472, Corrected Notice of Allowability mailed Nov. 30, 2020", 8 pgs.
"U.S. Appl. No. 16/135,472, Examiner Interview Summary mailed May 19, 2020", 4 pgs.
"U.S. Appl. No. 16/135,472, Final Office Action mailed Aug. 21, 2020", 6 pgs.
"U.S. Appl. No. 16/135,472, Final Office Action mailed Nov. 29, 2019", 43 pgs.
"U.S. Appl. No. 16/135,472, Non Final Office Action mailed Mar. 19, 2020", 56 pgs.
"U.S. Appl. No. 16/135,472, Non Final Office Action mailed Jul. 30, 2019", 40 pgs.
"U.S. Appl. No. 16/135,472, Notice of Allowance mailed Oct. 7, 2020", 9 pgs.
"U.S. Appl. No. 16/135,472, Notice of Non Responsive Amendment mailed Mar. 8, 2019", 2 pgs.
"U.S. Appl. No. 16/135,472, Response filed Jan. 13, 2020 to Final Office Action mailed Nov. 29, 2019", 27 pgs.
"U.S. Appl. No. 16/135,472, Response filed Mar. 28, 2019 to Notice of Non Responsive Amendment mailed Mar. 8, 2019", 10 pgs.
"U.S. Appl. No. 16/135,472, Response filed May 15, 2020 to Non Final Office Action mailed Mar. 19, 2020", 29 pgs.
"U.S. Appl. No. 16/135,472, Response filed Sep. 4, 2020 to Final Office Action mailed Aug. 21, 2020", 12 pgs.
"U.S. Appl. No. 16/135,472, Response filed Nov. 14, 2018 to Restriction Requirement mailed Nov. 2, 2018", 10 pgs.
"U.S. Appl. No. 16/135,472, Response filed Aug. 21, 2019 to Non Final Office Action mailed Jul. 30, 2019", 23 pgs.
"U.S. Appl. No. 16/135,472, Restriction Requirement mailed Nov. 2, 2018", 5 pgs.
"U.S. Appl. No. 16/267,434, Corrected Notice of Allowability mailed May 13, 2020", 3 pgs.
"U.S. Appl. No. 16/267,434, Final Office Action mailed Mar. 30, 2020", 18 pgs.
"U.S. Appl. No. 16/267,434, Final Office Action mailed Jun. 14, 2019", 15 pgs.
"U.S. Appl. No. 16/267,434, Non Final Office Action mailed Mar. 22, 2019", 11 pgs.
"U.S. Appl. No. 16/267,434, Non Final Office Action mailed Nov. 18, 2019", 19 pgs.
"U.S. Appl. No. 16/267,434, Notice of Allowance mailed Apr. 22, 2020", 10 pgs.
"U.S. Appl. No. 16/267,434, Response filed Feb. 13, 2020 to Non Final Office Action mailed Nov. 18, 2019", 17 pgs.
"U.S. Appl. No. 16/267,434, Response filed Mar. 31, 2020 to Final Office Action mailed Mar. 30, 2020", 8 pgs.
"U.S. Appl. No. 16/267,434, Response Filed Apr. 24, 2019 to Non-Final Office Action Mailed Mar. 22, 2019", 11 pgs.
"U.S. Appl. No. 16/267,434, Response filed Sep. 11, 2019 to Final Office Action mailed Jun. 14, 2019", 17 pgs.
"U.S. Appl. No. 16/519,677, Corrected Notice of Allowability mailed Nov. 30, 2020", 7 pgs.
"U.S. Appl. No. 16/519,677, Non Final Office Action mailed Mar. 19, 2020", 31 pgs.
"U.S. Appl. No. 16/519,677, Notice of Allowance mailed Sep. 21, 2020", 10 pgs.
"U.S. Appl. No. 16/519,677, Response filed Jun. 19, 2020 to Non Final Office Action mailed Mar. 19, 2020", 19 pgs.
"U.S. Appl. No. 16/519,677, Response filed Dec. 13, 2019 to Restriction Requirement mailed Nov. 20, 2019", 10 pgs.
"U.S. Appl. No. 16/519,677, Restriction Requirement mailed Nov. 20, 2019", 5 pgs.
"U.S. Appl. No. 16/519,720, Final Office Action mailed Aug. 21, 2020", 23 pgs.
"U.S. Appl. No. 16/519,720, Non Final Office Action mailed Feb. 6, 2020", 23 pgs.
"U.S. Appl. No. 16/519,720, Notice of Allowance mailed Oct. 21, 2020", 8 pgs.
"U.S. Appl. No. 16/519,720, Response filed May 6, 2020 to Non Final Office Action mailed Feb. 6, 2020", 19 pgs.
"U.S. Appl. No. 16/519,720, Response filed Sep. 4, 2020 to Final Office Action mailed Aug. 21, 2020", 12 pgs.
"U.S. Appl. No. 16/519,720, Response filed Oct. 31, 2019 to Restriction Requirement mailed Oct. 18, 2019", 10 pgs.
"U.S. Appl. No. 16/519,720, Restriction Requirement mailed Oct. 18, 2019", 5 pgs.
"U.S. Appl. No. 16/864,373, Examiner Interview Summary mailed Jul. 12, 2021", 2 pgs.
"U.S. Appl. No. 16/864,373, Final Office Action mailed May 25, 2021", 44 pgs.
"U.S. Appl. No. 16/864,373, Non Final Office Action mailed Mar. 18, 2021", 32 pgs.
"U.S. Appl. No. 16/864,373, Response filed Apr. 6, 2021 to Non Final Office Action mailed Mar. 18, 2021", 25 pgs.
"U.S. Appl. No. 16/864,373, Response filed Dec. 10, 2020 to Restriction Requirement mailed Nov. 17, 2020", 7 pgs.
"U.S. Appl. No. 16/864,373, Restriction Requirement mailed Nov. 17, 2020", 5 pgs.
"U.S. Appl. No. 16/986,683, Corrected Notice of Allowability mailed Mar. 17, 2021", 6 pgs.
"U.S. Appl. No. 16/986,683, Non Final Office Action mailed Oct. 29, 2020", 14 pgs.
"U.S. Appl. No. 16/986,683, Notice of Allowance mailed Jan. 4, 2021", 9 pgs.
"U.S. Appl. No. 16/986,683, Response filed Dec. 4, 2020 to Non Final Office Action mailed Oct. 29, 2020", 9 pgs.
"U.S. Appl. No. 17/080,088, Corrected Notice of Allowability mailed Jul. 12, 2022", 8 pgs.
"U.S. Appl. No. 17/080,088, Non Final Office Action mailed Mar. 3, 2022", 7 pgs.
"U.S. Appl. No. 17/080,088, Notice of Allowance mailed Jun. 14, 2022", 11 pgs.
"U.S. Appl. No. 17/080,088, Response filed May 27, 2022 to Non Final Office Action mailed Mar. 3, 2022", 12 pgs.
"U.S. Appl. No. 17/080,114, Non Final Office Action mailed Mar. 3, 2022", 7 pgs.
"U.S. Appl. No. 17/080,114, Notice of Allowance mailed Jun. 14, 2022", 12 pgs.
"U.S. Appl. No. 17/080,114, Response filed May 27, 2022 to Non Final Office Action mailed Mar. 3, 2022", 9 pgs.
"U.S. Appl. No. 17/080,140, Non Final Office Action mailed Feb. 19, 2021", 13 pgs.
"U.S. Appl. No. 17/080,140, Notice of Allowance mailed Mar. 18, 2021", 12 pgs.
"U.S. Appl. No. 17/080,140, Notice of Allowance/Base Issue Fee mailed Mar. 18, 2021", 12 pgs.
"U.S. Appl. No. 17/080,140, Response filed Mar. 9, 2021 to Non Final Office Action mailed Feb. 19, 2021", 10 pgs.
"U.S. Appl. No. 17/080,199, Non Final Office Action mailed Feb. 19, 2021", 17 pgs.
"U.S. Appl. No. 17/080,199, Notice of Allowance mailed Mar. 19, 2021", 11 pgs.
"U.S. Appl. No. 17/080,199, Response filed Mar. 9, 2021 to Non Final Office Action mailed Feb. 19, 2021", 8 pgs.

(56) References Cited

OTHER PUBLICATIONS

"U.S. Appl. No. 17/107,136, Corrected Notice of Allowability mailed Jul. 12, 2022", 7 pgs.
"U.S. Appl. No. 17/107,136, Non Final Office Action mailed Mar. 4, 2022", 6 pgs.
"U.S. Appl. No. 17/107,136, Notice of Allowance mailed Jun. 23, 2022", 11 pgs.
"U.S. Appl. No. 17/107,136, Response filed May 27, 2022 to Non Final Office Action mailed Mar. 4, 2022", 9 pgs.
"U.S. Appl. No. 17/108,517, Corrected Notice of Allowability mailed Jul. 12, 2022", 6 pgs.
"U.S. Appl. No. 17/108,517, Non Final Office Action mailed Mar. 3, 2022", 5 pgs.
"U.S. Appl. No. 17/108,517, Notice of Allowance mailed Jun. 14, 2022", 10 pgs.
"U.S. Appl. No. 17/108,517, Response filed May 27, 2022 to Non Final Office Action mailed Mar. 3, 2022", 7 pgs.
"U.S. Appl. No. 17/133,088, Corrected Notice of Allowability mailed Aug. 24, 2022", 8 pgs.
"U.S. Appl. No. 17/133,088, Notice of Allowance mailed Jul. 25, 2022", 10 pgs.
"U.S. Appl. No. 17/133,088, Preliminary Amendment filed Dec. 2, 2021", 6 pgs.
"U.S. Appl. No. 17/133,088, Preliminary Amendment filed Dec. 29, 2020", 8 pgs.
"U.S. Appl. No. 17/208,518, Corrected Notice of Allowability mailed Feb. 15, 2023", 7 pgs.
"U.S. Appl. No. 17/208,518, Non Final Office Action mailed Oct. 6, 2022", 5 pgs.
"U.S. Appl. No. 17/208,518, Notice of Allowance mailed Jan. 30, 2023", 10 pgs.
"U.S. Appl. No. 17/208,518, Response filed Jan. 4, 2023 to Non Final Office Action mailed Oct. 6, 2022", 9 pgs.
"U.S. Appl. No. 17/208,561, Corrected Notice of Allowability mailed Feb. 15, 2023", 7 pgs.
"U.S. Appl. No. 17/208,561, Non Final Office Action mailed Oct. 6, 2022", 6 pgs.
"U.S. Appl. No. 17/208,561, Notice of Allowance mailed Jan. 30, 2023", 10 pgs.
"U.S. Appl. No. 17/208,561, Response filed Jan. 4, 2023 to Non Final Office Action mailed Oct. 6, 2022", 10 pgs.
"U.S. Appl. No. 17/255,701, Preliminary Amendment filed Dec. 2, 2021", 9 pgs.
"U.S. Appl. No. 17/843,208, Non Final Office Action mailed May 25, 2023", 7 pgs.
"U.S. Appl. No. 18/097,690, Non Final Office Action mailed Mar. 31, 2023", 8 pgs.
"U.S. Appl. No. 18/097,690, Notice of Allowance mailed Jun. 23, 2023", 11 pgs.
"U.S. Appl. No. 18/097,690, Response filed May 15, 2023 to Non Final Office Action mailed Mar. 31, 2023", 11 pgs.
"U.S. Appl. No. 18/097,698, Non Final Office Action mailed Apr. 13, 2023", 10 pgs.
"U.S. Appl. No. 18/098,370, Non Final Office Action mailed May 25, 2023", 24 pgs.
"Chinese Application Serial No. 202210624650.8, Voluntary Amendment filed Feb. 15, 2023", w/ English Claims, 11 pgs.
"Chinese Application Serial No. 201380055869.X, Notice of Reexamination mailed Nov. 21, 2019", w/ English Translation, 8 pgs.
"Chinese Application Serial No. 201380055869.X, Office Action mailed May 26, 2016", w/English Translation, 6 pgs.
"Chinese Application Serial No. 201380055869.X, Office Action mailed Jun. 19, 2017", With English Translation, 13 pgs.
"Chinese Application Serial No. 201380055869.X, Office Action mailed Nov. 27, 2017", W/English Translation, 13 pgs.
"Chinese Application Serial No. 201380055869.X, Office Action mailed Dec. 15, 2016", with English Translation, 20 pgs.
"Chinese Application Serial No. 201380055869.X, Respone filed Apr. 12, 2018 to Office Action mailed Nov. 27, 2017", w/ English Claims, 17 pgs.
"Chinese Application Serial No. 201380055869.X, Response filed Sep. 4, 2017 to Office Action mailed Jun. 19, 2017", w/ English Claims, 17 pgs.
"Chinese Application Serial No. 201380055869.X, Response filed Sep. 9, 2016 to Office Action mailed May 26, 2016", (With English Translation), 18 pgs.
"Chinese Application Serial No. 201380055869.X, Response filed Feb. 28, 2017 to Office Action mailed Dec. 15, 2016", w/ English Claims, 21 pgs.
"Chinese Application Serial No. 201680029925.6, Decision of Rejection mailed Mar. 1, 2021", w/ English Translation, 20 pgs.
"Chinese Application Serial No. 201680029925.6, Office Action mailed Feb. 21, 2020", w/ English translation, 15 pgs.
"Chinese Application Serial No. 201680029925.6, Office Action mailed Jul. 16, 2020", w/English Translation, 22 pgs.
"Chinese Application Serial No. 201680029925.6, Office Action mailed Oct. 22, 2020", w/ English translation, 25 pgs.
"Chinese Application Serial No. 201680029925.6, Response filed Jan. 5, 2021 to Office Action mailed Oct. 22, 2020", w/ English Claims, 20 pgs.
"Chinese Application Serial No. 201680029925.6, Response filed Jul. 6, 2020 to Office Action mailed Feb. 21, 2020", w/English Claims, 36 pgs.
"Chinese Application Serial No. 201680029925.6, Response filed Jun. 16, 2021 to Decision of Rejection mailed Mar. 1, 2021", w/English Claims, 42 pgs.
"Chinese Application Serial No. 201880002506.2, Office Action mailed Jul. 29, 2021", w/ English Translation, 19 pgs.
"Chinese Application Serial No. 201880002506.2, Response filed Mar. 17, 2022 to Examiner Telephone Interview Summary w/o Official Summary issued by Foreign PTO on Mar. 16, 2022", w/English Claims, 14 pgs.
"Chinese Application Serial No. 201880002506.2, Response filed Nov. 12, 2021 to Office Action mailed Jul. 29, 2021", w/English Claims, 22 pgs.
"Chinese Application Serial No. 202010009827.4, Decision of Rejection mailed Sep. 26, 2022", w/ English translation, 10 pgs.
"Chinese Application Serial No. 202010009827.4, Office Action mailed Feb. 25, 2022", w/ English translation, 13 pgs.
"Chinese Application Serial No. 202010009827.4, Office Action mailed Jun. 23, 2022", W/English Translation, 16 pgs.
"Chinese Application Serial No. 202010009827.4, Office Action mailed Jul. 30, 2021", w/ English Translation, 11 pgs.
"Chinese Application Serial No. 202010009827.4, Response filed Jan. 9, 2023 to Decision of Rejection mailed Sep. 26, 2022", w/ English Claims, 16 pgs.
"Chinese Application Serial No. 202010009827.4, Response filed Sep. 7, 2022 to Office Action mailed Jun. 23, 2022", w/ English Claims, 8 pgs.
"Chinese Application Serial No. 202010009827.4, Response filed Dec. 13, 2021 to Office Action mailed Jul. 30, 2021", w/English Claims, 15 pgs.
"Chinese Application Serial No. 202210624650.8, Office Action mailed Jun. 3, 2022", W/O English Translation, 2 pgs.
"Declaration for U.S. Appl. No. 15/519,677", filed Jul. 23, 2019, 4 pgs.
"Declaration from U.S. Appl. No. 16/519,677", filed Jul. 14, 2020.
"Declaration from U.S. Appl. No. 16/519,677, filed Jul. 23, 2019".
"Declaration Under 37 C.F.R 1.132", (Jul. 14, 2020), 4 pgs.
"Definition of "stricture" Merriam-Webster", Accessed online on Mar. 13, 2021 at <https://www.merriam-webster.com/dictionary/stricture>, (2021), 11 pgs.
"Drug Coated Balloon Catheters for Nonvascular Strictures".
"European Application Serial No. 20712766.3, Response to Communication pursuant to Rules 161 and 162 filed May 2, 2022", 7 pgs.
"European Application Serial No. 13848400.1, Communication Pursuant to Article 94(3) EPC mailed Apr. 9, 2018", 7 pgs.
"European Application Serial No. 13848400.1, Communication Pursuant to Article 94(3) EPC mailed Apr. 24, 2020", 8 pgs.
"European Application Serial No. 13848400.1, Communication Pursuant to Article 94(3) EPC mailed Jun. 4, 2019", 9 pgs.

(56) References Cited

OTHER PUBLICATIONS

"European Application Serial No. 13848400.1, Extended European Search Report mailed Apr. 28, 2016", 8 pgs.
"European Application Serial No. 13848400.1, Response filed Sep. 14, 2018 to Communication Pursuant to Article 94(3) EPC mailed Apr. 9, 2018", 42 pgs.
"European Application Serial No. 13848400.1, Response filed Oct. 14, 2016 to Extended European Search Report mailed Apr. 28, 2016", 17 pgs.
"European Application Serial No. 13848400.1, Response filed Oct. 19, 2015 to Communication pursuant to Rules 161(1) and 162 EPC mailed Jun. 2, 2015", 17 pgs.
"European Application Serial No. 13848400.1, Response filed Oct. 19, 2020 to Communication Pursuant to Article 94(3) EPC mailed Apr. 24, 2020", 13 pgs.
"European Application Serial No. 13848400.1, Response filed Dec. 16, 2019 to Communication Pursuant to Article 94(3) EPC mailed Jun. 4, 2019", 30 pgs.
"European Application Serial No. 13848400.1, Summons to attend oral proceedings mailed May 6, 2021", 8 pgs.
"European Application Serial No. 16783856.4, Communication Pursuant to Article 94(3) EPC mailed Jan. 15, 2021", 6 pgs.
"European Application Serial No. 16783856.4, Communication Pursuant to Article 94(3) EPC mailed Aug. 29, 2022", 11 pgs.
"European Application Serial No. 16783856.4, Extended European Search Report mailed Nov. 9, 2018", 7 pgs.
"European Application Serial No. 16783856.4, Response filed Mar. 8, 2023 to Communication Pursuant to Article 94(3) EPC mailed Aug. 29, 2022", 10 pgs.
"European Application Serial No. 16783856.4, Response filed May 5, 2021 to Communication Pursuant to Article 94(3) EPC mailed Jan. 15, 2021", 11 pgs.
"European Application Serial No. 16783856.4, Response filed May 28, 2019 to Extended European Search Report mailed Nov. 9, 2018", 16 pgs.
"European Application Serial No. 16783856.4, Response filed Jun. 22, 2018 to Communication pursuant to Rules 161(2) & 162 EPC mailed Dec. 13, 2017", 11 pgs.
"European Application Serial No. 18794752.8, Communication Pursuant to Article 94(3) EPC mailed Apr. 10, 2019", 8 pgs.
"European Application Serial No. 18794752.8, Extended European Search Report mailed Mar. 29, 2019", 5 pgs.
"European Application Serial No. 18794752.8, Response filed Aug. 5, 2019 to Communication Pursuant to Article 94(3) EPC mailed Apr. 10, 2019", 55 pgs.
"European Application Serial No. 20188898.9, Communication Pursuant to Article 94(3) EPC mailed Aug. 31, 2022", 8 pgs.
"European Application Serial No. 20188898.9, Extended European Search Report mailed Dec. 10, 2020", 12 pgs.
"European Application Serial No. 20188898.9, Response filed Mar. 10, 2023 to Communication Pursuant to Article 94(3) EPC mailed Aug. 31, 2022", 7 pgs.
"European Application Serial No. 20188898.9, Response filed Jun. 28, 2021 to Extended European Search Report mailed Dec. 10, 2020", w/English Claims, 18 pgs.
"Gentisic Acid", ChemSpider, Accessed online on Mar. 13, 2021 at <https://www.chemspider.com/Chemical-Structure.3350.html>. (Year: 2021), (2021), 3 pgs.
"International Application Serial No. PCT/US2013/064842, International Preliminary Report on Patentability mailed May 7, 2015", 12 pgs.
"International Application Serial No. PCT/US2013/064842, International Search Report mailed Jan. 17, 2014", 3 pgs.
"International Application Serial No. PCT/US2013/064842, Written Opinion mailed Jan. 17, 2014", 10 pgs.
"International Application Serial No. PCT/US2016/028652, International Preliminary Report on Patentability mailed Nov. 2, 2017", 10 pgs.
"International Application Serial No. PCT/US2016/028652, International Search Report mailed Jul. 26, 2016", 2 pgs.
"International Application Serial No. PCT/US2016/028652, Written Opinion mailed Jul. 26, 2016". 8 pgs.
"International Application Serial No. PCT/US2018/031083, International Preliminary Report on Patentability mailed Nov. 14, 2019", 35 pgs.
"International Application Serial No. PCT/US2018/031083, International Search Report mailed Jul. 27, 2018", 4 pgs.
"International Application Serial No. PCT/US2018/031083, Written Opinion mailed Jul. 27, 2018", 33 pgs.
"International Application Serial No. PCT/US2020/019274, International Preliminary Report on Patentability mailed Sep. 2, 2021", 9 pgs.
"International Application Serial No. PCT/US2020/019274, International Search Report mailed Jun. 26, 2020", 6 pgs.
"International Application Serial No. PCT/US2020/019274, Written Opinion mailed Jun. 26, 2020", 7 pgs.
"Japanese Application Serial No. 2021-549230, Voluntary Amendment filed Feb. 2, 2023", w/ English Claims, 27 pgs.
"Japanese Application Serial No. 2015-539651, Examiners Decision of Final Refusal mailed Nov. 21, 2017", w/ English Translation, 13 pgs.
"Japanese Application Serial No. 2015-539651, Office Action mailed May 15, 2018", w/English Translation, 15 pgs.
"Japanese Application Serial No. 2015-539651, Office Action mailed Jul. 11, 2017", w/English Translation, 10 pgs.
"Japanese Application Serial No. 2015-539651, Response filed Mar. 20, 2018 to Examiners Decision of Final Refusal mailed Nov. 21, 2017", w/ English Claims, 34 pgs.
"Japanese Application Serial No. 2015-539651, Response filed Sep. 6, 2017 to Office Action mailed Jul. 11, 2017", w/ English claims, 15 pgs.
"Japanese Application Serial No. 2017-555548, Examiners Decision of Final Refusal mailed Mar. 26, 2019", w/ English translation, 5 pgs.
"Japanese Application Serial No. 2017-555548, Office Action mailed Aug. 21, 2018", w/ English translation, 8 pgs.
"Japanese Application Serial No. 2017-555548, Office Action mailed Aug. 25, 2020", w/ English translation, 22 pgs.
"Japanese Application Serial No. 2017-555548, Office Action mailed Sep. 10, 2019", w/English Translation, 2 pgs.
"Japanese Application Serial No. 2017-555548, Respone filed Jul. 26, 2019 to Examiners Decision of Final Refusal mailed Mar. 26, 2019", w/English Claims, 19 pgs.
"Japanese Application Serial No. 2017-555548, Response filed Nov. 20, 2018 to Office Action mailed Aug. 21, 2018", w/English Claims, 11 pgs.
"Japanese Application Serial No. 2018-052874, Office Action mailed Jan. 29, 2019", w/ English translation, 15 pgs.
"Japanese Application Serial No. 2018-052874, Office Action mailed Oct. 1, 2019", w/ English translation, 6 pgs.
"Japanese Application Serial No. 2018-052874, Response filed May 14, 2019 to Office Action mailed Jan. 29, 2019", w/English Claims, 24 pgs.
"Japanese Application Serial No. 2018-563611, Notification of Reasons for Refusal mailed Apr. 23, 2019", w/ English translation, 7 pgs.
"Japanese Application Serial No. 2018-563611, Notification of Reasons for Refusal mailed Aug. 20, 2019", w/ English translation, 7 pgs.
"Japanese Application Serial No. 2018-563611, Response filed Jul. 22, 2019 to Notification of Reasons for Refusal mailed Apr. 23, 2019", w/English Claims, 14 pgs.
"Japanese Application Serial No. 2019-137680, Notification of Reasons for Rejection mailed Jul. 21, 2020", W/English Translation, 5 pgs.
"Japanese Application Serial No. 2019-137680, Response filed Oct. 6, 2020 to Notification of Reasons for Rejection mailed Jul. 21, 2020", w/ English Translation, 5 pgs.
"Japanese Application Serial No. 2019-229554, Notification of Reasons for Refusal mailed Jan. 10, 2023", w/ English Translation, 5 pgs.

(56) References Cited

OTHER PUBLICATIONS

"Japanese Application Serial No. 2019-229554, Notification of Reasons for Refusal mailed May 31, 2022", w/ English Translation, 8 pgs.
"Japanese Application Serial No. 2019-229554, Response filed Mar. 28, 2023 to Notification of Reasons for Refusal mailed Jan. 10, 2023", w/ English Claims, 7 pgs.
"Japanese Application Serial No. 2019-229554, Response filed Aug. 26, 2022 to Notification of Reasons for Refusal mailed May 31, 2022", w/ English Claims, 8 pgs.
"Japanese Application Serial No. 2020-015071, Examiners Decision of Final Refusal mailed May 11, 2021", w/ English Translation, 5 pgs.
"Japanese Application Serial No. 2020-015071, Notification of Reasons for Refusal mailed Jan. 12, 2021", w/ English translation, 8 pgs.
"Japanese Application Serial No. 2020-015071, Notification of Reasons for Refusal mailed Feb. 28, 2023", w/ English translation, 27 pgs.
"Japanese Application Serial No. 2020-015071, Preliminary Examination Report mailed Dec. 21, 2021", w/ English translation, 2 pgs.
"Japanese Application Serial No. 2020-015071, Response Filed Mar. 18, 2022 to Preliminary Examination Report mailed Dec. 21, 2021", W/ English Translation, 16 pgs.
"Japanese Application Serial No. 2021-006798, Notification of Reasons for Refusal mailed Feb. 15, 2022", w/ English Translation, 8 pgs.
"Lactic Acid", ChemSpider, Accessed online on Mar. 13, 2021 at <https://www.chemspider.com/search.aspx?q=lactic+acid>, (2021), 2 pgs.
"Lactobionic Acid", ChemSpider, Accessed online on Mar. 13, 2021 at <https://www.chemspider.com/Chemical-Structure.7040,html>. (Year: 2021), (2021), 3 pgs.
"Meglumine", ChemSpider, Accessed online on Mar. 13, 2021 at <https://www.chemspider.com/Chemical-Structure.8249.html>, (2021), 3 pgs.
"Pentaerythritol ethoxylate (15/4 EO/OH) Sigma-Aldrich", Sigma-Aldrich, Accessed online on Mar. 13, 2021 at <https://www.sigmaaldrich.com/catalog/product/aldrich/418730?lang=en&region=US>. (Year: 2021), (2021), 2 pgs.
"Pentaerythritol ethoxylate (3/4 EO/OH)", Sigma-Aldrich, Accessed online on Mar. 13, 2021 at <https://www.sigmaaldrich.com/catalog/product/aldrich/416150?lang=en&region=US>. (Year: 2021), (2021), 2 pgs.
"PMA P130024: FDA Summary of Safety and Effectiveness Data (SSED)", Retrieved from the Internet: <URL:https://www.accessdata.fda.gov/cdrh_docs/pdf13/P130024b.pdf>, 44 pgs.
"Stricture", definition accessed online on Jun. 10, 2019, [Online] Retrieved from the internet: <www.merriam-webster.com/dictionary/stricture>, (2019), 1 pg.
"TWEEN 20", Sigma-Aldrich, Accessed online on Mar. 13, 2021 at <https://www.sigmaaldrich.com/catalog/product/sigma/p9416?lang=en&region=US>. (Year: 2021), (2021), 1 pg.
"U.S. Appl. No. 16/135,472, filed May 15, 2020 Declaration. (Year: 2020)", 15 pgs.
"U.S. Appl. No. 15/568,614, filed Jul. 14, 2020 declaration. (Year: 2020)", 4 pgs.
Aaron, Latayia, et al., "Review of Prostate Anatomy and Embryology and the Etiology of BPH", Urol Clin North Am 43(3), (Aug. 2016), pp. 279-288.
Daughtry, et al., "Balloon Dilation of the Ureter: A Means to Facilitate Passage of Ureteral and Renal Calculi", The Journal of Urology, vol. 136, (1986), 1063-1065.
Daughtry, et al., "Balloon dilation of urethral strictures", Urology, vol. 31, (1988), 231-233.
Donatucci, Craig F, et al., "Randomized Clinical Trial Comparing Balloon Dilatation to Transurethral Resection of Prostate for Benign Prostatic Hyperplasia", Adult Urology vol. 4 2, No. 1, (Jul. 1993), 42-49.

Goldenberg, S L, "Balloon Dilatation of the Prostate", Alternate Methods in the Treatment of Benign Prostatic Hyperplasia, (1993), 97-119.
Huang, Weigua, et al., "Effect of transurethral split of the prostate using a double-columnar balloon catheter for benign prostatic hyperplasia", Medicine 95:40, (Mar. 1, 2016), 4 pgs.
Lukacs, B, et al., "One-year follow-up of 2829 patients with moderate to severe lower urinary tract symptoms treated with alt uzosin in general practice according to IPSS and a health-related quality-of-life questionnaire", BPM Group in General Practice, Urology; 55(4), (2000), 7 pgs.
Milonas, Daimantas, et al., "The effect of complete transurethral resection of the prostate on symptoms, quality of life, and voiding function improvement", Central European Journal of Urology, (2015), pp. 169-174.
Oesterling, Joseph E, "The Origin and Development of Benign Prostatic Hyperplasia An Age-Dependent Process", Journal of Andrology, vol. 12, No. 6,, (1991), 8 pgs.
Roehrborn, C G, "Pathology of benign prostatic hyperplasia", International Journal of Impotence Research 20, (2008), S11-S18.
Shiel Jr, William C, "Definition of stricture", [Online] Retrieved from the internet: <https://www.medicinenet.com/script/main/art.asp?articlekey= 166621>, (2019), 1 pg.
Shin, et al., "Tissue Hyperplasia: Influence of a Paclitaxel-eluting Covered Stent-Preliminary Study in a Canine Urethral Model", Radiology, (2005), 438-444.
Vale, J A, et al., "Balloon dilatation of the prostate-should it have a place in the urologist's armamentarium?", Journal of the Royal Society of Medicine vol. 86, (Feb. 1993), pp. 83-86.
Van Loenhout, Rhiannon, et al., "Prostate Cancer—PI-RADS v2", https://radiologyassistant.nl/abdomen/prostate-cancer-pi-rads-v2 Accessed on May 14, 2020, (Aug. 1, 2018), 19 pgs.
Yazdani, Saami K, et al., "Vascular, Downstream, and Pharmacokinetic Responses to Treatment with a Low Dose Drug-Coated Balloon in a Swine Femoral Artery Model", Catheterization and Cardiovascular Interventions 83: 132-140, (2014), 132-140.
"U.S. Appl. No. 17/255,701, Corrected Notice of Allowability mailed Feb. 28, 2024", 11 pgs.
"U.S. Appl. No. 17/255,701, Notice of Allowance mailed Feb. 20, 2024", 12 pgs.
"U.S. Appl. No. 17/255,701, Response filed Jan. 25, 2024 to Non Final Office Action mailed Nov. 29, 2023", 20 pgs.
"U.S. Appl. No. 17/843,150, Non Final Office Action mailed Feb. 15, 2024", 12 pgs.
"U.S. Appl. No. 18/098,370, Corrected Notice of Allowability mailed Dec. 26, 2023", 6 pgs.
"Chinese Application Serial No. 202080030597.8, Office Action mailed Mar. 23, 2024", W/English Translation, 18 pgs.
"Chinese Application Serial No. 202080030597.8, Response filed Dec. 12, 2023 to Office Action mailed Jul. 29, 2023", w/ english claims, 14 pgs.
"European Application Serial No. 20712766.3, Communication Pursuant to Article 94(3) EPC mailed Apr. 23, 2024", 3 pgs.
"European Application Serial No. 23166049.9, Response filed Mar. 26, 2024 to Extended European Search Report mailed Aug. 28, 2023", 7 pgs.
"European Application Serial No. 23166193.5, Response filed Mar. 26, 2024 to Extended European Search Report mailed Oct. 4, 2023", 4 pgs.
"Japanese Application Serial No. 2021-549230, Response filed Feb. 1, 2024 to Notification of Reasons for Refusal mailed Nov. 28, 2023", w/ English Claims, 8 pgs.
"Japanese Application Serial No. 2023-014484, Decision of Rejection mailed Mar. 12, 2024", w/ English Translation, 4 pgs.
"Japanese Application Serial No. 2023-014484, Response filed Feb. 15, 2024 to Non-Final Office Action mailed on Dec. 5, 2023", w/English Translation, 6 pgs.
"U.S. Appl. No. 17/843,150, Response filed May 9, 2024 to Non Final Office Action mailed Feb. 15, 2024", 8 pgs.
"Chinese Application Serial No. 202410618448.3, Office Action mailed May 17, 2024", w o English translation, 1 page.

(56) References Cited

OTHER PUBLICATIONS

"Japanese Application Serial No. 2021-549230, Examiners Decision of Final Refusal mailed May 21, 2024", w English translation, 3 pgs.
"U.S. Appl. No. 18/379,505, Non Final Office Action mailed May 23, 2024", 6 pgs.
"Chinese Application Serial No. 202080030597.8, Response filed May 22, 2024 to Office Action mailed Mar. 23, 2024", w current English claims, 15 pgs.

* cited by examiner

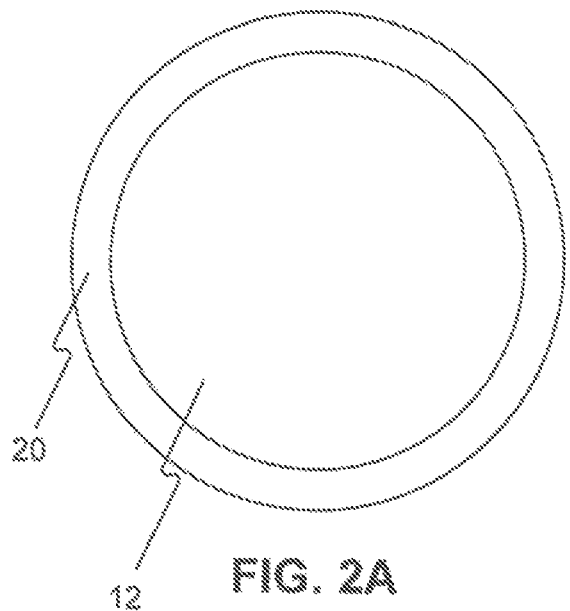
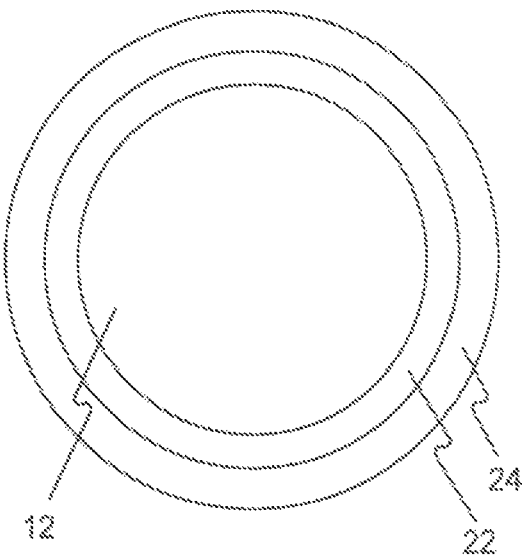
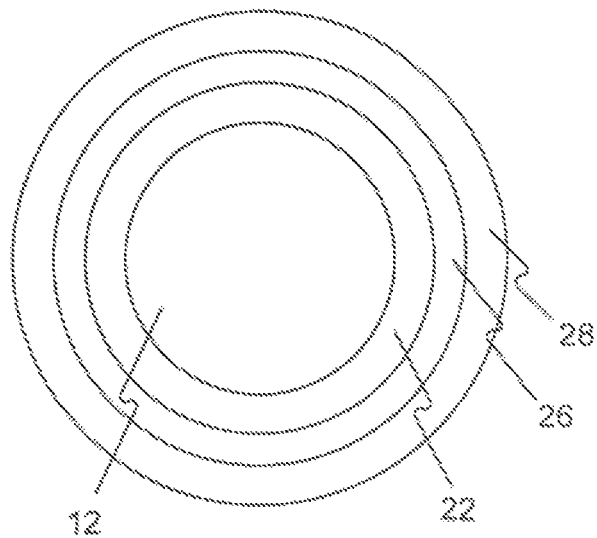

DRUG COATED BALLOON CATHETERS FOR NONVASCULAR STRICTURES

CROSS-REFERENCE TO RELATED APPLICATION

This application is a continuation of U.S. patent application Ser. No. 18/097,690, filed Jan. 17, 2023, which is a continuation of U.S. patent application Ser. No. 17/951,321, filed Sep. 23, 2022, which is a a continuation of U.S. patent application Ser. No. 17/107,136, filed Nov. 30, 2020, which is a a continuation of U.S. patent application Ser. No. 15/568,614, filed Oct. 23, 2017, which is a U.S. National Stage Application under 35 U.S.C. 371 from International Application No. PCT/US2016/028652, filed Apr. 21, 2016, which claims the benefit of priority to U.S. Provisional Patent Application Ser. No. 62/152,559 filed Apr. 24, 2015, the disclosures of which are incorporated herein in their entirety by reference.

BACKGROUND

Benign prostatic hyperplasia is a non-cancerous enlargement of the prostate gland, affecting more than 50% percent of men over the age of 60. The prostate early in life is the size and shape of a walnut and weight about 20 grams. Prostate enlargement appears to be a normal process. With age, the prostate gradually increases in size to twice or more its normal size. As the prostate grows, it presses against and narrows the urethra, causing a urinary obstruction that makes it difficult to urinate.

Male urethral stricture disease occurred at a rate as high as 0.6% in some populations. Urethral stricture diseases appeared to be more common in the elderly population. The patients with the strictures experience moderate complications, such as bother from lower urinary tract voiding symptoms, recurrent urinary tract infection and the need for repeat urethral procedures such as dilation or urethrotomy.

Ureteral strictures of upper urinary tract are either congenital or acquired. Congenital ureteral strictures are most commonly located at the ureteropelvic junction. Most of ureteral strictures are acquired and usually are iatrogenic. The most common etiology of the ureteral strictures is injury during endoscopic, open, or laparoscopic surgical procedures.

Esophageal strictures are a problem commonly encountered in gastroenterological medicine and can be caused by malignant or benign lesions. Dysphagia is the symptom experienced by all patients. Most of these patients require palliative treatment to relieve the dysphagia.

Chronic obstructive pulmonary disease (COPD) is a term used to classify two major airflow obstruction disorders: chronic bronchitis and emphysema. Approximately 16 million Americans have COPD, 80-90% of them were smokers throughout much of their lives. COPD is a leading cause of death in the U.S. Chronic bronchitis is inflammation of the bronchial airways. The bronchial airways connect the trachea with the lungs. When inflamed, the bronchial tubes secrete mucus, causing a chronic cough. Emphysema is an overinflation of the alveoli, or air sacs in the lungs. This condition causes shortness of breath.

Asthma is a chronic respiratory disease characterized by inflammation of the airways, excess mucus production and airway hyper responsiveness, and a condition in which airways narrow excessively or too easily respond to a stimulus. Asthma episodes or attacks cause narrowing of the airways, which make breathing difficult. Asthma attacks can have a significant impact on a patient's life, limiting participation in many activities. In severe cases, asthma attacks can be life threatening. Presently, there is no known cure for asthma.

Chronic sinusitis is an inflammation of the membrane lining of one or more paranasal sinuses. Chronic sinusitis lasts longer than three weeks and often continues for months. In cases of chronic sinusitis, there is usually tissue damage. According to the Center for Disease Control (CDC), thirty seven million cases of chronic sinusitis are reported annually.

SUMMARY OF THE INVENTION

One aspect of the invention is to deliver paclitaxel, rapamycin, or their analogues, to the wall of a body lumen to treat the narrowing or stricture.

The antimicrobial properties of various fatty acids and monoglycerides of C8-C12 fatty acids have been investigated for many years. The studies have confirmed that both fatty acids and monoglycerides are capable of inhibiting the growth of numerous types of bacteria and viruses. In one embodiment, the coating formulation includes various fatty acids and monoglycerides of C8-C12 fatty acids, such as caprylic acid, monocaprilin, capric acid, monocaprin, lauric acid and monolaurin, as one of the additives for the treatment of various diseases.

The causes of nonvascular diseases of benign prostatic hyperplasia (BPH) strictures, urethral strictures, ureteral strictures, prostate cancer, esophageal strictures, biliary tract strictures, asthma and chronic obstructive pulmonary disease (COPD) are infections and inflammations by bacteria and viruses. It is beneficial to have a coating formulation of drugs and additives which have the properties of killing and inhibition of the bacteria and viruses.

The present invention provides new methods for treatments of nonvascular diseases of benign prostatic hyperplasia (BPH) strictures, urethral strictures, ureteral strictures, prostate cancer, esophageal strictures, biliary tract strictures, asthma and chronic obstructive pulmonary disease (COPD) to have a long term and persistent effect. The new methods will prevent renarrowing and recurrent strictures. The methods involve delivering of anti-inflammatory and anti-proliferate drugs (e.g., rapamycin, paclitaxel, or their analogues) and one or more water-soluble additives to a target tissue. Embodiments of the present invention provide a medical device coating formulation including a drug for treatment of the strictures in nonvascular body lumens, and additives that enhance absorption of the drug into tissue of body lumens and have a property of antibacterial and viruses.

Embodiments of the present disclosure are directed to the treatment of strictures in nonvascular body lumens by delivering of an effective amount of anti-inflammatory and anti-proliferate drugs (e.g., rapamycin, paclitaxel, or their analogues) to a target tissue. The strictures in nonvascular body lumens include urethral strictures, ureteral strictures, esophageal strictures, sinus strictures, and biliary tract strictures. Embodiments of the present disclosure are directed to methods for treating at least one of benign prostatic hyperplasia (BPH), narrowing urethral, prostate cancer, asthma, and chronic obstructive pulmonary disease (COPD). The treatment is intended for a variety of animals, such as premature neonates to adult humans.

By coating the exterior surface of a medical device, and particularly of a balloon catheter or a stent, for example, with a layer including a therapeutic agent and additives that have a hydrophilic part and a drug affinity part, it is useful in solving the problems associated with the coatings discussed above. The drug affinity part is a hydrophobic part and/or has an affinity to the therapeutic agent by hydrogen bonding and/or van der Waals interactions. Surprisingly, additives according to embodiments of the present invention, which include a hydrophilic part and a drug affinity part, in combination with a therapeutic agent, forms an effective drug delivery coating on a medical device without the use of oils and lipids, thereby avoiding the lipolysis dependence and other disadvantages of conventional oil-based coating formulations. Moreover, the additives according to embodiments of the present invention facilitate rapid drug elution and superior permeation of drug into tissues at a disease site. Thus, coatings according to embodiments of the present invention provide an enhanced rate and/or extent of absorption of the hydrophobic therapeutic agent in nonvascular diseased tissues or nonvascular body lumens. In embodiments of the present invention, the coated device delivers therapeutic agent to nonvascular tissues during a very brief deployment time of less than 10 minutes, less than 2 minutes, and reduces renarrowing and reoccurring of the strictures of a nonvascular body lumen.

In one embodiment, the present invention relates to a medical device for delivering a therapeutic agent to a nonvascular tissue or nonvascular body lumen, the device including a layer overlying an exterior surface of the medical device. The device includes one of a balloon catheter, a perfusion balloon catheter, an infusion catheter such as distal perforated drug infusion tube, a perforated balloon, spaced double balloon, porous balloon, and weeping balloon, a cutting balloon catheter, a scoring balloon catheter. Further, the nonvascular tissue includes tissue of one of esophagus, airways, sinus, trachea, colon, biliary tract, urinary tract, prostate, urethral, ureteral, and other nonvascular lumens. The balloon catheters have a polyether-amide block copolymers as shafts and balloon materials.

In one embodiment of the medical devices, the additive enhances absorption of the drug into nonvascular tissue of the body lumens. The nonvascular body lumens include esophagus, airways, sinus, trachea, colon, biliary tract, urinary tract, prostate, urethral, ureteral, and other nonvascular lumens. In another embodiment of the medical devices, the additive includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions. In one embodiment, the drug is not enclosed in micelles or encapsulated in polymer particles.

In one embodiment of the medical devices, the additive is at least one of a surfactant and a chemical compound. In one embodiment, the chemical compound is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters, and derivatives thereof. In another embodiment, the chemical compound has one or more hydroxyl, amino, carbonyl, carboxyl, acid, amide or ester groups. In another embodiment, the chemical compound having one or more hydroxyl, amino, carbonyl, carboxyl, acid, amide or ester groups is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules.

In one embodiment of the medical devices, a coating layer overlying the exterior of the medical device includes one or more water-soluble additives. In one embodiment, the water-soluble additive is chosen from p-isononylphenoxy-polyglycidol, PEG laurate, Tween 20, Tween 40, Tween 60, Tween 80, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-p-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid, cetotiamine, cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl) urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, N-acetylglucosamine, N-octyl-D-gluconamide, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-Lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate (e.g., Labrasol®), PEG caprate, PEG caproate, glyceryl monocaprylate, glyceryl monocaprate, glyceryl monocaproate, monolaurin, monocaprin, monocaprylin, monomyristin, monopalmitolein, monoolein, derivatives thereof, and combinations thereof.

In one embodiment, the one or more water-soluble additives are chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, caffeine, allantoin, (2-hydroxyethyl)urea, N,N'-bis(hydroxymethyl)urea, and combinations thereof.

In one embodiment of the medical devices, a coating layer overlying the exterior of the medical device includes one or more water-soluble additives (e.g., a water-soluble first additive, a water-soluble second additive, and a water-soluble third additive). In one embodiment, the one or more water-soluble additives are chosen from creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, N-acetylglucosamine, N-octyl-D-gluconamide, C6-ceramide, dihydro-C6-ceramide, cerabroside, sphingo-myelin, galaclocerebrosides, lactocerebrosides, N-acetyl-D-sphingosine, N-hexanoyl-D-sphingosine, N-octonoyl-D-sphingosine, N-Lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate (e.g., Labrasol®), PEG caprate, PEG caproate, glyceryl monocaprylate, glyceryl monocaprate, glyceryl monocaproate, monolaurin, monocaprin, monocaprylin, monomyristin, monopalmitolein, and monoolein.

In one embodiment, the surfactant is chosen from PEG-fatty acids and PEG-fatty acid mono and diesters, polyethylene glycol glycerol fatty acid esters, alcohol-oil transesterification products, polyglyceryl fatty acids, propylene glycol fatty acid esters, sterols and derivatives thereof, polyethylene glycol sorbitan fatty acid esters, polyethylene glycol alkyl ethers, polyethylene glycol alkyl phenols, polyoxyethylene-polyoxypropylene block copolymers, and sorbitan fatty acid esters. In another embodiment, the surfactant is chosen from esters of lauric acid, oleic acid, and stearic acid, PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate, PEG-20 oleate, PEG-20 dilaurate, PEG-20 dioleate, PEG-20 distearate, PEG-32 dilaurate, PEG-32 dioleate, PEG-25 trioleate, PEG-60 corn glycerides, PEG-60 almond oil, PEG-40 palm kernel oil, PEG-8 caprylic/capric glycerides, and PEG-6 caprylic/capric glycerides, PEG-6 corn oil, PEG-6 almond oil, PEG-6 apricot kernel oil, PEG-6 olive oil, PEG-6 peanut oil, PEG-6 hydrogenated palm kernel oil, PEG-6 palm kernel oil, PEG-6 triolein, PEG-8 corn oil, PEG-20 corn glycerides, PEG-20 almond glycerides, polyglyceryl oleate, polyglyceryl-2 dioleate, polyglyceryl-10 trioleate, polyglyceryl stearate, polyglyceryl laurate, polyglyceryl myristate, polyglyceryl palmitate, and polyglyceryl linoleate, polyglyceryl-10 laurate, polyglyceryl-10 oleate, polyglyceryl-10 mono, dioleate, polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate, polyglyceryl polyricinoleate, propylene glycol monolaurate, propylene glycol ricinoleate, propylene glycol monooleate, propylene glycol dicaprylate/dicaprate, propylene glycol dioctanoate, PEG-20 sorbitan monolaurate, PEG-20 sorbitan monopalmitate, PEG-20 sorbitan monostearate, PEG-20 sorbitan monooleate, PEG-10-100 nonyl phenol, PEG-15-100 octyl phenol ether, Tyloxapol, octoxynol, nonoxynol, sucrose monopalmitate, sucrose monolaurate, decanoyl-N-methylglucamide, n-decyl-β-D-glucopyranoside, n-decyl-β-D-maltopyranoside, n-dodecyl-p-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-β-D-thioglucopyranoside, sorbitan monolaurate, sorbitan monopalmitate, sorbitan monooleate, sorbitan monostearate, benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylesters of sodium sulfonsuccinic acid, sodium dioctyl sulfosuccinate, sodium cholate, sodium taurocholate, and derivatives thereof.

In one embodiment, the additive is chosen from PEG fatty esters and alcohols, glycerol fatty esters, sorbitan fatty esters, PEG glyceryl fatty esters, PEG sorbitan fatty esters, sugar fatty esters, PEG sugar esters, vitamins and derivatives, aminoacids, multiaminoacids and derivatives, peptides, polypeptides, proteins, quaternary ammonium salts, organic acids, salts and anhydrides. In another embodiment, the additive in the coating layer overlying the surface of the balloon is chosen from p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-$3-D-glucopyranoside, octanoyl-N-methylglucamide, n-octyl-β-D-glucopyranoside, octyl-p-D-thioglucopyranoside; benzalkonium chloride, benzethonium chloride, docecyl trimethyl ammonium bromide, sodium docecylsulfates, dialkyl methylbenzyl ammonium chloride, and dialkylesters of sodium sulfonsuccinic acid (ionic surfactants), cystine, tyrosine, tryptophan, leucine, isoleucine, phenylalanine, asparagine, aspartic acid, glutamic acid, and methionine (amino acids); acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid (organic acids and anhydrides), cetotiamine, cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, L-ascorbic acid and its salt, D-glucoascorbic acid and its salt, triethanolamine, diethanolamine, meglumine, tromethamine, glucamine, glucosamine, glucoheptonic acid, glucomic acid, gluconolactone, D-glucoheptono-1,4-lactone, glucooctanoic lactone, gulonic acid lactone, mannoic lactone, erythronic acid lactone, ribonic acid lactone, glucosamine, glutamic acid, benzyl alcohol, benzoic acid, hydroxybenzoic acid, vanillin, vanillic acid, vanillic acid diethylamide, lysine acetate salt, gentisic acid, lactobionic acid, lactitol, acetaminophen, ibuprofen, catechin, catechin gallate, methyl paraben, ethyl paraben, propyl paraben, butyl paraben, tiletamine, ketamine, propofol, lactic acids, acetic acid, salts of any organic acid and amine above described, polyglycidol, glycerols and multiglycerols (chemical compounds with multiple hydroxyl, amino, carbonyl, carboxyl, or ester moieties).

In another embodiment, the medical device further includes a dimethylsulfoxide solvent layer, wherein the dimethylsulfoxide solvent layer is overlying the exterior surface of the medical device.

In one embodiment of the medical device, the device is capable of releasing the therapeutic agent and the additive and delivering therapeutic agent to the tissue in about 0.1 to 10 minutes. In one embodiment, the concentration of the therapeutic agent in the layer is from 1 to 20 μg/mm². In one embodiment, the concentration of the therapeutic agent in the layer is from 2 to 10 μg/mm². In one embodiment, the therapeutic agent is not water-soluble (e.g., hydrophobic).

In one embodiment, the additives enhance release of the therapeutic agent off the balloon. In another embodiment, the additive enhances penetration and absorption of the therapeutic agent in tissue. In another embodiment, the additive has a water and ethanol solubility of at least 1 mg/ml and the therapeutic agent is not water-soluble.

In another embodiment of the medical device, the layer overlying the exterior surface of the medical device includes a therapeutic agent and at least two additives, wherein each of the additives includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein each additive is soluble in polar organic solvent and is soluble in water. In one aspect of this embodiment, the polar organic solvent is chosen from methanol, ethanol, isopropanol, acetone, dimethylformide, tetrahydrofuran, methylethyl ketone, dimethylsulfoxide, acetonitrile, ethyl acetate, and chloroform and mixtures of these polar organic solvents with water. In another aspect of this embodiment, the device further includes a top layer overlying the surface of the layer overlying the exterior surface of the medical device to reduce loss of drug during transit through a body to the target tissue.

In another embodiment of the medical device, the layer overlying the exterior surface of the medical device includes a therapeutic agent and an additive, wherein the additive includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive reduces crystal size and number of particles of the therapeutic agent, and wherein the additive is water-soluble and the therapeutic agent is not water-soluble.

In another embodiment of the medical device, the layer overlying the exterior surface of the medical device includes a therapeutic agent and an additive, wherein the additive includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive has a fatty chain of an acid, ester, ether, or alcohol, wherein the fatty chain can directly insert into lipid membrane structures of the tissue, and wherein the therapeutic agent is not water-soluble.

In another embodiment of the medical device, the layer overlying the exterior surface of the medical device includes a therapeutic agent and an additive, wherein the additive includes a hydrophilic part and a hydrophobic part, wherein the additive can penetrate into and rearrange lipid membrane structures of the tissue, and wherein the therapeutic agent is not water-soluble. In some embodiments, the therapeutic agent is not enclosed in micelles or encapsulated in polymer particles.

In another embodiment of the medical device, the layer overlying the exterior surface of the medical device includes a therapeutic agent and an additive, wherein the additive includes a hydrophilic part and a drug affinity part, wherein the additive has a fatty chain of an acid, ester, ether, or alcohol, wherein the fatty chain directly inserts into lipid membrane structures of tissue, wherein the additive has one or more functional groups which have affinity to the drug by hydrogen bonding and/or van der Waals interactions (the functional groups include hydroxyl, ester, amide, carboxylic acid, primary, second, and tertiary amine, carbonyl, anhydrides, oxides, and amino alcohols), wherein the therapeutic agent is not water-soluble. In some embodiments, the therapeutic agent is not enclosed in micelles or encapsulated in polymer particles. In some embodiments, the layer does not include a polymer, and the layer does not include an iodine covalent bonded contrast agent.

In yet another embodiment, the present invention relates to a medical device coating for delivering a drug to a nonvascular tissue or nonvascular body lumen that is prepared from a mixture. In one aspect of this embodiment, the coating is prepared from a mixture including an organic phase containing drug particles dispersed therein and an aqueous phase containing a water-soluble additive. In one aspect of this embodiment, the water-soluble additive is chosen from polyethylene glycol, polyvinyl alcohol, polyvinylpyrrolidinone, polypeptides, water-soluble surfactants, water-soluble vitamins, and proteins. In another aspect of this embodiment, the preparation of the mixture includes homogenization under high shear conditions and optionally under pressure.

In another embodiment, the present invention relates to a balloon catheter for delivering a therapeutic agent to a nonvascular body lumen, the catheter including a coating layer overlying an exterior surface of a balloon. In one embodiment of the balloon catheter, the coating layer includes a therapeutic agent and an additive, wherein the additive includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is water-soluble, and wherein the additive is at least one of a surfactant and a chemical compound, and wherein the chemical compound has a molecular weight of from 50 to 750.

In another embodiment of the balloon catheter, the coating layer includes a therapeutic agent and an additive, wherein the additive includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is at least one of a surfactant and a chemical compound, and wherein the chemical compound has more than four hydroxyl groups. In one aspect of this embodiment, the chemical compound having more than four hydroxyl groups has a melting point of 120° C. or less, and the chemical compound is an alcohol or an ester.

In one embodiment of the balloon catheter, the coating layer overlying an exterior surface of the medical device consists essentially of the therapeutic agent and the additive. In another embodiment, the coating layer overlying an exterior surface of the medical device consists essentially of a therapeutic agent, a water-soluble first additive and a water-soluble second additive. In another embodiment, the coating overlying an exterior surface of the medical device consists essentially of a therapeutic agent, and one or more water-soluble additives (e.g., a water-soluble first additive, a water-soluble second additive, and a water-soluble third additive).

In another embodiment, the layer overlying the exterior surface of the medical device does not include an iodine covalent bonded contrast agent.

In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof. In one embodiment, the chemical compound has one or more hydroxyl, amino, carbonyl, carboxyl, acid, amide or ester groups. In one embodiment, the chemical compound having one or more hydroxyl, amino, carbonyl, carboxyl, acid, amide or ester groups is chosen from amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules.

In one embodiment of the balloon catheters, the additive is chosen from PEG-fatty acids and PEG-fatty acid mono and diesters, polyethylene glycol glycerol fatty acid esters, alcohol-oil transesterification products, polyglyceryl fatty acids, propylene glycol fatty acid esters, sterols and derivatives thereof, polyethylene glycol sorbitan fatty acid esters, polyethylene glycol alkyl ethers, sugars and derivatives thereof, polyethylene glycol alkyl phenols, polyoxyethylene-polyoxypropylene block copolymers, sorbitan fatty acid esters, fat-soluble vitamins and salts thereof, water-soluble vitamins and amphiphilic derivatives thereof, amino acid and salts thereof, oligopeptides, peptides and proteins, and organic acids and esters and anhydrides thereof.

In another embodiment of the balloon catheters, the additive is chosen from esters of lauric acid, oleic acid, and stearic acid, PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate, and PEG-20 oleate. In another embodiment, the additive is chosen from PEG-20 dilaurate, PEG-20 dioleate, PEG-20 distearate, PEG-32 dilaurate and PEG-32 dioleate. In another embodiment of the method, the additive is chosen from PEG-20 glyceryl laurate, PEG-30 glyceryl laurate, PEG-40 glyceryl laurate, PEG-20 glyceryl oleate, and PEG-30 glyceryl oleate. In another embodiment of the method, the additive is chosen from PEG-25 trioleate, PEG-60 corn glycerides, PEG-60 almond oil, PEG-40 palm kernel oil, PEG-8 caprylic/capric glycerides, and PEG-6 caprylic/capric glycerides, PEG-6 corn oil, PEG-6 almond oil, PEG-6 apricot kernel oil, PEG-6 olive oil, PEG-6 peanut oil, PEG-6 hydrogenated palm kernel oil, PEG-6 palm kernel oil, PEG-6 triolein, PEG-8 corn oil, PEG-20 corn glycerides, and PEG-20 almond glycerides.

In another embodiment of the balloon catheters, the additive is chosen from polyglyceryl oleate, polyglyceryl-2 dioleate, polyglyceryl-10 trioleate, polyglyceryl stearate, polyglyceryl laurate, polyglyceryl myristate, polyglyceryl palmitate, and polyglyceryl linoleate, polyglyceryl-10 laurate, polyglyceryl-10 oleate, polyglyceryl-10 mono, dioleate, polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate, and polyglyceryl polyricinoleate. In another embodiment of the method, the additive is chosen from propylene glycol monolaurate, propylene glycol ricinoleate, propylene glycol monooleate, propylene glycol dicaprylate/dicaprate, and propylene glycol dioctanoate. In another embodiment of the balloon catheters, the additive is PEG-24 cholesterol ether. In another embodiment of the balloon catheters, the additive is chosen from sterol polyethylene glycol derivatives.

In one embodiment, the present invention relates to a method for treating a stricture in a nonvascular body lumen including inserting a balloon catheter including a coating layer into an body stricture, wherein the stricture is one of urethral strictures, benign prostatic hyperplasia (BPH) strictures, ureteral strictures, esophageal strictures, sinus strictures, and biliary tract strictures, wherein the coating layer includes a drug and an additive, inflating the balloon catheter and releasing the drug to a wall of the stricture, deflating the balloon; and withdrawing the balloon catheter, wherein the residual drug is about 1 to 70% of the total loading drug on the balloon catheter. In one aspect of this embodiment, the additive enhances absorption of the drug into tissue of the nonvascular body lumen. In another embodiment of the method, the additive is chosen from PEG-20 sorbitan monolaurate, PEG-20 sorbitan monopalmitate, PEG-20 sorbitan monostearate, and PEG-20 sorbitan monooleate. In another embodiment of the method, the additive is chosen from PEG-3 oleyl ether and PEG-4 lauryl ether. In another embodiment of the method, the additive is chosen from sucrose monopalmitate, sucrose monolaurate, decanoyl-N-methylglucamide, n-decyl-p-D-glucopyranoside, n-decyl-p-D-maltopyranoside, n-dodecyl-β-D-glucopyranoside, n-dodecyl-p-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, and octyl-β-D-thioglucopyranoside.

In another embodiment of the method, the additive is chosen from PEG-10-100 nonyl phenol, PEG-15-100 octyl phenol ether, Tyloxapol, octoxynol, and nonoxynol. In another embodiment of the method, the additive is chosen from poloxamer 108, poloxamer 188, poloxamer 217, poloxamer 238, poloxamer 288, poloxamer 338, and poloxamer 407. In another embodiment of the method, the additive is chosen from poloxamer 124, poloxamer 182, poloxamer 183, poloxamer 212, poloxamer 331, and poloxamer 335. In another embodiment of the method, the additive is chosen from sorbitan monolaurate, sorbitan monopalmitate, sorbitan monooleate, and sorbitan monostearate. In another embodiment of the method, the additive is chosen from alpha-tocopherol, beta-tocopherol, gamma-tocopherol, delta-tocopherol, tocopherol acetate, ergosterol, 1-alpha-hydroxycholecal-ciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K-S(II), and folic acid.

In another embodiment of the method, the additive is chosen from acetiamine, benfotiamine, pantothenic acid, cetotiamine, cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U. In another embodiment of the method, the additive is chosen from alanine, arginine, asparagines, aspartic acid, cysteine, glutamic acid, glutamine, glycine, histidine, proline, isoleucine, leucine, lysine, methionine, phenylalanine, serine, threonine, tryptophan, tyrosine, and valine, and salts of any of the foregoing. In another embodiment of the method, the additive is albumin. In another embodiment of the method, the additive is chosen from n-octyl-β-D-glucopyranoside, octoxynol-9, Polysorbates, Tyloxapol, octoxynol, nonoxynol, isononylphenylpolyglycidol, PEG glyceryl monooleate, sorbitan monolaurate, sorbitan monopalmitate, sorbitan monooleate, sorbitan monostearate, polyglyceryl-10 oleate, polyglyceryl-10 laurate, polyglyceryl-10 palmitate, polyglyceryl-10 stearate, L-ascorbic acid, thiamine, maleic anhydride, niacinamide, and 2-pyrrolidone-5-carboxylic acid.

In another embodiment of the method, the additive is chosen from isononylphenylpolyglycidol, PEG glyceryl monooleate, sorbitan monolaurate, sorbitan monopalmitate, sorbitan monooleate, sorbitan monostearate, polyglyceryl-10 oleate, polyglyceryl-10 laurate, polyglyceryl-10 palmitate, and polyglyceryl-10 stearate. In another embodiment of the method, the additive is chosen from L-ascorbic acid, thiamine, maleic acids, niacinamide, and 2-pyrrolidone-5-carboxylic acid. In another embodiment of the method, the additive is chosen from Vitamin D2 and D3.

In one embodiment, the additive is at least one of a surfactant and a chemical compound. In one embodiment, the chemical compound is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters, and derivatives thereof. In one embodiment, the chemical compound has one or more hydroxyl, amino, carbonyl, carboxyl, acid, amide or ester groups. In one aspect of this embodiment, the chemical compound having one or more hydroxyl, amino, carbonyl, carboxyl, acid, amide or ester groups is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In one embodiment, the additive is chosen from p-isononylphenoxypolyglycidol, PEG laurate, Tween 20, Tween 40, Tween 60, Tween 80, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-β-D-thioglucopyranoside, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), and penta(propylene glycol), poly(propylene glycol) oligomers, a block copolymer of polyethylene glycol and polypropylene glycol, and derivatives and combinations thereof.

In one embodiment, the additive is chosen from PEG-fatty acids and PEG-fatty acid mono and diesters, polyethylene glycol glycerol fatty acid esters, alcohol-oil transesterification products, polyglyceryl fatty acids, propylene glycol fatty acid esters, sterol and derivatives thereof, polyethylene glycol sorbitan fatty acid esters, polyethylene glycol alkyl ethers, sugars and derivatives thereof, polyethylene glycol alkyl phenols, polyoxyethylene-polyoxypropylene block copolymers, sorbitan fatty acid esters, fat-soluble vitamins and salts thereof, water-soluble vitamins and amphiphilic derivatives thereof, amino acid and salts thereof, oligopeptides, peptides and proteins, and organic acids and esters and anhydrides thereof. In yet another aspect of this embodiment, the water insoluble drug is chosen from paclitaxel and analogues thereof and rapamycin and analogues thereof.

In one embodiment, the surfactant is chosen from esters of lauric acid, oleic acid, and stearic acid, PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate, PEG-20 oleate, PEG-20 dilaurate, PEG-20 dioleate, PEG-20 distearate, PEG-32 dilaurate, PEG-32 dioleate, PEG-20 glyceryl laurate, PEG-30 glyceryl laurate, PEG-40 glyceryl laurate, PEG-20 glyceryl oleate, PEG-30 glyceryl oleate, PEG-25 trioleate, PEG-60 corn glycerides, PEG-60 almond oil, PEG-40 palm kernel oil, PEG-8 caprylic/capric glycerides, PEG-6 caprylic/capric glycerides, PEG-6 corn oil, PEG-6 almond oil, PEG-6 apricot kernel oil, PEG-6 olive oil, PEG-6 peanut oil, PEG-6 hydrogenated palm kernel oil, PEG-6 palm kernel oil, PEG-6 triolein, PEG-8 corn oil, PEG-20 corn glycerides, PEG-20 almond glycerides, polyglyceryl oleate, polyglyceryl-2 dioleate, polyglyceryl-10 trioleate, polyglyceryl stearate, polyglyceryl laurate, polyglyceryl myristate, polyglyceryl palmitate, and polyglyceryl linoleate, polyglyceryl-10 laurate, polyglyceryl-10 oleate, polyglyceryl-10 mono, dioleate, polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate, and polyglyceryl polyricinoleate, propylene glycol monolaurate, propylene glycol ricinoleate, propylene glycol monooleate, propylene glycol dicaprylate/dicaprate, propylene glycol dioctanoate, PEG-20 sorbitan monolaurate, PEG-20 sorbitan monopalmitate, PEG-20 sorbitan monostearate, PEG-20 sorbitan monooleate, PEG-3 oleyl ether and PEG-4 lauryl ether, sucrose monopalmitate, sucrose monolaurate, decanoyl-N-methylglucamide, n-decyl-p-D-glucopyranoside, n-decyl-p-D-maltopyranoside, n-dodecyl-p-D-glucopyranoside, n-dodecyl-β-D-maltoside, heptanoyl-N-methylglucamide, n-heptyl-β-D-glucopyranoside, n-heptyl-p-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-β-D-thioglucopyranoside, PEG-10-100 nonyl phenol, PEG-15-100 octyl phenol ether, Tyloxapol, octoxynol, nonoxynol, sorbitan monolaurate, sorbitan monopalmitate, sorbitan monooleate, sorbitan monostearate, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid (ionic surfactants), n-octyl-β-D-glucopyranoside, octoxynol-9, Polysorbates, Tyloxapol, octoxynol, nonoxynol, isononylphenylpolyglycidol, PEG glyceryl monooleate, sorbitan monolaurate, sorbitan monopalmitate, sorbitan monooleate, sorbitan monostearate, polyglyceryl-10 oleate, polyglyceryl-10 laurate, polyglyceryl-10 palmitate, polyglyceryl-10 stearate, and their derivatives.

In one embodiment, the water insoluble drug is chosen from paclitaxel and analogues thereof and rapamycin and analogues thereof.

In one embodiment, some drugs that are considered particularly suitable for the airway, sinus and other nasal lumens are corticosteroids such as, budesonide, flunisolide, triamcinolone, beclomethasone, fluticasone, mometasone, mometasone furoate, dexamethasone, hydrocortisone, methylprednisolone, prednisone, cortisone, betamethasone, triamcinolone acetonide, or the like.

In one embodiment, the present invention relates to a method for treating a nonvascular body lumen including inserting a balloon catheter including a coating layer into an body lumen, wherein the body lumen is one of esophagus, airways, sinus, trachea, colon, biliary tract, urinary tract, prostate, urethral, ureteral, and other nonvascular lumens, wherein the coating layer includes a drug and an additive, inflating the balloon catheter and releasing the drug to a wall of the body lumen, deflating the balloon; and withdrawing the balloon catheter. In another embodiment, the present invention relates to a method for treating a stricture in a nonvascular body lumen including flushing the lumen with water, saline solution, or water solutions of the additives described above, inserting a balloon catheter including a coating layer into an body lumen, wherein the body lumen is one of esophagus, airways, sinus, trachea, colon, biliary tract, urinary tract, prostate, urethral, ureteral, and other nonvascular lumens, wherein the coating layer includes a drug and an additive, inflating the balloon catheter and releasing the drug to a wall of the body lumen, deflating the balloon, and withdrawing the balloon catheter. In another embodiment, the present invention relates to a method for treating a stricture in a nonvascular body lumen including infusing water, saline solution, or a water solution including at least one of the additives described above, inserting a balloon catheter including a coating layer into a stricture in a nonvascular body lumen, wherein the stricture in the nonvascular body lumen is one of, urethral strictures, ureteral strictures, esophageal strictures, sinus strictures, and biliary tract strictures, wherein the coating layer includes a drug and an additive, inflating the balloon catheter and releasing the drug to a wall of the stricture in a nonvascular body lumen, deflating the balloon, flushing the lumen with water or saline solution, and withdrawing the balloon catheter. In one aspect of this embodiment, the additive enhances absorption of the drug into tissue of the nonvascular body lumens. In another aspect of this embodiment, the additive includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions. In another aspect of this embodiment, the drug is not enclosed in micelles or encapsulated in polymer particles. In another aspect of this embodiment, the coating layer does not include oil, a lipid, or a polymer. In another aspect of this embodiment, the coating layer does not include a purely hydrophobic additive. In another aspect of this embodiment, the drug is chosen from paclitaxel and analogues thereof and rapamycin and analogues thereof. In another aspect of this embodiment, the additive is chosen from PEG-fatty acids and PEG-fatty acid mono and diesters, polyethylene glycol glycerol fatty acid esters, alcohol-oil transesterification products, polyglyceryl fatty acids, propylene glycol fatty acid esters, sterol and derivatives thereof, polyethylene glycol sorbitan fatty acid esters, polyethylene glycol alkyl ethers, sugars and derivatives thereof, polyethylene glycol alkyl phenols, polyoxyethylene-polyoxypropylene block copolymers, sorbitan fatty acid esters, fat-soluble vitamins and salts thereof, water-soluble vitamins and amphiphilic derivatives thereof, amino acid and salts thereof, oligopeptides, peptides and proteins, and organic acids and esters and anhydrides thereof. In yet another aspect of this embodiment, the drug can be released to the wall of the airway prior to, during, or after an asthma attack. In yet another aspect of this embodiment, the drug can be released to the wall of the esophagus. In yet another aspect of this embodiment, the drug can be released to the wall of the sinus. In yet another aspect of this embodiment, the drug can be released to the wall of the biliary tract. In yet another aspect of this embodiment, the drug can be released to the wall of the urinary tract, prostate, urethral, and ureteral lumens.

In one embodiment, the additive is at least one of a surfactant and a chemical compound. In one embodiment, the chemical compound is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters, and derivatives thereof.

In one embodiment, the chemical compound has one or more hydroxyl, amino, carbonyl, carboxyl, acid, amide or ester groups. In one aspect of this embodiment, the chemical compound having one or more hydroxyl, amino, carbonyl, carboxyl, acid, amide or ester groups is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules.

In one embodiment, the additive is chosen from p-isononylphenoxypolyglycidol, PEG laurate, Tween 20, Tween 40, Tween 60, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-p-D-glucopyranoside, n-decyl-p-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-β-D-thioglucopyranoside, cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid, cetotiamine, cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin. immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri (propylene glycol), tetra(propylene glycol, and penta(propylene glycol), poly(propylene glycol) oligomers, a block copolymer of polyethylene glycol and polypropylene glycol, and derivatives and combinations thereof.

It is understood that both the foregoing general description and the following detailed description are exemplary and explanatory only and are not restrictive of the present invention as claimed.

BRIEF DESCRIPTION OF THE DRAWINGS

FIGS. 2A-2C are cross-sectional views of different embodiments of the distal portion of the balloon catheter of FIG. 1, taken along line A-A, showing exemplary coating layers.

DETAILED DESCRIPTION OF THE INVENTION

Figure 1:
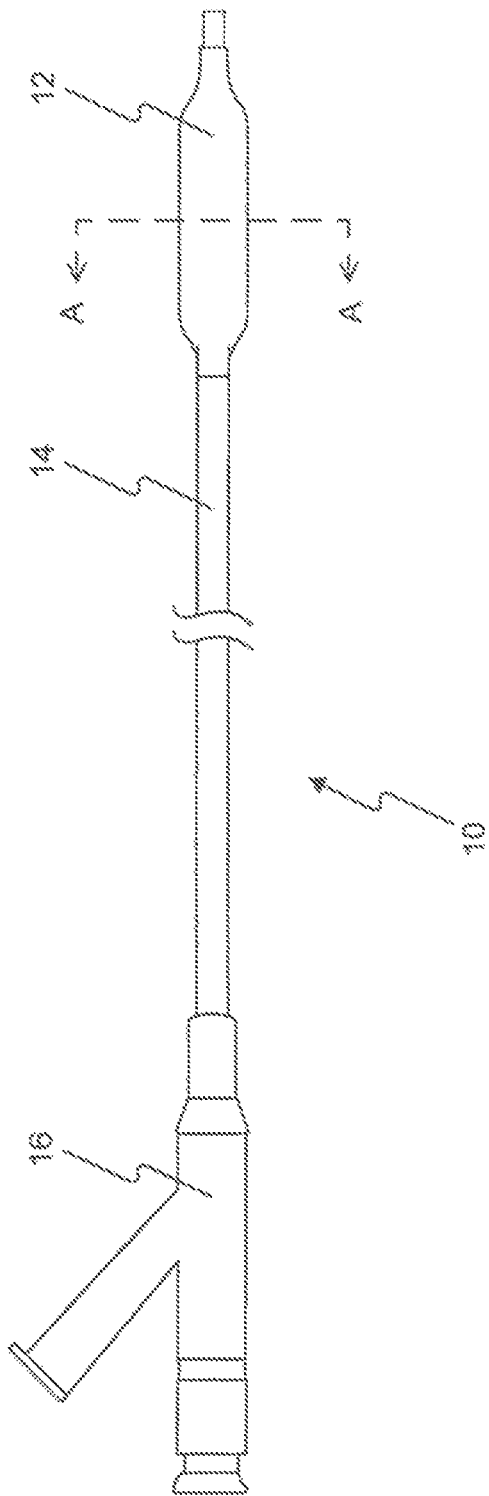
FIG. 1 is a perspective view of an exemplary embodiment of a balloon catheter according to the present invention.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," "or" "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

Embodiments of the present invention relate to medical devices, including particularly balloon catheters and stents, having a rapid drug-releasing coating and methods for preparing such coated devices. The therapeutic agent according to embodiments of the present invention does not require a delayed or long term release and instead, for example, the therapeutic agent and the additive are released in a very short time period to provide a therapeutic effect upon contact with tissue. An object of embodiments of the present invention is to facilitate rapid and efficient uptake of drug by target tissue during transitory device deployment at a target site.

As shown in FIG. 1, in one embodiment, the medical device is a balloon catheter. The balloon catheter may be any suitable catheter for the desired use, including conventional balloon catheters known to one of ordinary skill in the art. For example, balloon catheter 10 may include an expandable, inflatable balloon 12 at a distal end of the catheter 10, a handle assembly 16 at a proximal end of the catheter 10, and an elongate flexible member 14 extending between the proximal and distal ends. Handle assembly 16 may connect to and/or receive one or more suitable medical devices, such as a source of inflation media (e.g., air, saline, or contrast media). Flexible member 14 may be a tube made of suitable biocompatible material and having one or more lumens therein. At least one of the lumens is configured to receive inflation media and pass such media to balloon 12 for its expansion. The balloon catheter may be a rapid exchange or over-the-wire catheter and made of any suitable biocompatible material. The material of balloon 12 can include one or more of polyesters, polyamides, nylon 12, nylon 11, polyamide 12, block copolymers of polyether and polyamide, Pebax, polyurethanes, and block copolymers of polyether and polyester.

In one embodiment, the present invention provides a medical device for delivering a therapeutic agent to a tissue, such as a vascular tissue or a nonvascular tissue. The device includes a layer applied to an exterior surface of the medical device, such as a balloon catheter or stent, for example. The layer includes a therapeutic agent and one or more additives. The additive can be any suitable additive. The layer can include one additive, or the layer can include more than one additive, such as a water-soluble first additive and a water-soluble second additive. For example, as shown in the embodiment depicted in FIG. 2A, the balloon 12 is coated with a layer 20 that includes a therapeutic agent and an additive. In some embodiments, the layer consists essentially of a therapeutic agent and an additive, i.e., the layer includes only the therapeutic agent and the additive, without any other materially significant components. In some embodiments, the device may optionally include an adherent layer. For example, as shown in the embodiment depicted in FIG. 2B, the balloon 12 is coated with an adherent layer 22. A layer 24 that includes a therapeutic agent and an additive is overlying the adherent layer. The adherent layer, which is a separate layer underlying the drug coating layer, improves the adherence of the drug coating layer to the exterior surface of the medical device and protects coating integrity. For example, if drug and additive differ in their adherence to the medical device, the adherent layer may prevent differential loss of components and maintain drug-to-additive ratio in the coating during transit to a target site for therapeutic intervention. Furthermore, the adherent layer may function to facilitate rapid release of coating layer components off the device surface upon contact with tissues at the target site. In other embodiments, the device may include a top layer. The top layer may reduce loss of the drug layer before it is brought into contact with target tissues, for example during transit of the balloon 12 to the site of therapeutic intervention or during the first moments of inflation of balloon 12 before coating layer 20 is pressed into direct contact with target tissue.

Embodiments of the present invention are directed to the treatment of strictures in nonvascular body lumens by delivering of an effective amount of anti-inflammatory and anti-proliferate drugs (e.g., rapamycin, paclitaxel, or their analogues). The strictures in a nonvascular body lumen include urethral strictures, ureteral strictures, esophageal strictures, sinus strictures, and biliary tract strictures. Embodiments of the present invention are directed to methods for treating at least one of benign prostatic hyperplasia (BPH), prostate cancer, asthma, and chronic obstructive pulmonary disease (COPD). According to embodiments, the method involves delivering of anti-inflammatory and anti-proliferate drugs (e.g., rapamycin, paclitaxel, or their analogues) via coated medical devices, such as balloon catheters and stents. The anti-inflammatory and anti-proliferate drugs can be coated with the medical device alone or with one or more additives.

In one embodiment, the present invention relates to a method for treating a stricture in a nonvascular body lumen including inserting a balloon catheter including a coating layer into the stricture, wherein the stricture is one of urethral strictures, ureteral strictures, esophageal strictures, sinus strictures, and biliary tract strictures, wherein the coating layer includes a drug and an additive, inflating the balloon catheter and releasing the drug to a wall of the stricture, deflating the balloon; and withdrawing the balloon catheter, wherein the residual drug is about 1 to 70% of the total loading drug on the balloon catheter, wherein the drug in the wall of body lumen is about 0.1 to 25% of the total loading drug on the balloon catheter. In one aspect of this embodiment, the additive enhances absorption of the drug into tissue of the stricture in the nonvascular body lumen.

In one embodiment, the present invention relates to a method for treating a nonvascular body lumen including inserting a balloon catheter including a coating layer into an body lumen, wherein the body lumen is one of esophagus, airways, sinus, trachea, colon, biliary tract, urinary tract, prostate, urethral, ureteral, and other nonvascular lumens, wherein the coating layer includes a drug and an additive, inflating the balloon catheter and releasing the drug to a wall of the nonvascular body lumen, deflating the balloon; and withdrawing the balloon catheter, wherein the residual drug is about 1 to 70% of the total loading drug on the balloon catheter, wherein the drug in the wall of body lumen is about 0.1 to 25% of the total loading drug on the balloon catheter. In one aspect of this embodiment, the additive enhances absorption of the drug into tissue of the nonvascular body lumens. In another aspect of this embodiment, the additive includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions.

In one embodiment, the present invention relates to a balloon catheter for delivering a therapeutic agent to a target site of a nonvascular body lumen, the balloon catheter including a coating layer overlying an exterior surface of a balloon, wherein the coating layer includes an initial drug load of a hydrophobic therapeutic agent, and one or more water-soluble additive; the hydrophobic therapeutic agent is selected from the group consisting of paclitaxel, paclitaxel analogues, rapamycin, rapamycin analogues, and combinations thereof; the water-soluble additive is selected from the group consisting of N-acetylglucosamine, N-octyl-D-gluc%namide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof.

In some embodiments, the coating layer does not include one or more of an iodine covalent-bonded contrast agent, a dye, an oil, and a lipid. In some embodiments, the hydrophobic therapeutic agent is not enclosed in one or more of micelles and liposomes. In some embodiments, the hydrophobic therapeutic agent is not encapsulated in polymer particles. In some embodiments, the coating is free of one or more of micelles, liposomes, and polymer particles.

In one embodiment, the nonvascular body lumen is one of esophagus, airways, sinus, trachea, colon, biliary tract, urinary tract, prostate, urethral, ureteral, and other nonvascular lumens.

In one embodiment of the balloon catheter, the one or more water-soluble additives promote a rapid release of the hydrophobic therapeutic agent from the balloon, and whereby the rapid release includes a residual drug amount of the hydrophobic therapeutic agent remaining on the balloon after the balloon is inflated at the target site of the nonvascular body lumen for an inflation period of from about 0.1 minutes to 10 minutes and subsequently removed from the nonvascular lumen.

In one embodiment of the balloon catheter, the ratio by weight of the hydrophobic therapeutic agent in the coating layer to the total weight of the one or more additives in the coating layer is about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more. In one embodiment of the balloon catheter, the ratio by weight of the hydrophobic therapeutic agent in the coating layer to the total weight of the one or more water-soluble additives (e.g., a first and second water soluble additive in the coating layer, or to the total weight of a first, second, and third water soluble additive) in the coating layer, is from about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more.

In one embodiment of the balloon catheter, the initial drug load is from 1 microgram to 20 micrograms of the hydrophobic therapeutic agent per square millimeter of the balloon (i.e., per external surface area of the balloon), or about 2 to about 6 micrograms, or about 1 microgram or less, or less than, equal to, or greater than about 2, 3, 4, 5, 6, 7, 8, 9, 10, 12, 14, 16, 18, or about 20 micrograms or more. The residual drug amount can be 70% or less of the initial drug load.

In one embodiment, the present invention relates to a method for treating a stricture in a nonvascular body lumen, the method including flushing the nonvascular body lumen with water, saline solution, or a water solution including at least one water soluble additive; inserting a balloon catheter to a target site in the stricture in the nonvascular body lumen, the balloon catheter including a balloon and a coating layer overlying external surfaces of the balloon. The coating layer includes a at least one water-soluble additive, and an initial drug load of a hydrophobic therapeutic agent; the hydrophobic therapeutic agent is selected from the group consisting of paclitaxel, paclitaxel analogues, rapamycin, rapamycin analogues, and combinations thereof; the water-soluble additive is selected from the group consisting of N-acetylglucosamine, N-octyl-D-gluconamide, N-Nonanoyl-N-methylglycamine, N-octanoyl-N-methyl glutamine C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-Lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl) urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; inflating the balloon until the coating layer contacts walls of the stricture in the nonvascular body lumen at the target site for an inflation period; deflating the balloon after the inflation period, wherein the inflation period is from 0.1 minutes to 10 minutes; and withdrawing the balloon catheter from the stricture in the nonvascular body lumen. The inflated balloon catheter diameter can be such that the ratio of the balloon diameter to the nonvascular lumen diameter is about 1.01 to about 30, or about 1.2 to about 25, or about 1.5 to about 20, or about 1.01 or less, or less than, equal to, or greater than about 1.1, 1.2, 1.3, 1.4, 1.5, 1.6, 1.8, 2, 3, 4, 5, 6, 7, 8, 9, 10, 12, 14, 16, 18, 20, 22, 24, 26, 28, or about 30 or more.

In one embodiment of the method, the one or more water-soluble additives promote rapid release of the hydrophobic therapeutic agent from the balloon at the target site during an inflation period.

In one embodiment of the method, the balloon has thereon a residual drug amount after the withdrawing. Any suitable residual drug amount can remain after the withdrawing, such as greater than, equal to, or less than about 90 wt %, 88, 86, 84, 82, 80, 78, 76, 74, 72, 70, 68, 66, 64, 62, 60, 58, 56, 54, 52, 50, 48, 46, 44, 42, 40, 38, 36, 34, 32, 30, 28, 26, 24, 22, 20, 18, 16, 14, 12, 10, 8, 6, 4, 3, 2, 1 wt %, or about 0 wt %.

In one embodiment of the method, the stricture in the nonvascular body lumen is one of, urethral strictures, ureteral strictures, esophageal strictures, sinus strictures, and biliary tract strictures.

In one embodiment of the method, the ratio by weight of the therapeutic agent in the coating layer to the total weight of the one or more additives in the coating layer is about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more.

In one embodiment of the method, the initial drug load is from 1 microgram to 20 micrograms of the hydrophobic therapeutic agent per square millimeter of the balloon, or about 2 to about 6 micrograms, or about 1 microgram or less, or less than, equal to, or greater than about 2, 3, 4, 5, 6, 7, 8, 9, 10, 12, 14, 16, 18, or about 20 micrograms or more. The residual drug amount can be 70% or less of the initial drug load.

In one embodiment, the present invention relates to a method for treating at least one of a benign prostatic hyperplasia and prostate cancer, the method including flushing the prostate with water, saline solution, or a water solution including at least one water soluble additive; inserting a balloon catheter to a target site in the prostate, the balloon catheter including a balloon and a coating layer overlying external surfaces of the balloon. The coating layer can include one or more water-soluble additives, and an initial drug load of a hydrophobic therapeutic agent; the hydrophobic therapeutic agent is selected from the group consisting of paclitaxel, paclitaxel analogues, rapamycin, rapamycin analogues, and combinations thereof; the water-soluble additive is selected from the group consisting of N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; inflating the balloon until the coating layer contacts walls of the benign prostatic hyperplasia or prostate cancer at the target site for an inflation period; deflating the balloon after the inflation period, wherein the inflation period is from 0.1 minutes to 10 minutes; and withdrawing the balloon catheter from the prostate. The inflated balloon catheter diameter can be such that the ratio of the balloon diameter to the nonvascular lumen diameter is about 1.01 to about 30, or about 1.2 to about 25, or about 1.5 to about 20, or about 1.01 or less, or less than, equal to, or greater than about 1.1, 1.2, 1.3, 1.4, 1.5, 1.6, 1.8, 2, 3, 4, 5, 6, 7, 8, 9, 10, 12, 14, 16, 18, 20, 22, 24, 26, 28, or about 30 or more.

In one embodiment of the method, the one or more water-soluble additives promote rapid release of the hydrophobic therapeutic agent from the balloon at the target site during an inflation period.

In one embodiment of the method, the balloon has thereon a residual drug amount after the withdrawing.

In one embodiment of the method, the ratio by weight of the hydrophobic agent in the coating layer to the total weight of the one or more additives in the coating layer is about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more.

In one embodiment of the method, the initial drug load is from 1 microgram to 20 micrograms of the hydrophobic therapeutic agent per square millimeter of the balloon, or about 2 to about 6 micrograms, or about 1 microgram or less, or less than, equal to, or greater than about 2, 3, 4, 5, 6, 7, 8, 9, 10, 12, 14, 16, 18, or about 20 micrograms or more. The residual drug amount can be 70% or less of the initial drug load.

In one embodiment, the present invention relates to a method for treating a urethral stricture, the method including flushing the urethral stricture with water, saline solution, or a water solution including at least one water soluble additive; inserting a balloon catheter to a target site in the urethral stricture, the balloon catheter including a balloon and a coating layer overlying external surfaces of the balloon, wherein the coating layer includes at least one water-soluble additive, and an initial drug load of a hydrophobic therapeutic agent; the hydrophobic therapeutic agent is selected from the group consisting of paclitaxel, paclitaxel analogues, rapamycin, rapamycin analogues, and combinations thereof; the water-soluble additive is selected from the group consisting of N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the hydrophobic therapeutic agent in the coating layer to the total weight of the one or more water-soluble additives in the coating layer is from about 0.05 to 20; inflating the balloon until the coating layer contacts walls of the urethral stricture at the target site for an inflation period; deflating the balloon after the inflation period, wherein the inflation period is from 0.1 minutes to 10 minutes' and withdrawing the balloon catheter from the urethral stricture. The inflated balloon catheter diameter can be such that the ratio of the balloon diameter to the nonvascular lumen diameter is about 1.01 to about 30, or about 1.2 to about 25, or about 1.5 to about 20, or about 1.01 or less, or less than, equal to, or greater than about 1.1, 1.2, 1.3, 1.4, 1.5, 1.6, 1.8, 2, 3, 4, 5, 6, 7, 8, 9, 10, 12, 14, 16, 18, 20, 22, 24, 26, 28, or about 30 or more.

In one embodiment, the one or more water-soluble additive promotes rapid release of the hydrophobic therapeutic agent from the balloon at the target site during an inflation period.

In one embodiment, the balloon has thereon a residual drug amount of less than 70% of the initial drug load after the withdrawing.

In one embodiment of the method, the ratio by weight of the therapeutic agent in the coating layer to the total weight of the one or more additives in the coating layer is about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more.

In one embodiment of the method, the initial drug load is from 1 microgram to 20 micrograms of the hydrophobic therapeutic agent per square millimeter of the balloon, or about 2 to about 6 micrograms, or about 1 microgram or less, or less than, equal to, or greater than about 2, 3, 4, 5, 6, 7, 8, 9, 10, 12, 14, 16, 18, or about 20 micrograms or more. The residual drug amount can be 70% or less of the initial drug load.

In one embodiment, the present invention relates to a method for treating an esophageal stricture, the method including flushing the esophageal stricture with water, saline solution or a water solution including at least one water soluble additive; inserting a balloon catheter to a target site in the esophageal stricture, the balloon catheter including a balloon and a coating layer overlying external surfaces of the balloon, wherein the coating layer includes at least one water-soluble second additive, and a hydrophobic therapeutic agent with an initial drug load of from 1 to 6 micrograms of the hydrophobic therapeutic agent per square millimeter of the balloon; the hydrophobic therapeutic agent is selected from the group consisting of paclitaxel, paclitaxel analogues, rapamycin, rapamycin analogues, and combinations thereof; the water-soluble additive is selected from the group consisting of N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the hydrophobic therapeutic agent in the coating layer to the total weight of the one or more water-soluble additives in the coating layer is from about 0.05 to 20; inflating the balloon until the coating layer contacts walls of the esophageal stricture at the target site for an inflation period; deflating the balloon after the inflation period, wherein the inflation period is from 0.1 minutes to 10 minutes; and withdrawing the balloon catheter from the esophageal stricture. The inflated balloon catheter diameter can be such that the ratio of the balloon diameter to the nonvascular lumen diameter is about 1.01 to about 30, or about 1.2 to about 25, or about 1.5 to about 20, or about 1.01 or less, or less than, equal to, or greater than about 1.1, 1.2, 1.3, 1.4, 1.5, 1.6, 1.8, 2, 3, 4, 5, 6, 7, 8, 9, 10, 12, 14, 16, 18, 20, 22, 24, 26, 28, or about 30 or more.

In one embodiment, the one or more water-soluble additives promote rapid release of the hydrophobic therapeutic agent from the balloon at the target site during an inflation period.

In one embodiment, the balloon has thereon a residual drug amount of less than 70% of the initial drug load after the withdrawing.

In one embodiment, the ratio by weight of the hydrophobic therapeutic agent in the coating layer to the total weight of the one or more additives in the coating layer is about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more.

In one embodiment, the initial drug load is from 1 microgram to 20 micrograms of the hydrophobic therapeutic agent per square millimeter of the balloon, or about 2 to about 6 micrograms, or about 1 microgram or less, or less than, equal to, or greater than about 2, 3, 4, 5, 6, 7, 8, 9, 10, 12, 14, 16, 18, or about 20 micrograms or more. The residual drug amount can be 70% or less of the initial drug load.

In one embodiment, the present invention relates to a method for treating a sinus stricture, the method including: flushing the sinus stricture with water, saline solution, or a water solution including at least one water soluble additives; inserting a balloon catheter to a target site in the sinus stricture, the balloon catheter including a balloon and a coating layer overlying external surfaces of the balloon, wherein the coating layer includes at least one water-soluble additive, and a hydrophobic therapeutic agent with an initial drug load of from 1 to 6 micrograms of the hydrophobic therapeutic agent per square millimeter of the balloon; the hydrophobic therapeutic agent is selected from the group consisting of budesonide, flunisolide, triamcinolone, beclomethasone, fluticasone, mometasone, mometasone furoate, dexamethasone, hydrocortisone, methylprednisolone, prednisone, cortisone, betamethasone, triamcinolone acetonide, and combinations thereof; the water-soluble additive is selected from the group consisting of N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the hydrophobic therapeutic agent in the coating layer to the total weight of the one or more water-soluble additives in the coating layer is from about 0.05 to 20; inflating the balloon until the coating layer contacts walls of the sinus stricture at the target site for an inflation period; deflating the balloon after the inflation period, wherein the inflation period is from 0.1 minutes to 10 minutes; and withdrawing the balloon catheter from the sinus stricture.

In various embodiments, during inflation of the balloon in a body lumen (e.g., during performance of a method of the present invention), the inflated balloon diameter of the catheter can be such that the ratio of the inflated balloon diameter to the nonvascular lumen diameter (i.e., the undilated body lumen) is any suitable ratio, such as about 1.01 to about 30, or about 1.2 to about 25, or about 1.5 to about 20, or about 1.01 or less, or less than, equal to, or greater than about 1.1, 1.2, 1.3, 1.4, 1.5, 1.6, 1.8, 2, 3, 4, 5, 6, 7, 8, 9, 10, 12, 14, 16, 18, 20, 22, 24, 26, 28, or about 30 or more. In various embodiments, the balloon catheter can be sufficient such that at a predetermined pressure (e.g., the nominal pressure) the balloon can have any suitable ratio (e.g., nominal ratio) of actual inflated balloon catheter diameter (e.g., the nominal inflated diameter, which may appear on a label associated with the catheter) to nonvascular lumen diameter; for example, at a pressure of about 3 atm (304 kPa) to about 30 atm (3040 kPa) (e.g., about 3 atm or less, or less than, equal to, or more than about 4 atm, 5, 6, 7, 8, 9, 10, 11, 12, 13, 14, 15, 16, 17, 18, 19, 20, 22, 24, 26, 28, or about 30 atm or more) the size of the inflated balloon catheter can be such that the ratio of the inflated balloon diameter to the nonvascular lumen diameter (i.e., the undilated body lumen) is any suitable ratio, such as about 1.01 to about 30, or about 1.2 to about 25, or about 1.2 to about 15, or about 1.5 to about 20, or about 1.01 or less, or less than, equal to, or greater than about 1.1, 1.2, 1.3, 1.4, 1.5, 1.6, 1.8, 2, 3, 4, 5, 6, 7, 8, 9, 10, 12, 14, 16, 18, 20, 22, 24, 26, 28, or about 30 or more. In various embodiments, the balloon catheter can have a ratio of nominal inflated balloon catheter diameter (e.g., the nominal inflated diameter that can appear on a label associated with the catheter) to undilated nonvascular lumen diameter of about 1.01 to about 30, or about 1.2 to about 25, or about 1.2 to about 15, or about 1.5 to about 20, or about 1.01 or less, or less than, equal to, or greater than about 1.1, 1.2, 1.3, 1.4, 1.5, 1.6, 1.8, 2, 3, 4, 5, 6, 7, 8, 9, 10, 12, 14, 16, 18, 20, 22, 24, 26, 28, or about 30 or more.

In one embodiment, the one or more water-soluble additives promote rapid release of the hydrophobic therapeutic agent from the balloon at the target site during an inflation period.

In one embodiment, the balloon has thereon a residual drug amount of less than 70% of the initial drug load after the withdrawing.

In one embodiment, the ratio by weight of the therapeutic agent in the coating layer to the total weight of the one or more additives is about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more.

In one embodiment, the initial drug load is from 1 microgram to 20 micrograms of the hydrophobic therapeutic agent per square millimeter of the balloon, or about 2 to about 6 micrograms, or about 1 microgram or less, or less than, equal to, or greater than about 2, 3, 4, 5, 6, 7, 8, 9, 10, 12, 14, 16, 18, or about 20 micrograms or more. The residual drug amount can be 70% or less of the initial drug load.

Additive.

The additive of embodiments of the present invention has two parts. One part is hydrophilic and the other part is a drug affinity part. The drug affinity part is a hydrophobic part and/or has an affinity to the therapeutic agent by hydrogen bonding and/or van der Waals interactions. The drug affinity part of the additive may bind the lipophilic drug, such as rapamycin or paclitaxel. The hydrophilic portion accelerates diffusion and increases permeation of the drug into tissue. It may facilitate rapid movement of drug off the medical device during deployment at the target site by preventing hydrophobic drug molecules from clumping to each other and to the device, increasing drug solubility in interstitial spaces, and/or accelerating drug lumen through polar head groups to the lipid bilayer of cell membranes of target tissues. The additives of embodiments of the present invention have two parts that function together to facilitate rapid release of drug off the device surface and uptake by target tissue during deployment (by accelerating drug contact with tissues for which drug has high affinity) while preventing the premature release of drug from the device surface prior to device deployment at the target site.

In embodiments of the present invention, the therapeutic agent is rapidly released after the medical device is brought into contact with tissue and is readily absorbed. For example, certain embodiments of devices of the present invention include drug coated balloon catheters that deliver a lipophilic anti-proliferative pharmaceutical (such as paclitaxel or rapamycin) to nonvascular tissue through brief, direct pressure contact at high drug concentration during balloon nonvascular body balloon dilation. The lipophilic drug, for example, is retained in target tissue at the delivery site, where it inhibits hyperplasia and restenosis yet allows epithelization. In these embodiments, coating formulations of the present invention not only facilitate rapid release of drug from the balloon surface and transfer of drug into target tissues during deployment, but also prevent drug from diffusing away from the device during transit through tortuous anatomy prior to reaching the target site and from exploding off the device during the initial phase of balloon inflation, before the drug coating is pressed into direct contact with the surface of the body lumen.

The additive according to certain embodiments has a drug affinity part and a hydrophilic part. The drug affinity part is a hydrophobic part and/or has an affinity to the therapeutic agent by hydrogen bonding and/or van der Waals interactions. The drug affinity part may include aliphatic and aromatic organic hydrocarbon compounds, such as benzene, toluene, and alkanes, among others. These parts are not water soluble. They may bind both hydrophobic drug, with which they share structural similarities, and lipids of cell membranes. They have no covalently bonded iodine. The drug affinity part may include functional groups that can form hydrogen bonds with drug and with itself. The hydrophilic part may include hydroxyl groups, amine groups, amide groups, carbonyl groups, carboxylic acid and anhydrides, ethyl oxide, ethyl glycol, polyethylene glycol, ascorbic acid, amino acid, amino alcohol, glucose, sucrose, sorbitan, glycerol, polyalcohol, phosphates, sulfates, organic salts and their substituted molecules, among others. One or more hydroxyl, carboxyl, acid, amide or amine groups, for example, may be advantageous since they easily displace water molecules that are hydrogen-bound to polar head groups and surface proteins of cell membranes and may function to remove this barrier between hydrophobic drug and cell membrane lipid. These parts can dissolve in water and polar solvents. In various embodiments, these additives do not include oils, lipids, or polymers. In various embodiments, the therapeutic agent is not enclosed in micelles or liposomes or encapsulated in polymer particles. The additive of embodiments of the present invention has components to both bind drug and facilitate its rapid movement off the medical device during deployment and into target tissues.

The additives in embodiments of the present invention are surfactants and chemical compounds with one or more hydroxyl, amino, carbonyl, carboxyl, acid, amide or ester moieties. The surfactants include ionic, nonionic, aliphatic, and aromatic surfactants. The chemical compounds with one or more hydroxyl, amino, carbonyl, carboxyl, acid, amide or ester moieties are chosen from amino alcohols, hydroxyl carboxylic acid and anhydrides, ethyl oxide, ethyl glycols, amino acids, peptides, proteins, sugars, glucose, sucrose, sorbitan, glycerol, polyalcohol, phosphates, sulfates, organic acids, esters, salts, vitamins, and their substituted molecules.

As is well known in the art, the terms "hydrophilic" and "hydrophobic" are relative terms. To function as an additive in exemplary embodiments of the present invention, the compound includes polar or charged hydrophilic moieties as well as non-polar hydrophobic (lipophilic) moieties.

An empirical parameter commonly used in medicinal chemistry to characterize the relative hydrophilicity and hydrophobicity of pharmaceutical compounds is the partition coefficient, P, the ratio of concentrations of unionized compound in the two phases of a mixture of two immiscible solvents, usually octanol and water, such that P=([solute]octanol/[solute]water). Compounds with higher log Ps are more hydrophobic, while compounds with lower log Ps are more hydrophilic. Lipinski's rule suggests that pharmaceutical compounds having log P<5 are typically more membrane permeable. For purposes of certain embodiments of the present invention, for example, the additive has log P less than log P of the drug to be formulated (as an example, log P of paclitaxel is 7.4). A greater log P difference between the drug and the additive can facilitate phase separation of drug. For example, if log P of the additive is much lower than log P of the drug, the additive may accelerate the release of drug in an aqueous environment from the surface of a device to which drug might otherwise tightly adhere, thereby accelerating drug delivery to tissue during brief deployment at the site of intervention. In certain embodiments of the present invention, log P of the additive is negative. In other embodiments, log P of the additive is less than log P of the drug. While a compound's octanol-water partition coefficient P or log P is useful as a measurement of relative hydrophilicity and hydrophobicity, it is merely a rough guide that may be useful in defining suitable additives for use in embodiments of the present invention.

Suitable additives that can be used in embodiments of the present invention include, without limitation, organic and inorganic pharmaceutical recipients, natural products and derivatives thereof (such as sugars, vitamins, amino acids, peptides, proteins, and fatty acids), low molecular weight oligomers, surfactants (anionic, cationic, non-ionic, and ionic), and mixtures thereof. The following detailed list of additives useful in the present invention is provided for exemplary purposes only and is not intended to be comprehensive. Many other additives may be useful for purposes of the present invention.

Surfactants.

The surfactant can be any surfactant suitable for use in pharmaceutical compositions. Such surfactants can be anionic, cationic, zwitterionic or non-ionic. Mixtures of surfactants are also within the scope of the invention, as are combinations of surfactant and other additives. Surfactants often have one or more long aliphatic chains such as fatty acids that may insert directly into lipid bilayers of cell membranes to form part of the lipid structure, while other components of the surfactants loosen the lipid structure and enhance drug penetration and absorption. The contrast agent iopromide does not have these properties.

An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10. In certain embodiments of the present invention, a higher HLB value is utilized, since increased hydrophilicity may facilitate release of hydrophobic drug from the surface of the device. In one embodiment, the HLB of the surfactant additive is higher than 10. In another embodiment, the additive HLB is higher than 14. Alternatively, surfactants having lower HLB may be utilized to prevent drug loss prior to device deployment at the target site, for example in a top coat over a drug layer that has a very hydrophilic additive.

It should be understood that the HLB value of a surfactant is merely a rough guide generally used to enable formulation of industrial, pharmaceutical and cosmetic emulsions, for example. For many important surfactants, including several polyethoxylated surfactants, it has been reported that HLB values can differ by as much as about 8 HLB units, depending upon the empirical method chosen to determine the HLB value (Schott, J. Pharm. Sciences, 79(1), 87-88 (1990)). Keeping these inherent difficulties in mind, and using HLB values as a guide, surfactants may be identified that have suitable hydrophilicity or hydrophobicity for use in embodiments of the present invention, as described herein.

PEG-Fatty Acids and PEG-Fatty Acid Mono and Diesters.

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful in embodiments of the present invention. Examples of hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. The HLB values are in the range of 4-20.

Polyethylene glycol fatty acid diesters are also suitable for use as surfactants in the compositions of embodiments of the present invention. Hydrophilic surfactants include PEG-20 dilaurate, PEG-20 dioleate, PEG-20 distearate, PEG-32 dilaurate and PEG-32 dioleate. The HLB values are in the range of 5-15.

In general, mixtures of surfactants are also useful in embodiments of the present invention, including mixtures of two or more commercial surfactants as well as mixtures of surfactants with another additive or additives. Several PEG-fatty acid esters are marketed commercially as mixtures or mono- and di-esters.

Polyethylene Glycol Glycerol Fatty Acid Esters.

Hydrophilic surfactants are PEG-20 glyceryl laurate, PEG-30 glyceryl laurate, PEG-40 glyceryl laurate, PEG-20 glyceryl oleate, and PEG-30 glyceryl oleate.

Alcohol-Oil Transesterification Products.

A large number of surfactants of different degrees of hydrophobicity or hydrophilicity can be prepared by reaction of alcohols or polyalcohol with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Alcohols include glycerol, propylene glycol, ethylene glycol, polyethylene glycol, sorbitol, and pentaerythritol. Among these alcohol-oil transesterified surfactants, hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). For example, hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil®b M 2735 CS), PEG-8 corn oil (Labrafil® WL 2609 BS), PEG-20 corn glycerides (Crovol M40), and PEG-20 almond glycerides (Crovol A40).

Polyglyceryl Fatty Acids.

Polyglycerol esters of fatty acids are also suitable surfactants for use in embodiments of the present invention. Among the polyglyceryl fatty acid esters, hydrophobic surfactants include polyglyceryl oleate (Plurol Oleique), polyglyceryl-2 dioleate (Nikkol DGDO), polyglyceryl-10 trioleate, polyglyceryl stearate, polyglyceryl laurate, polyglyceryl myristate, polyglyceryl palmitate, and polyglyceryl linoleate. Hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (CaproI® PEG 860), polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate. Polyglyceryl polyricinoleates (Polymuls) are also surfactants.

Propylene Glycol Fatty Acid Esters.

Esters of propylene glycol and fatty acids are suitable surfactants for use in embodiments of the present invention. In this surfactant class, hydrophobic surfactants include propylene glycol monolaurate (Lauroglycol FCC), propylene glycol ricinoleate (Propymuls), propylene glycol monooleate (Myverol P-06), propylene glycol dicaprylate/dicaprate (Captex® 200), and propylene glycol dioctanoate (Captex® 800).

Sterol and Sterol Derivatives.

Sterols and derivatives of sterols are suitable surfactants for use in embodiments of the present invention. Derivatives include the polyethylene glycol derivatives. A surfactant in this class is PEG-24 cholesterol ether (Solulan C-24).

Polyethylene Glycol Sorbitan Fatty Acid Esters.

A variety of PEG-sorbitan fatty acid esters are available and are suitable for use as surfactants in embodiments of the present invention. Among the PEG-sorbitan fatty acid esters, surfactants include PEG-20 sorbitan monolaurate (Tween- 20), PEG-20 sorbitan monopalmitate (Tween-40), PEG-20 sorbitan monostearate (Tween-60), PEG-20 sorbitan monooleate (Tween-80). In some embodiments, laurate esters are utilized because they have a short lipid chain compared with oleate esters, increasing drug absorption.

Polyethylene Glycol Alkyl Ethers.

Ethers of polyethylene glycol and alkyl alcohols are suitable surfactants for use in embodiments of the present invention. Ethers include PEG-3 oleyl ether (Volpo 3) and PEG-4 lauryl ether (Brij 30).

Sugar and its Derivatives.

Sugar derivatives are suitable surfactants for use in embodiments of the present invention. Surfactants in this class include sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, and octyl-β-D-thioglucopyranoside.

Polyethylene Glycol Alkyl Phenols.

Several PEG-alkyl phenol surfactants are available, such as PEG-10-100 nonyl phenol and PEG-15-100 octyl phenol ether, Tyloxapol, octoxynol, nonoxynol, and are suitable for use in embodiments of the present invention.

Polyoxyethylene-Polyoxypropylene (POE-POP) Block Copolymers.

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in embodiments of the present invention. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is "poloxamer" (CAS 9003-11-6). These polymers have the formula: $HO(C_2H_4O)_a(C_3H_6O)_n(C_2H_4O)_aH$ where "a" and "b" denote the number of polyoxyethylene and polyoxypropylene units, respectively.

Hydrophilic surfactants of this class include Poloxamers 108, 188, 217, 238, 288, 338, and 407. Hydrophobic surfactants in this class include Poloxamers 124, 182, 183, 212, 331, and 335.

Sorbitan Fatty Acid Esters.

Sorbitan esters of fatty acids are suitable surfactants for use in embodiments of the present invention. Among these esters, hydrophobic surfactants include sorbitan monolaurate (Arlacel 20), sorbitan monopalmitate (Span-40), and sorbitan monooleate (Span-80), sorbitan monostearate.

The sorbitan monopalmitate, an amphiphilic derivative of Vitamin C (which has Vitamin C activity), can serve two important functions in solubilization systems. First, it possesses effective polar groups that can modulate the microenvironment. These polar groups are the same groups that make vitamin C itself (ascorbic acid) one of the most water-soluble organic solid compounds available: ascorbic acid is soluble to about 30 wt/wt % in water (very close to the solubility of sodium chloride, for example). And second, when the pH increases so as to convert a fraction of the ascorbyl palmitate to a more soluble salt, such as sodium ascorbyl palmitate.

Ionic Surfactants.

Ionic surfactants, including cationic, anionic and zwitterionic surfactants, are suitable hydrophilic surfactants for use in embodiments of the present invention. Ionic surfactants include quaternary ammonium salts, fatty acid salts and bile salts. Specifically, ionic surfactants include benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylester of sodium sulfonsuccinic acid, sodium dioctyl sulfosuccinate, sodium cholate, and sodium taurocholate. They can be dissolved in both organic solvents (such as ethanol, acetone, and toluene) and water. This is especially useful for medical device coatings because it simplifies the preparation and coating process and has good adhesive properties. Water insoluble drugs are commonly dissolved in organic solvents.

Some of the surfactants described herein are very stable under heating. They survive an ethylene oxide sterilization process. They do not react with drugs such as paclitaxel or rapamycin under the sterilization process. The hydroxyl, ester, amide groups are utilized because they are unlikely to react with drug, while amine and acid groups often do react with paclitaxel or rapamycin during sterilization. Furthermore, surfactant additives improve the integrity and quality of the coating layer, so that particles do not fall off during handling. When the surfactants described herein are formulated with paclitaxel, experimentally it protects drug from premature release during the device delivery process while facilitating rapid release and elution of paclitaxel during a very brief deployment time of 0.2 to 10 minutes at the target site. Drug absorption by tissues at the target site is unexpectedly high experimentally.

Chemical Compounds with One or More Hydroxyl, Amino, Carbonyl, Carboxyl, Acid, Amide or Ester Moieties.

The chemical compounds with one or more hydroxyl, amino, carbonyl, carboxyl, acid, amide or ester moieties include creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, N-acetylglucosamine, N-octyl-D-gluconamide, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-Lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate (e.g., Labrasol®), PEG caprate, PEG caproate, glyceryl monocaprylate, glyceryl monocaprate, glyceryl monocaproate, monolaurin, monocaprin, monocaprylin, monomyristin, monopalmitolein, and monoolein.

The chemical compounds with one or more hydroxyl, amino, carbonyl, carboxyl, acid, amide or ester moieties include amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohols and organic acids, and their substituted molecules. Hydrophilic chemical compounds with one or more hydroxyl, amino, carbonyl, carboxyl, acid, amide or ester moieties having a molecular weight less than 5,000-10,000 are utilized in certain embodiments. In other embodiments, molecular weight of the additive with one or more hydroxyl, amino, carbonyl, carboxyl, acid, amide, or ester moieties is less than 1000-5,000, or less than 750-1,000, or less than 750. In these embodiments, the molecular weight of the additive is to be less than that of the drug to be delivered. Further, the molecular weight of the additive is to be higher than 80 since molecules with molecular weight less than 80 very easily evaporate and do not stay in the coating of a medical device. Small molecules can diffuse quickly. They can release themselves easily from the delivery balloon, accelerating release of drug, and they can diffuse away from drug when the drug binds tissue of the body lumens.

In certain embodiments, additives with more than four hydroxyl groups are utilized, for example in the case of a high molecular weight additive. Large molecules diffuse slowly. If the molecular weight of the additive or the chemical compound is high, for example if the molecular weight is above 800, above 1000, above 1200, above 1500, or above 2000; large molecules may elute off of the surface of the medical device too slowly to release drug under 2 minutes. If these large molecules contain more than four hydroxyl groups they have increased hydrophilic properties, which is necessary for relatively large molecules to release drug quickly. The increased hydrophilicity helps elute the coating off the balloon, accelerates release of drug, and improves or facilitates drug movement through water barrier and polar head groups of lipid bilayers to penetrate tissues. In one embodiment, the hydroxyl group is utilized as the hydrophilic moiety because it is unlikely to react with water insoluble drug, such as paclitaxel or rapamycin. In some embodiments, the chemical compound having more than four hydroxyl groups has a melting point of 120° C., or less. In some embodiments, the chemical compound having more than four hydroxyl groups has three adjacent hydroxyl groups that in stereo configuration are all on one side of the molecule. For example, sorbitol and xylitol have three adjacent hydroxyl groups that in stereo configuration are all on one side of the molecule, while galactitol does not. The difference impacts the physical properties of the isomers such as the melting temperature. The stereo configuration of the three adjacent hydroxyl groups may enhance drug binding. This will lead to improved compatibility of the water insoluble drug and hydrophilic additive, and improved tissue uptake and absorption of drug.

Some of the chemical compounds with one or more hydroxyl, amine, carbonyl, carboxyl, or ester moieties described herein are very stable under heating. They survive an ethylene oxide sterilization process and do not react with the water insoluble drug paclitaxel or rapamycin during sterilization, L-ascorbic acid and its salt and diethanolamine, on the other hand, do not necessarily survive such a sterilization process, and they react with paclitaxel. A different sterilization method is therefore utilized for L-ascorbic acid and diethanolamine. For example, hydroxyl, ester, and amide groups are utilized because they are unlikely to react with therapeutic agents such as paclitaxel or rapamycin. Sometimes, amine and acid groups do react with paclitaxel, for example, experimentally, benzoic acid, gentisic acid, diethanolamine, and ascorbic acid were not stable under ethylene oxide sterilization, heating, and aging process and reacted with paclitaxel. When the chemical compounds described herein are formulated with paclitaxel, a top coat layer may be advantageous in order to prevent premature drug loss during the device delivery process before deployment at the target site, since hydrophilic small molecules sometimes release drug too easily. The chemical compounds herein rapidly elute drug off the balloon during deployment at the target site. Surprisingly, even though some drug is lost during transit of the device to the target site when the coating contains these additives, experimentally drug absorption by tissue is unexpectedly high after only 0.2-10 minutes of deployment, for example, with the additive hydroxyl lactones such as ribonic acid lactone and gluconolactone.

Fat-Soluble Vitamins and Salts Thereof.

Vitamins A, D, E and K in many of their various forms and provitamin forms are considered as fat-soluble vitamins and in addition to these a number of other vitamins and vitamin sources or close relatives are also fat-soluble and have polar groups, and relatively high octanol-water partition coefficients. Clearly, the general class of such compounds has a history of safe use and high benefit to risk ratio, making them useful as additives in embodiments of the present invention.

The following examples of fat-soluble vitamin derivatives and/or sources are also useful as additives: Alpha-tocopherol, beta-tocopherol, gamma-tocopherol, delta-tocopherol, tocopherol acetate, ergosterol, 1-alpha-hydroxycholecalciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K-S(II). Folic acid is also of this type, and although it is water-soluble at physiological pH, it can be formulated in the free acid form. Other derivatives of fat-soluble vitamins useful in embodiments of the present invention may easily be obtained via well known chemical reactions with hydrophilic molecules.

Water-Soluble Vitamins and their Amphiphilic Derivatives.

Vitamins B, C, U, pantothenic acid, folic acid, and some of the menadione-related vitamins/provitamins in many of their various forms are considered water-soluble vitamins. These may also be conjugated or complexed with hydrophobic moieties or multivalent ions into amphiphilic forms having relatively high octanol-water partition coefficients and polar groups. Again, such compounds can be of low toxicity and high benefit to risk ratio, making them useful as additives in embodiments of the present invention. Salts of these can also be useful as additives in the present invention. Examples of water-soluble vitamins and derivatives include, without limitation, acetiamine, benfotiamine, pantothenic acid, cetotiamine, cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U. Also, as mentioned above, folic acid is, over a wide pH range including physiological pH, water-soluble, as a salt.

Compounds in which an amino or other basic group is present can easily be modified by simple acid-base reaction with a hydrophobic group-containing acid such as a fatty acid (especially lauric, oleic, myristic, palmitic, stearic, or 2-ethylhexanoic acid), low-solubility amino acid, benzoic acid, salicylic acid, or an acidic fat-soluble vitamin (such as riboflavin). Other compounds might be obtained by reacting such an acid with another group on the vitamin such as a hydroxyl group to form a linkage such as an ester linkage, etc. Derivatives of a water-soluble vitamin containing an acidic group can be generated in reactions with a hydrophobic group-containing reactant such as stearylamine or riboflavine, for example, to create a compound that is useful in embodiments of the present invention. The linkage of a palmitate chain to vitamin C yields ascorbyl palmitate.

Amino Acids and their Salts.

Alanine, arginine, asparagines, aspartic acid, cysteine, cystine, glutamic acid, glutamine, glycine, histidine, proline, isoleucine, leucine, lysine, methionine, phenylalanine, serine, threonine, tryptophan, tyrosine, valine, and derivatives thereof are other useful additives in embodiments of the invention.

Certain amino acids, in their zwitterionic form and/or in a salt form with a monovalent or multivalent ion, have polar groups, relatively high octanol-water partition coefficients, and are useful in embodiments of the present invention. In the context of the present disclosure we take "low-solubility amino acid" to mean an amino acid which has solubility in unbuffered water of less than about 4% (40 mg/ml). These include Cystine, tyrosine, tryptophan, leucine, isoleucine, phenylalanine, asparagine, aspartic acid, glutamic acid, and methionine.

Amino acid dimers, sugar-conjugates, and other derivatives are also useful. Through simple reactions well known in the art hydrophilic molecules may be joined to hydrophobic amino acids, or hydrophobic molecules to hydrophilic amino acids, to make additional additives useful in embodiments of the present invention.

Catecholamines, such as dopamine, levodopa, carbidopa, and DOPA, are also useful as additives.

Oligopeptides, Peptides and Proteins.

Oligopeptides and peptides are useful as additives, since hydrophobic and hydrophilic amino acids may be easily coupled and various sequences of amino acids may be tested to maximally facilitate permeation of tissue by drug.

Proteins are also useful as additives in embodiments of the present invention. Serum albumin, for example, is a useful additive since it is water-soluble and contains significant hydrophobic parts to bind drug: paclitaxel is 89% to 98% protein-bound after human intravenous infusion, and rapamycin is 92% protein bound, primarily (97%) to albumin. Furthermore, paclitaxel solubility in PBS increases over 20-fold with the addition of BSA. Albumin is naturally present at high concentrations in serum and is thus very safe for human use.

Other useful proteins include, without limitation, other albumins, immunoglobulins, caseins, hemoglobins, lysozymes, immunoglobins, a-2-macroglobulin, fibronectins, vitronectins, firbinogens, lipases, and the like.

Organic Acids and their Esters and Anhydrides.

Examples are acetic acid and anhydride, benzoic acid and anhydride, diethylenetriaminepentaacetic acid dianhydride, ethylenediaminetetraacetic dianhydride, maleic acid and anhydride, succinic acid and anhydride, diglycolic anhydride, glutaric anhydride, ascorbic acid, citric acid, tartaric acid, lactic acid, oxalic acid aspartic acid, nicotinic acid, 2-pyrrolidone-5-carboxylic acid, and 2-pyrrolidone.

These esters and anhydrides are soluble in organic solvents such as ethanol, acetone, methylethylketone, ethylacetate. The water insoluble drugs can be dissolved in organic solvent with these esters and anhydrides, then coated easily on to the medical device, then hydrolyzed under high pH conditions. The hydrolyzed anhydrides or esters are acids or alcohols, which are water soluble and can effectively carry the drugs off the device into the vessel walls.

Other Chemical Compounds with One or More Hydroxyl, Amine, Carbonyl, Carboxyl, or Ester Moieties.

The additives according to embodiments include amino alcohols, alcohols, amines, acids, amides and hydroxyl acids in both cyclic and linear aliphatic and aromatic groups. Examples are L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sinapic acid, vanillic acid, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerol, multiglycerols, galactitol, di(ethylene glycol), tri(ethylene glycol), tetra(ethylene glycol), penta(ethylene glycol), poly (ethylene glycol) oligomers, di(propylene glycol), tri (propylene glycol), tetra(propylene glycol, and penta (propylene glycol), poly(propylene glycol) oligomers, a block copolymer of polyethylene glycol and polypropylene glycol, and derivatives and combinations thereof.

Combinations of additives are also useful for purposes of the present invention.

One embodiment includes the combination or mixture of two additives, for example, a first additive including a surfactant and a second additive including a chemical compound with one or more hydroxyl, amine, carbonyl, carboxyl, or ester moieties.

The combination or mixture of the surfactant and the small water-soluble molecule (the chemical compounds with one or more hydroxyl, amine, carbonyl, carboxyl, or ester moieties) has advantages. Formulations including mixtures of the two additives with water-insoluble drug are in certain cases superior to mixtures including either additive alone. The hydrophobic drugs bind extremely water-soluble small molecules more poorly than they do surfactants. They are often phase separated from the small water-soluble molecules, which can lead to suboptimal coating uniformity and integrity. The water-insoluble drug has Log P higher than both that of the surfactant and that of small water-soluble molecules. However, Log P of the surfactant is typically higher than Log P of the chemical compounds with one or more hydroxyl, amine, carbonyl, carboxyl, or ester moieties. The surfactant has a relatively high Log P (usually above 0) and the water soluble molecules have low Log P (usually below 0). Some surfactants, when used as additives in embodiments of the present invention, adhere so strongly to the water-insoluble drug and the surface of the medical device that drug is not able to rapidly release from the surface of the medical device at the target site. On the other hand, some of the water-soluble small molecules (with one or more hydroxyl, amine, carbonyl, carboxyl, or ester moieties) adhere so poorly to the medical device that they release drug before it reaches the target site, for example, into serum during the transit of a coated balloon catheter to the site targeted for intervention. Surprisingly, by adjusting the ratio of the concentrations of the small hydrophilic molecule and the surfactant in the formulation, the inventor has found that the coating stability during transit and rapid drug release when inflated and pressed against tissues of the lumen wall at the target site of therapeutic intervention in certain cases is superior to a formulation including either additive alone. Furthermore, the miscibility and compatibility of the water-insoluble drug and the highly water-soluble molecules is improved by the presence of the surfactant. The surfactant also improves coating uniformity and integrity by its good adhesion to the drug and the small molecules. The long chain hydrophobic part of the surfactant binds drug tightly while the hydrophilic part of the surfactant binds the water-soluble small molecules.

The surfactants in the mixture or the combination include all of the surfactants described herein for use in embodiments of the invention. The surfactant in the mixture may be chosen from PEG sorbitan fatty esters, PEG omega-3 fatty esters and alcohols, glycerol fatty esters, sorbitan fatty esters, PEG glyceryl fatty esters, PEG fatty esters, sugar fatty esters, PEG sugar esters, Tween 20, Tween 40, Tween 60, p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG laurayl ether, Tween 20, Tween 40, Tween 60, Tween 80, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-β-D-thioglucopyranoside and their derivatives.

The chemical compound with one or more hydroxyl, amine, carbonyl, carboxyl, or ester moieties in the mixture or the combination include all of the chemical compounds with one or more hydroxyl, amine, carbonyl, carboxyl, or ester moieties described herein for use in embodiments of the invention. The chemical compound with one or more hydroxyl, amine, carbonyl, carboxyl, or ester moieties in the mixture has at least one hydroxyl group in one of the embodiments in the inventions. In certain embodiments, additives with more than four hydroxyl groups are utilized, for example in the case of a high molecular weight additive. In some embodiments, the chemical compound having more than four hydroxyl groups has a melting point of 120° C., or less. Large molecules diffuse slowly. If the molecular weight of the additive or the chemical compound is high, for example if the molecular weight is above 800, above 1000, above 1200, above 1500, or above 2000; large molecules may elute off of the surface of the medical device too slowly to release drug under 2 minutes. If these large molecules contain more than four hydroxyl groups they have increased hydrophilic properties, which is necessary for relatively large molecules to release drug quickly. The increased hydrophilicity helps elute the coating off the balloon, accelerates release of drug, and improves or facilitates drug movement through water barrier and polar head groups of lipid bilayers to penetrate tissues. In one embodiment, the hydroxyl group is utilized as the hydrophilic moiety because it is unlikely to react with water insoluble drug, such as paclitaxel or rapamycin.

The chemical compound with one or more hydroxyl, amine, carbonyl, carboxyl, or ester moieties in the mixture is chosen from L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sinapic acid, vanillic acid, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), and penta(propylene glycol), poly(propylene glycol) oligomers, a block copolymer of polyethylene glycol and polypropylene glycol, and derivatives and combinations thereof.

Mixtures or combinations of a surfactant and a water-soluble small molecule confer the advantages of both additives. The water insoluble drug often has a poor compatibility with highly water-soluble chemical compounds, and the surfactant improves compatibility. The surfactant also improves the coating quality, uniformity, and integrity, and particles do not fall off the balloon during handling. The surfactant reduces drug loss during transit to a target site. The water-soluble chemical compound improves the release of drug off the balloon and absorption of the drug in the tissue. Experimentally, the combination was surprisingly effective at preventing drug release during transit and achieving high drug levels in tissue after very brief 0.2-2 minute deployment. Furthermore, in animal studies it effectively reduced stenosis and late lumen loss.

Some of the mixtures or combinations of surfactants and water-soluble small molecules are very stable under heating. They survived an ethylene oxide sterilization process and do not react with the water insoluble drug paclitaxel or rapamycin during sterilization. In one embodiment, the hydroxyl, ester, amide groups are utilized because they are unlikely to react with therapeutic agents such as paclitaxel or rapamycin. Sometimes amine and acid groups do react with paclitaxel and are not stable under ethylene oxide sterilization, heating, and aging. When the mixtures or combinations described herein are formulated with paclitaxel, a top coat layer may be advantageous in order to protect the drug layer and from premature drug loss during the device.

Examples of additives include p-isononylphenoxypolyglycidol, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine (amino acids), cetotiamine, cyclothiamine, dexpanthenol, niacinamide, nicotinic acid and its salt, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), and penta(propylene glycol), poly(propylene glycol) oligomers, a block copolymer of polyethylene glycol and polypropylene glycol, and derivatives and combinations thereof. Examples of additives include chemical compounds with one or more hydroxyl, amino, carbonyl, carboxyl, or ester moieties. Some of these additives are both water-soluble and organic solvent-soluble. They have good adhesive properties and adhere to the surface of polyamide medical devices, such as balloon catheters. They may therefore be used in the adherent layer, top layer, and/or in the drug layer of embodiments of the present invention. The aromatic and aliphatic groups increase the solubility of water insoluble drugs in the coating solution, and the polar groups of alcohols and acids accelerate drug permeation of tissue.

Other additives according to embodiments of the invention include hydroxyl ketone, hydroxyl lactone, hydroxyl acid, hydroxyl ester, and hydroxyl amide. Examples are gluconolactone, D-glucoheptono-1,4-lactone, glucooctanoic lactone, gulonic acid lactone, mannoic lactone, erythronic acid lactone, ribonic acid lactone, glucuronic acid, gluconic acid, gentisic acid, lactobionic acid, lactic acid, acetaminophen, vanillic acid, sinapic acid, hydroxybenzoic acid, methyl paraben, propyl paraben, and derivatives thereof.

From a structural point of view, these additives share structural similarities and are compatible with water insoluble drugs (such as paclitaxel and rapamycin). They often contain double bonds such as $C=C$, $C=N$, $C=O$ in aromatic or aliphatic structures. These additives also contain amine, alcohol, ester, amide, anhydride, carboxylic acid, and/or hydroxyl groups. They may form hydrogen bonds and/or van der Waals interactions with drug. They are also useful in the top layer in the coating. Compounds containing one or more hydroxyl, carboxyl, or amine groups, for example, are especially useful as additives since they facilitate drug release from the device surface and easily displace water next to the polar head groups and surface proteins of cell membranes and may thereby remove this barrier to hydrophobic drug permeability. They accelerate movement of a hydrophobic drug off the balloon to the lipid layer of cell membranes and tissues for which it has very high affinity. They may also carry or accelerate the movement of drug off the balloon into more aqueous environments such as the interstitial space, for example, of nonvascular tissues that have been injured by balloon angioplasty or stent expansion. Additives such as polyglyceryl fatty esters, ascorbic ester of fatty acids, sugar esters, alcohols and ethers of fatty acids have fatty chains that can integrate into the lipid structure of target tissue membranes, carrying drug to lipid structures. Some of the amino acids, vitamins and organic acids have aromatic $C=N$ groups as well as amino, hydroxyl, and carboxylic components to their structure. They have structural parts that can bind or complex with hydrophobic drug, such as paclitaxel or rapamycin, and they also have structural parts that facilitate tissue penetration by removing barriers between hydrophobic drug and lipid structure of cell membranes.

For example, isononylphenylpolyglycidol (Olin-10 G and Surfactant-10G), PEG glyceryl monooleate, sorbitan monolaurate (Arlacel 20), sorbitan monopalmitate (Span-40), sorbitan monooleate (Span-80), sorbitan monostearate, polyglyceryl-10 oleate, polyglyceryl-10 laurate, polyglyceryl-10 palmitate, and polyglyceryl-10 stearate all have more than four hydroxyl groups in their hydrophilic part. These hydroxyl groups have very good affinity for the vessel wall and can displace hydrogen-bound water molecules. At the same time, they have long chains of fatty acid, alcohol, ether and ester that can both complex with hydrophobic drug and integrate into the lipid structure of the cell membranes to form the part of the lipid structure. This deformation or loosening of the lipid membrane of target cells may further accelerate permeation of hydrophobic drug into tissue.

For another example, L-ascorbic acid, thiamine, maleic acids, niacinamide, and 2-pyrrolidone-5-carboxylic acid all have a very high water and ethanol solubility and a low molecular weight and small size. They also have structural components including aromatic $C=N$, amino, hydroxyl, and carboxylic groups. These structures have very good compatibility with paclitaxel and rapamycin and can increase the solubility of these water-insoluble drugs in water and enhance their absorption into tissues. However, they often have poor adhesion to the surface of medical devices. They are therefore used in combination with other additives in the drug layer and top layer where they are useful to enhance drug absorption. Vitamin D2 and D3 are especially useful because they themselves have anti-restenotic effects and reduce thrombosis, especially when used in combination with paclitaxel.

In embodiments of the present invention, the additive is soluble in aqueous solvents and is soluble in organic solvents. Extremely hydrophobic compounds that lack sufficient hydrophilic parts and are insoluble in aqueous solvent, such as the dye Sudan Red, are not useful as additives in these embodiments. Sudan red is also genotoxic.

In one embodiment, the concentration density of the at least one therapeutic agent applied to the surface of the medical device is from about 1 to 20 µg/mm$^2$, or from about 2 to 6 µg/mm$^2$, or about 0.5 microgram/mm$^2$ or less, or less than, equal to, or greater than about 1, 2, 3, 4, 5, 6, 7, 8, 9, 10, 12, 14, 16, 18, or about 20 micrograms/mm² or more. In one embodiment, the concentration of the at least one additive applied to the surface of the medical device is from about 0.5 to 20 μg/mm², or from about 2 to 6 μg/mm², or about 0.5 microgram/mm² or less, or less than, equal to, or greater than about 1, 2, 3, 4, 5, 6, 7, 8, 9, 10, 12, 14, 16, 18, or about 20 micrograms/mm² or more. The ratio of additives to drug by weight in the coating layer in embodiments of the present invention is about 20 to 0.05, about 10 to 0.1, or about 5 to 0.15.

The relative amount of the therapeutic agent and the additive in the coating layer, may vary depending on applicable circumstances. The optimal amount of the additive can depend upon, for example, the particular therapeutic agent and additive selected, the critical micelle concentration of the surface modifier if it forms micelles, the hydrophilic-lipophilic-balance (HLB) of a surfactant or an additive's octonol-water partition coefficient (P), the melting point of the additive, the water solubility of the additive and/or therapeutic agent, the surface tension of water solutions of the surface modifier, etc.

Other considerations will further inform the choice of specific proportions of different additives. These considerations include the degree of bioacceptability of the additives and the desired dosage of hydrophobic therapeutic agent to be provided.

Therapeutic Agent.

The drugs or biologically active materials, which can be used in embodiments of the present invention, can be any therapeutic agent or substance. The drugs can be of various physical states, e.g., molecular distribution, crystal forms or cluster forms. Examples of drugs that are especially useful in embodiments of the present invention are lipophilic substantially water insoluble drugs, such as paclitaxel, rapamycin, daunorubicin, doxorubicin, lapachone, vitamin D2 and D3 and analogues and derivatives thereof. These drugs are especially suitable for use in a coating on a balloon catheter used to treat tissue of the vasculature.

Other drugs that may be useful in embodiments of the present invention include, without limitation, glucocorticoids (e.g., dexamethasone, betamethasone), hirudin, angiopeptin, aspirin, growth factors, antisense agents, anti-cancer agents, anti-proliferative agents, oligonucleotides, and, more generally, anti-platelet agents, anti-coagulant agents, anti-mitotic agents, antioxidants, anti-metabolite agents, anti-chemotactic, and anti-inflammatory agents.

Some drugs that are considered particularly suitable for the airway, sinus and other nasal lumens are corticosteroids such as, budesonide, flunisolide, triamcinolone, beclomethasone, fluticasone, mometasone, mometasone furoate, dexamethasone, hydrocortisone, methylprednisolone, prednisone, cortisone, betamethasone, triamcinolone acetonide, or the like. Some other suitable drugs are bronchodilators such as terbutaline, albuterol, ipratropium, pirbuterol, epinephrine, salmeterol, levalbuterol, formoterol, or the like.

Also useful in embodiments of the present invention are polynucleotides, antisense, RNAi, or siRNA, for example, that inhibit inflammation and/or smooth muscle cell or fibroblast proliferation.

Anti-platelet agents can include drugs such as aspirin and dipyridamole. Aspirin is classified as an analgesic, anti-pyretic, anti-inflammatory and anti-platelet drug. Dipyridamole is a drug similar to aspirin in that it has anti-platelet characteristics. Dipyridamole is also classified as a coronary vasodilator. Anti-coagulant agents for use in embodiments of the present invention can include drugs such as heparin, protamine, hirudin and tick anticoagulant protein. Anti-oxidant agents can include probucol. Anti-proliferative agents can include drugs such as amlodipine and doxazosin. Anti-mitotic agents and anti-metabolite agents that can be used in embodiments of the present invention include drugs such as methotrexate, azathioprine, vincristine, vinblastine, 5-fluorouracil, adriamycin, and mutamycin. Antibiotic agents for use in embodiments of the present invention include penicillin, cefoxitin, oxacillin, tobramycin, and gentamicin. Suitable antioxidants for use in embodiments of the present invention include probucol. Additionally, genes or nucleic acids, or portions thereof can be used as the therapeutic agent in embodiments of the present invention. Furthermore, collagen-synthesis inhibitors, such as tranilast, can be used as a therapeutic agent in embodiments of the present invention.

Photosensitizing agents for photodynamic or radiation therapy, including various porphyrin compounds such as porfimer, for example, are also useful as drugs in embodiments of the present invention.

Drugs for use in embodiments of the present invention also include everolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, ifosfamide, trofosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, lapachol, beta.-lapachone, podophyllotoxin, betulin, podophyllic acid 2-ethylhydrazide, molgramostim (rhuGM-CSF), peginterferon a-2b, lenograstim (r-HuG-CSF), filgrastim, macrogol, dacarbazine, basiliximab, daclizumab, selectin (cytokine antagonist), CETP inhibitor, cadherines, cytokinin inhibitors, COX-2 inhibitor, NFkB, angiopeptin, ciprofloxacin, camptothecin, fluoroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopoletin, colchicine, NO donors such as pentaerythritol tetranitrate and syndnoeimines, S-nitrosoderivatives, tamoxifen, staurosporine, beta.-estradiol, a-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, 6-a-hydroxy-paclitaxel, baccatin, taxotere and other macrocyclic oligomers of carbon suboxide (MCS) and derivatives thereof, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, β-sitosterin, ademetionine, myrtecaine, polidocanol, non ivamide, levomenthol, benzocaine, aescin, ellipticine, D-24851 (Calbiochem), colcemid, cytochalasin A-E, indanocine, nocodazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics such as cefadroxil, cefazolin, cefaclor, cefotaxim, tobramycin, gentamycin, penicillins such as dicloxacillin, oxacillin, sulfonamides, metronidazol, antithrombotics such as argatroban, aspirin, abciximab, synthetic antithrombin, bivalirudin, coumadin, enoxaparin, desulphated and N-reacetylated heparin, tissue plasminogen activator, GpIIIb/IIIa platelet membrane receptor, factor Xa inhibitor antibody, heparin, hirudin, r-hirudin, PPACK, protamin, prourokinase, streptokinase, warfarin, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thiol protease inhibitors, prostacyclin, vapiprost, interferon a, .beta and y, histamine antagonists, serotonin blockers, apoptosis inhibitors, apoptosis regulators such as p65 NF-kB or Bcl-xL antisense oligonucleotides, halofuginone, nifedipine, tranilast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainamide, retinoic acid, quinidine, disopyramide, flecamide, propafenone, sotalol, amidorone, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprozoal agents such as chloroquine, mefloquine, quinine, moreover natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-a-senecioyloxychaparrin, taxamairin A and B, regenilol, triptolide, moreover cymarin, apocymarin, aristolochic acid, anopterin, hydroxyanopterin, anemonin, protoanemonin, berberine, cheliburin chloride, cictoxin, sinococuline, bombrestatin A and B, cudraisoflavonei A, curcumin, dihydronitidine, nitidine chloride, 12-beta-hydroxypregnadien-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, bisparthenolidine, oxoushinsunine, aristolactam-AII, bisparthenolidine, periplocoside A, ghalakinoside, ursolic acid, deoxypsorospermin, psychorubin, ricin A, sanguinarine, manwu wheat acid, methylsorbifolin, sphatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnorctin, lariciresinol, methoxylariciresinol, syringaresinol, umbelliferon, afromoson, acetylvismione B, desacetylvismione A, and vismione A and B.

A combination of drugs can also be used in embodiments of the present invention. Some of the combinations have additive effects because they have a different mechanism, such as paclitaxel and rapamycin, paclitaxel and active vitamin D, paclitaxel and lapachone, rapamycin and active vitamin D, rapamycin and lapachone. Because of the additive effects, the dose of the drug can be reduced as well. These combinations may reduce complications from using a high dose of the drug.

Adherent Layer.

The adherent layer, which is an optional layer underlying the drug coating layer, improves the adherence of the drug coating layer to the exterior surface of the medical device and protects coating integrity. If drug and additive differ in their adherence to the medical device, the adherent layer may prevent differential loss (during transit) or elution (at the target site) of drug layer components in order to maintain consistent drug-to-additive or drug-to-drug ratio in the drug layer and therapeutic delivery at the target site of intervention. Furthermore, the adherent layer may function to facilitate release of coating layer components which otherwise might adhere too strongly to the device for elution during brief contact with tissues at the target site. For example, in the case where a particular drug binds the medical device tightly, more hydrophilic components are incorporated into the adherent layer in order to decrease affinity of the drug to the device surface.

As described above, the adherent layer includes a polymer or an additive or mixtures of both. The polymers that are useful for forming the adherent layer are ones that are biocompatible and avoid irritation of body tissue. Some examples of polymers that are useful for forming the adherent layer are polymers that are biostable, such as polyurethanes, silicones, and polyesters. Other polymers that are useful for forming the adherent layer include polymers that can be dissolved and polymerized on the medical device.

Some examples of polymers that are useful in the adherent layer of embodiments of the present invention include polyolefins, polyisobutylene, ethylene-1-olefin copolymers, acrylic polymers and copolymers, polyvinyl chloride, polyvinyl methyl ether, polyvinylidene fluoride and polyvinylidene chloride, polyacrylonitrile, polyvinyl ketones, polystyrene, polyvinyl acetate, ethylene-methyl methacrylate copolymers, acrylonitrile-styrene copolymers, ABS resins, Nylon 12 and its block copolymers, polycaprolactone, polyoxymethylenes, polyethers, epoxy resins, polyurethanes, rayon-triacetate, cellulose, cellulose acetate, cellulose butyrate, cellophane, cellulose nitrate, cellulose propionate, cellulose ethers, carboxymethyl cellulose, chitins, polylactic acid, polyglycolic acid, polylactic acid-polyethylene oxide copolymers, polyethylene glycol, polypropylene glycol, polyvinyl alcohol, and mixtures and block copolymers thereof.

Since the medical device undergoes mechanical manipulation, i.e., expansion and contraction, examples of polymers that are useful in the adherent layer include elastomeric polymers, such as silicones (e.g., polysiloxanes and substituted polysiloxanes), polyurethanes, thermoplastic elastomers, ethylene vinyl acetate copolymers, polyolefin elastomers, and EPDM rubbers. Due to the elastic nature of these polymers, when these polymers are used, the coating better adheres to the surface of the medical device when the device is subjected to forces or stress.

The adherent layer may also include one or more of the additives previously described, or other components, in order to maintain the integrity and adherence of the coating layer to the device and to facilitate both adherence of drug and additive components during transit and rapid elution during deployment at the site of therapeutic intervention.

Top Layer.

In order to further protect the integrity of the drug layer, an optional top layer may be applied to prevent loss of drug during transit through tortuous anatomy to the target site or during the initial expansion of the device before the coating makes direct contact with target tissue. The top layer may release slowly in the body lumen while protecting the drug layer. The top layer will erode more slowly if it is included of more hydrophobic, high molecular weight additives. Surfactants are examples of more hydrophobic structures with long fatty chains, such as Tween 20 and polyglyceryl oleate. High molecular weight additives include polyethylene oxide, polyethylene glycol, and polyvinyl pyrrolidone. Hydrophobic drug itself can act as a top layer component. For example, paclitaxel or rapamycin are hydrophobic. They can be used in the top layer. On the other hand, the top layer cannot erode too slowly or it might actually slow the release of drug during deployment at the target site. Other additives useful in the top coat include additives that strongly interact with drug or with the coating layer, such as p-isononylphenoxypolyglycidol, PEG laurate, Tween 20, Tween 40, Tween 60, Tween 80, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-o-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-o-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid, cetotiamine, cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), and penta(propylene glycol), poly(propylene glycol) oligomers, a block copolymer of polyethylene glycol and polypropylene glycol, and derivatives and combinations thereof.

Solvents.

Solvents for preparing of the coating layer may include, as examples, any combination of one or more of the following: (a) water, (b) alkanes such as hexane, octane, cyclohexane, and heptane, (c) aromatic solvents such as benzene, toluene, and xylene, (d) alcohols such as ethanol, propanol, and isopropanol, diethylamide, ethylene glycol monoethyl ether. Trascutol, and benzyl alcohol (e) ethers such as dioxane, dimethyl ether and tetrahydrofuran, (f) esters/acetates such as ethyl acetate and isobutyl acetate. (g) ketones such as acetone, acetonitrile, diethyl ketone, and methyl ethyl ketone, and (h) mixture of water and organic solvents such as water/ethanol, water/acetone, water/methanol, water/tetrahydrofuran. A solvent in the top coating layer is, for example, methanol, ethanol, and acetone.

Organic solvents, such as short-chained alcohol, dioxane, tetrahydrofuran, dimethylformamide, acetonitrile, dimethylsulfoxide, etc., are particularly useful solvents in embodiments of the present invention because these organic solvents generally disrupt colloidal aggregates and co-solubilize all the components in the coating solution.

The therapeutic agent and additive or additives may be dispersed in, solubilized, or otherwise mixed in the solvent. The weight percent of drug and additives in the solvent may be in the range of 0.1-80% by weight, or 2-20% by weight.

Another embodiment of the invention relates to a method for preparing a medical device, particularly, for example, a balloon catheter or a stent. First, a coating solution or suspension including at least one solvent, at least one therapeutic agent, and at least one additive is prepared. In at least one embodiment, the coating solution or suspension includes only these three components. The content of the therapeutic agent in the coating solution can be from 0.5-50% by weight based on the total weight of the solution. The content of the additive in the coating solution can be from about 0.1 wt % to about 45 wt %, about 0.2 wt % to about 40 wt % by weight, about 0.3 to about 15 wt %, or about 0.1 wt % or less, or less than, equal to, or greater than about 0.2 wt %, 0.3, 0.4, 0.5, 0.6, 0.8, 1, 2, 3, 4, 5, 6, 7, 8, 9, 10, 12, 14, 16, 18, 20, 22, 24, 26, 28, 30, 35, 40, or about 45 wt % or more, based on the total weight of the solution. The amount of solvent used depends on the coating process and viscosity. It will affect the uniformity of the drug-additive coating but will be evaporated.

In other embodiments, two or more solvents, two or more therapeutic agents, and/or two or more additives may be used in the coating solution.

In other embodiments, a therapeutic agent, an additive and a polymeric material may be used in the coating solution, for example in a stent coating. In the coating, the therapeutic agent is not encapsulated in polymer particles.

Various techniques may be used for applying a coating solution to a medical device such as casting, fixed volume liquid dispensing, metering (e.g., dispense a fixed amount of coating solution based on volume onto the balloon), spinning, spraying, dipping (immersing), ink jet printing, electrostatic techniques, and combinations of these processes. During the application of the coating solution, the balloon can be at least partially inflated. The metering can be performed in any suitable way, such as by pumping liquid coating solution from a reservoir to a nozzle that is proximate the surface of the balloon (e.g., the surface of an at least partially inflated balloon). The nozzle can dispense the liquid therefrom, which can be immediately transferred to the exterior of the balloon due to its proximity to the nozzle (e.g., the nozzle can be so close to the balloon that the liquid emerging from the nozzle can contact and be transferred to the exterior of the balloon before forming a drop of liquid that leaves the nozzle). The nozzle can dispense the liquid to the exterior of the balloon such that substantially none of the liquid is lost. The balloon can be rotated around its longitudinal axis during the dispensing of the liquid from the nozzle. The nozzle can move during the dispensing, such as along the exterior of the balloon parallel to the longitudinal axis of the balloon. In some embodiments, the balloon can be rotated around its longitudinal axis during the dispensing, and the nozzle can move parallel to the longitudinal axis of the balloon, such that substantially all of the balloon surface is coated with the coating solution (e.g., similar to the movement of a woodworker's chisel on a cylindrical piece of spinning wood in a lathe).

Choosing an application technique principally depends on the viscosity and surface tension of the solution. In some embodiments of the present invention, metering can be utilized because it makes it easier to control the uniformity of the thickness of the coating layer as well as the concentration of the therapeutic agent applied to the medical device.

In one embodiment of the present invention, the balloon is inflated or partially inflated, the coating solution is applied to the inflated balloon by metering it on while the balloon is inflated and rotating along its longitudinal axis. The balloon is then allowed to dry before being deflated, folded, and sheathed.

It should be understood that this description of an embodiment of an application device, fixture, and metering technique is an example. Any suitable metering or other technique may be used for coating the medical device, particularly for coating the balloon of a balloon catheter or stent delivery system or stent.

After the medical device is coated with the coating solution, the coated balloon is subjected to a drying in which the solvent in the coating solution is evaporated. This produces a coating matrix on the balloon containing the therapeutic agent. One example of a drying technique is placing a coated balloon into an oven at approximately 20° C., or higher for approximately 24 hours. Any other suitable method of drying the coating solution may be used. The time, temperature, and relative humidity may vary with particular additives and therapeutic agents.

Optional Post Treatment.

After depositing the drug-additive containing layer on the device of certain embodiments of the present invention, dimethyl sulfoxide (DMSO) or other solvent may be applied, by dip or spray or other method, to the finished surface of the coating. DMSO readily dissolves drugs and easily penetrates membranes and may enhance tissue absorption.

It is contemplated that the medical devices of embodiments of the present invention have applicability for treating blockages and occlusions of any suitable body lumen, including, among others, the gastrointestinal tract, including the esophagus, stomach, small intestine, and colon, the pulmonary airways, including the trachea, bronchi, bronchioles, the sinus, the biliary tract, the urinary tract, urethra, ureters, and prostatic urethra and other lumens. They are especially suited for treating tissue of the urological tract with, for example, a balloon catheter or a stent.

Yet another embodiment of the present invention relates to a method of treating a prostate. The method includes inserting a medical device including a coating into a prostate. The coating layer includes a therapeutic agent and an additive. In this embodiment, the medical device can be configured as having at least an expandable portion. Some examples of such devices include balloon catheters, perfusion balloon catheters, an infusion catheter such as distal perforated drug infusion catheters, a perforated balloon, spaced double balloon, porous balloon, and weeping balloon, cutting balloon catheters, scoring balloon catheters, self-expanded and balloon expanded-stents, guide catheters, guide wires, embolic protection devices, and various imaging devices.

As mentioned above, one example of a medical device that is particularly useful in the present invention is a coated balloon catheter. A balloon catheter typically has a long, narrow, hollow tube tabbed with a miniature, deflated balloon. In embodiments of the present invention, the balloon is coated with a drug solution. Then, the balloon is maneuvered through the stricture in the nonvascular body lumen to the site of a blockage, occlusion, or other tissue requiring a therapeutic agent. Once in the proper position, the balloon is inflated and contacts the walls of the stricture in the nonvascular body lumen and/or a blockage or occlusion. It is an object of embodiments of the present invention to rapidly deliver drug to and facilitate absorption by target tissue. It is advantageous to efficiently deliver drug to tissue in as brief a period of time as possible while the device is deployed at the target site. The therapeutic agent is released into such tissue, for example the lumen walls, in about 0.1 to 30 minutes, for example, or about 0.1 to 10 minutes, or about 0.2 to 2 minutes, or about 0.1 to 1 minutes, of balloon inflation time pressing the drug coating into contact with diseased nonvascular tissue.

Given that a therapeutically effective amount of the drug can be delivered by embodiments of the present invention into, for example, the prostate, in some cases the need for a stent may be eliminated, obviating the complications of fracture and dripping associated therewith.

Further, the balloon catheter may be used to treat non-vascular tissue/disease alone or in combination with other methods for treating the non vasculature, for example, direct vision internal urethrotomy (DVIU) for strictures and transurethral resection of the prostate (TURP) for BPH. DVIU is a procedure used to open a urethral stricture. Specifically, DVIU is a procedure in which relaxing incisions are made in a stricture to create urethral luminal gain. DVIU may be accomplished using cold knife (urethrotome) or a hot knife (electrode). The cutter is inserted into the body and advanced through the urethra to the area of narrowing. After the relaxing insisions have been made, balloon dilation using the coated balloon of embodiments of the present invention may be performed. In addition, stenting may be performed thereafter, or simultaneous with expansion of the coated balloon as described above. For TURP the medical device typically used is a hot knife (electrode) or a laser. In either case the device is inserted into the body and advanced through the urethra to the area of narrowing. After the prostatic tissue has been excised, balloon dilation using the coated balloon of embodiments of the present invention may be performed. In addition, stenting may be performed thereafter, or simultaneous with expansion of the coated balloon as described above.

In some of the embodiments of drug-containing coatings and layers according to the present invention, the coating or layer does not include polymers, oils, or lipids. And, furthermore, in various embodiments, the therapeutic agent is not encapsulated in polymer particles, micelles, or liposomes. As described above, such formulations can have significant disadvantages and can inhibit the intended efficient, rapid release and tissue penetration of the agent, especially in the environment of diseased tissue of the nonvasculature.

Although various embodiments are specifically illustrated and described herein, it will be appreciated that modifications and variations of the present invention are covered by the above teachings and are within the purview of the appended claims without departing from the spirit and intended scope of the invention.

Other than the operating examples, or where otherwise indicated, all numbers expressing quantities of components in a layer, reaction conditions, and so forth used in the specification and claims are to be understood as being modified in all instances by the term "about." Accordingly, unless otherwise indicated to the contrary, the numerical parameters set forth in this specification and attached claims are approximations that may vary depending upon the desired properties sought to be obtained by the present disclosure.

Preparation.

The medical device and the coating layers of embodiments of the present invention can be made according to various methods. For example, the coating solution can be prepared by dispersing, dissolving, diffusing, or otherwise mixing all the ingredients, such as a therapeutic agent, an additive, and a solvent, simultaneously together. Also, the coating solution can be prepared by sequentially adding each component based on solubility or any other parameters. For example, the coating solution can be prepared by first adding the therapeutic agent to the solvent and then adding the additive. Alternatively, the additive can be added to the solvent first and then the therapeutic agent can be later added. If the solvent used does not sufficiently dissolve the drug, it is useful to first add the additive to the solvent, then the drug, since the additive will increase drug solubility in the solvent.

EXAMPLES

The following examples include embodiments of medical devices and coating layers within the scope of the present invention. The examples should not be interpreted as limitations upon the present invention.

Example 1. Preparation of Coating Solutions

Formulation 1: 50-150 mg (0.06-0.18 mmole) paclitaxel, 25-300 mg PEG8 caprylic/capric glycerides, and 2-6 ml ethanol were mixed.

Formulation 2: 50-150 mg (0.06-0.18 mmole) paclitaxel, 25-300 mg PEG8 caprylic/capric glycerides, 25-300 mg uracil and 2-6 ml ethanol were mixed.

Formulation 3: 50-150 mg (0.06-0.18 mmole) paclitaxel, 25-300 mg PEG8 caprylic/capric glycerides, 25-300 mg uridine and 2-6 ml ethanol were mixed.

Formulation 4: 50-150 mg (0.06-0.18 mmole) paclitaxel, 25-300 mg PEG8 caprylic/capric glycerides, 25-300 mg sucralose and 2-6 ml ethanol were mixed.

Formulation 4a: 50-150 mg (0.06-0.18 mmole) paclitaxel, 25-300 mg PEG8 caprylic/capric glycerides, 25-300 mg sucralose and 2-6 ml ethanol were mixed, with a mass ratio of paclitaxel:PEG8 caprylic/capric glycerides:sucralose of 1:1:1.

Formulation 4b: 50-150 mg (0.06-0.18 mmole) paclitaxel, 25-300 mg PEG8 caprylic/capric glycerides, 25-300 mg sucralose and 2-6 ml ethanol were mixed, with a mass ratio of paclitaxel:PEG8 caprylic/capric glycerides:sucralose of 1:1:2.

Formulation 5: 50-150 mg (0.06-0.18 mmole) paclitaxel, 25-300 mg PEG8 caprylic/capric glycerides, 25-300 mg creatinine and 2-6 ml ethanol were mixed.

Formulation 6: 50-150 mg (0.06-0.18 mmole) paclitaxel, 25-300 mg PEG6 caprylic/capric glycerides, 25-300 mg uracil and 2-6 ml ethanol were mixed.

Formulation 7: 50-150 mg (0.06-0.18 mmole) paclitaxel, 25-300 mg C6-ceramide and 2-6 ml ethanol were mixed.

Formulation 8: 50-150 mg (0.06-0.18 mmole) paclitaxel, 25-300 mg monolaurin, 25-300 mg sucralose and 2-6 ml ethanol were mixed.

Formulation 9: 50-150 mg (0.06-0.18 mmole) paclitaxel, 25-300 mg sucralose and 2-6 ml ethanol were mixed.

Formulation 10: 50-150 mg (0.06-0.18 mmole) paclitaxel, 25-300 mg PEG8 mono caprylate/caprate and 1-6 ml ethanol were mixed.

Formulation 11: 50-150 mg (0.06-0.18 mmole) paclitaxel, 25-300 mg PEG8 mono caprylate/caprate, 25-300 mg sucralose and 1-6 ml ethanol were mixed.

Formulation 12: 50-150 mg (0.06-0.18 mmole) paclitaxel, 25-300 mg thymidine, and 1-6 ml (96/4 v/v) THF/water were mixed.

Formulation 13: 50-150 mg (0.06-0.18 mmole) paclitaxel, 25-300 mg uridine, and 1-6 ml (96/4 v/v) THF/water were mixed.

Formulation 14: 50-150 mg (0.06-0.18 mmole) paclitaxel, 25-300 mg caffeine, and 1-6 ml (96/4 v/v) THF/water were mixed.

Formulation 15: 50-150 mg (0.06-0.18 mmole) paclitaxel, 25-300 mg 18Crown6, and 1-6 ml ethanol were mixed.

Formulation 16: 50-150 mg (0.06-0.18 mmole) paclitaxel, 25-300 mg 18Crown6, and 1-6 ml ethanol were mixed.

Formulation 17: 50-150 mg (0.06-0.18 mmole) paclitaxel, 10-100 mg 18Crown6, 10-100 mg pentaerythritol ethoxylate (15/4) and 1-6 ml ethanol were mixed.

Formulation 18: 50-150 mg (0.06-0.18 mmole) paclitaxel, 25-300 mg pentaerythritol ethoxylate (15/4), and 1-6 ml ethanol were mixed.

Formulation 19: 50-150 mg (0.06-0.18 mmole) paclitaxel, 25-300 mg trimethylpropane ethoxylate(Mw-1014)), and 1-6 ml ethanol were mixed.

Formulation 20: 50-150 mg (0.06-0.18 mmole) paclitaxel, 25-300 mg pentaerythritol ethoxylate (3/4), and 1-6 ml ethanol were mixed.

Formulation 21: 50-150 mg (0.06-0.18 mmole) paclitaxel, 25-300 mg 15Crown5, and 1-6 ml ethanol were mixed.

Formulation 22: 25-100 mg (0.03-0.12 mmole) paclitaxel, 25-300 mg thymidine, and 1-6 ml (90/10 v/v) THF/water were mixed.

Formulation 23: 50-150 mg (0.06-0.18 mmole) paclitaxel, 5-75 mg pentaerythritol ethoxylate (15/4), 10-200 mg pentaerythritol ethoxylate (3/4), and 1-6 ml ethanol were mixed.

Formulation 24: 50-150 mg (0.06-0.18 mmole) paclitaxel, 25-300 mg trimethylpropane ethoxylate (Mw-170)), and 1-6 ml ethanol were mixed.

Example 2. Preclinical Study 1 & 2 Sample Preparation

Twenty one balloon catheters (twelve 4 mm in diameter and 40 mm in length, six 8 mm in diameter and 40 mm in length, three 20 mm in diameter and 50 mm in length) were inflated to 1 to 2 atmospheres pressure and wiped with an ethanol wipe to clean the balloon surface. Next the balloons were coated using various formulations (1-6) from Example 1 with sufficient coating solution to achieve 2-4 microgram paclitaxel per square mm of balloon surface. The balloons were then dried, folded, sheathed, packaged in a Tyvek pouch and ethylene oxide sterilized in preparation for animal testing.

Example 3. Preclinical Study 1 & 2 Treatments

For this study male dogs were used. Baseline urethrograms were taken to measure the inner diameter of the urethra treatment sites before drug coated balloon treatment. Drug coated balloon catheters prepared in Example 2 were used with nonoverlapping treatments in the pelvic, bulbar, and distal urethra just proximal of the os penis. The os penis urethra was not treated. The treatment site diameters were approximately 3.5-4.5 mm. The balloon catheters were chosen such that the nominal overstretch ratio (the ratio of balloon diameter at nominal inflation pressure to urethra diameter) for the prostatic urethra balloons was approximately 4-6. For the anterior urethra, balloon catheters were chosen such that the nominal overstretch ratio was approximately 1.8-2.3. Prior to inserting the catheter approximately 5 mL of saline was used to flush the urethra. The 18-20 mm diameter balloons were inflated in the prostatic urethra and the 8 mm balloons were inflated in the anterior urethra. The 18 to 20 mm diameter balloons were inflated to 4 atmospheres at the treatment sites for 10 min to release drug and additive, then deflated and withdraw from the dogs. The 8 mm diameter balloons were inflated to 12 atmospheres at the treatment sites for 10 min to release drug and additive, then deflated and withdraw from the dogs. The inflation overstretch ratio (the ratio of inflated balloon diameter to urethra diameter) for the inflated 20 mm diameter balloons was 4.4 to 6.3. The overstretch ratio for the inflated 8 mm diameter balloons was 2.0 to 2.5. The amount of drug in the treated urethra tissues of the sacrificed animal was measured after 4 hrs and 1 day and the residual drug remaining on the balloon after use was analyzed.

Drug coated balloon catheters prepared in Example 2 were inserted into the left ureter and urethra of a female pig. The 4 mm diameter balloons were inflated to 14 atmospheres in the ureters and the 8 mm balloons were inflated to 12 atmospheres in the urethra. The balloons were inflated at the treatment sites for 10 min to release drug and additive, then deflated and withdraw from the pigs. The inflated overstretch ratio (the ratio of inflated balloon diameter to ureter diameter) for the 4 mm diameter balloons was 1 to 1.5. The overstretch ratio (the ratio of balloon diameter to urethra diameter) for the 8 mm diameter balloons was 2.0 to 2.5. The drug concentration in the urethra and prostate tissues of the sacrificed animal was measured after 4 hrs. The residual drug remaining on the balloon after use was analyzed.

Example 4. Preclinical Study 1 & 2 Tissue and Balloon Residual Drug Content

The dog tissue drug concentration from the prostatic urethra sample in Example 3, using Formulation 4a, was 0.4 µg/g at 4 hours. The dog tissue drug concentration from the prostate sample in Example 3, using Formulation 4a, was 0.367 µg/g at 4 hours. The dog tissue drug concentration from the pelvic urethra samples in Example 3, using Formulation 4b, was 11.7 µg/g at 4 hours. The dog tissue drug concentration from the bulbar urethra samples in Example 3, using Formulation 4a, was 25.2 µg/g at 4 hours. The dog tissue drug concentration from the prostatic urethra sample in Example 3, using Formulation 4a, was 0.586 µg/g at 1 day. The dog tissue drug concentration from the prostate sample in Example 3, using Formulation 4a, was 0.429 µg/g at 1 day. The dog tissue drug concentration from the pelvic urethra samples in Example 3, using Formulation 4b, was 26.6 µg/g at day 1. The dog tissue drug concentration from the distal urethra samples in Example 3, using Formulation 4a, was 2.04 µg/g at day 1. The residual balloon content as a percent of the original drug loading from the samples in Example 3, using Formulation 4a, ranged from 45-87%.

The residual balloon content as a percent of the original drug loading from the samples in Example 3, using formulation 4b, ranged from 83-85%.

At 4 hours the proximal (Formulation 4b) right ureter pig tissue drug concentration from the samples in Example 3 was 17.3 µg/g. At 4 hours the female pig urethra (Formulation 4a) drug concentration was 66.9 µg/g. The residual balloon content as a percent of the original drug loading from the samples in Example 3 ranged from 6-58%. The average residual balloon content for Formulation 4a was 52.8%. The average residual balloon content for Formulation 4b was 64.7%.

Example 5. Preclinical Study 3 Sample Preparation

Twenty-three balloon catheters (twelve 8 mm in diameter and 40 mm in length, six 10 mm in diameter and 40 mm in length, four 12 mm in diameter and 30 mm in length, and three 10 mm in diameter and 30 mm in length) were inflated to 50% of their nominal inflation pressure and wiped with an ethanol wipe to clean the balloon surface. Next the balloons were coated using various formulations (1-6) in Example 1 with sufficient coating solution to achieve 2 microgram paclitaxel per square mm of balloon surface. The balloons were then dried, folded, sheathed, packaged in a Tyvek pouch and ethylene oxide sterilized in preparation for animal testing.

Example 6. Preclinical Study 3 Treatments

For this study male dogs were used. Baseline retrograde urethrograms were taken to measure the inner diameter of the urethra treatment sites before drug coated balloon treatment. Drug coated balloon catheters prepared in Example 5 were used with nonoverlapping treatments in the prostatic, pelvic, bulbar, and distal urethra just proximal of the os penis. The os penis urethra was not treated. The treatment site diameters were approximately 2.1-8.5 mm. The balloon catheters were chosen such that the nominal overstretch ratio (the ratio of balloon diameter at nominal inflation pressure to urethra diameter) for the prostatic urethra balloons was planned to be approximately 1.7-3.4. For the anterior urethra, balloon catheters were chosen such that the nominal overstretch ratio was approximately 1.8-2.3. Prior to inserting the catheter approximately 5 mL of saline was used to flush the urethra. The 12 mm diameter balloons were inflated in the prostatic urethra and the 8 and 10 mm diameter balloons were inflated in the anterior urethra. The 12 mm diameter balloons were inflated to 9 atmospheres at the treatment sites for 10 min to release drug and additive, then deflated and withdraw from the dogs. The 8 mm diameter balloons were inflated to 10 atmospheres at the treatment sites for 10 min to release drug and additive, then deflated and withdraw from the dogs. The overstretch ratio (the ratio of balloon diameter to urethra diameter) for the 12 mm diameter balloons was 2.0 to 3.0. The overstretch ratio for the 8 and 10 mm diameter balloons was 1.3 to 4.0. The amount of drug in the treated urethra tissues of the sacrificed animal was measured after 1 and 7 days and the residual drug remaining on the balloon after use was analyzed.

Example 7. Preclinical Study 3 Tissue and Balloon Residual Drug Content

The dog tissue drug concentration from the samples in Example 6 ranged from 4-176 µg/g at 1 day and 0.003-23 µg/g at 7 days. The residual balloon content as a percent of the original drug loading from the samples in Example 6 ranged from 5-98%.

Example 8. Preclinical Study 4 Sample Preparation

One hundred eight balloon catheters (forty-two 8 mm in diameter and 20 mm in length, twenty-seven 10 mm in diameter and 40 mm in length, twenty-five 12 mm in diameter and 40 mm in length, five 8 mm in diameter and 55 mm in length, nine 12 mm in diameter and 55 mm in length) were inflated to 50% of their nominal inflation pressure and wiped with an ethanol wipe to clean the balloon surface. Next the balloons were split into two groups; one group was coated using Formulation 1 and Formulation 4 from Example 1 with sufficient coating solution to achieve 2 microgram paclitaxel per square mm of balloon surface, and the other group was coated using the same formulations from Example 1 with sufficient coating solution to achieve 4 microgram paclitaxel per square mm of balloon surface. The balloons were then dried, folded, sheathed, packaged in a Tyvek pouch and ethylene oxide sterilized in preparation for animal testing.

Example 9. Preclinical Study 4 Treatments

For this study male dogs were used. Baseline retrograde urethrograms were taken to measure the inner diameter of the urethra treatment sites before drug coated balloon treatment. Drug coated balloon catheters prepared in Example 8 were used with nonoverlapping treatments in the prostatic, pelvic, bulbar, and distal urethra just proximal of the os penis. The os penis urethra was not treated. The treatment site diameters were approximately 2.6-7.7 mm. The balloon catheters were chosen such that the nominal overstretch ratio (the ratio of balloon diameter at nominal inflation pressure to urethra diameter) for the prostatic urethra balloons was planned to be approximately 2-4. For the anterior urethra, balloon catheters were chosen such that the nominal overstretch ratio was approximately 1.8-2.3. Prior to inserting the catheter approximately 5 mL of saline was used to flush the urethra. 8 and 12 mm diameter balloons were inflated in the prostatic urethra and 8 mm diameter balloons were inflated in the anterior urethra. The prostatic urethra balloons were inflated to 6-9 atmospheres at the treatment sites for 10 min to release drug and additive, then deflated and withdraw from the dogs. The 8 mm diameter balloons were inflated to 10 atmospheres at the treatment sites for 10 min to release drug and additive, then deflated and withdraw from the dogs. The overstretch ratio (the ratio of balloon diameter to urethra diameter) for the prostatic urethra balloons was 2.0 to 5.1. The overstretch ratio for the anterior urethra balloons was 1.4 to 2.6. The urethra diameter and the amount of drug in the treated urethra tissues of the sacrificed animal was measured after 1, 7 and 28 days and the residual drug remaining on the balloon after use was analyzed. At 28 days samples were taken for histological evaluation to compare drug coated balloon tissue to plain old balloon and untreated tissue.

Example 10. Preclinical Study 4 Pharmacokinetics, Balloon Residual Drug Content, and Urethra Lumen Gain The dog tissue average drug concentration from the samples in Example 9 was 582 µg/g at 1 day, 0.347 µg/g at day 7, and 4 µg/g at day 28. The dog tissue average drug concentration from the 2 µg/g and 4 µg/g dose density Formulation 1 samples in Example 9 was 20.34 µg/g and 0.73 µg/g, respectively, at day 28. The dog tissue average drug concentration from the 2 µg/g and 4 µg/g dose density Formulation 4 samples in Example 9 was 0.01 µg/g and 1.20 µg/g, respectively, at day 28. The residual balloon content as a percent of the original drug loading from the samples in Example 9 ranged from 0-60%. The average residual balloon content as a percent of the original drug loading from the 2 µg/g and 4 µg/g dose density Formulation 1 samples was 11.5% and 2.4%, respectively. The average residual balloon content as a percent of the original drug loading from the 2 µg/g and 4 µg/g dose density Formulation 4 samples was 12.2% and 19.9%, respectively. The mean urethral gain at 28 days, treatment site urethra diameter at 28 days minus the urethral diameter at time of treatment, ranged from 1.6 mm to a lumen loss of 4.4 mm. Examination of the histology samples showed no discernable difference between the drug coated balloon treatments, plain balloon treatments, and untreated tissue.

Example 11. Preclinical Study 5 Sample Preparation

Forty balloon catheters (twenty 6 mm in diameter and 20 mm in length, twenty 8 mm in diameter and 20 mm in length) were inflated to 50% of their nominal inflation pressure and wiped with an ethanol wipe to clean the balloon surface. Next the balloons were split into two groups; one group was coated using various formulations (1-6) in Example 1 with sufficient coating solution to achieve 3.5 microgram paclitaxel per square mm of balloon surface the other group was coated using various formulations (1-6) in Example 1 with sufficient coating solution to achieve 10 microgram paclitaxel per square mm of balloon surface. The balloons were then dried, folded, sheathed, packaged in a Tyvek pouch and ethylene oxide sterilized in preparation for animal testing.

Example 12. Preclinical Study 5 Treatments

For this study female pigs were used to allow for easier access to the ureters. Before drug coated balloon treatments baseline uretergrams and urethrograms were taken to measure the inner diameters of the ureter and urethra treatment sites before treatment. The treatment site diameters were approximately 4.0-6.0 mm. The balloon catheters were chosen such that the nominal overstretch ratio (the ratio of balloon diameter at nominal inflation pressure to urethra diameter) for the ureter balloons was planned to be approximately 1.2-1.7. For the urethra, balloon catheters were chosen such that the nominal overstretch ratio was approximately 1.8-2.3. Drug coated balloon catheters prepared in Example 11 were used for nonoverlapping treatments. A controlled experiment was conducted to investigate two procedure parameters; balloon to urethra overstretch, inflation time, and one product design feature; the drug dose density. The amount of drug in the treated urethra tissues of the sacrificed animal was measured after 1 day and the residual drug remaining on the balloon after use was analyzed.

Example 13. Preclinical Study 5 Balloon Residual Drug Content and Tissue Drug Content The pig tissue average drug concentration from the samples in Example 12 was 12.5 µg/g at 1 day. The residual balloon content as a percent of the original drug loading from the samples in Example 12 ranged from 1-52%.

Example 14. Preclinical Study 6 Sample Preparation

Eighty seven balloon catheters (thirty-seven 12 mm in diameter and 20 mm in length, fifty 8 mm in diameter and 20 mm in length) were inflated to 50% of their nominal inflation pressure and wiped with an ethanol wipe to clean the balloon surface. Next the balloons were split into two groups; one group was coated using various formulations (1-6) in Example 1 with sufficient coating solution to achieve 3.5 microgram paclitaxel per square mm of balloon surface the other group was coated using various formulations (1-6) in Example 1 with sufficient coating solution to achieve 10 microgram paclitaxel per square mm of balloon surface. The balloons were then dried, folded, sheathed, packaged in a Tyvek pouch and ethylene oxide sterilized in preparation for animal testing.

Example 15. Preclinical Study 6 Treatments

For this study casted male pigs were used. Before drug coated balloon treatments baseline urethrograms were taken to measure the inner diameter of the urethra treatment sites before treatment. Drug coated balloon catheters prepared in Example 14 were used with nonoverlapping treatments. Prior to inflation 5-10 mL of saline was used to flush the urethra. A controlled experiment was conducted to investigate the effect of double inflation and drug dose density on the amount of drug in the treated urethra tissues. The tissue drug content was measured after 1 day and 28 days and the residual drug remaining on the balloon after use was analyzed. Histology samples were taken at 28 days to compare the two different drug dose density catheter groups Example 16. Preclinical Study 5 Balloon Residual Drug Content and Tissue Drug Content The pig tissue average drug concentration from the samples in Example 14 was 83 ng/g at 1 day and 2.5 ng/g at 28 days. The residual balloon content as a percent of the original drug loading from the samples in Example 14 ranged from 19-73%.

Example 17. Preclinical Study 7 Sample Preparation

Fifty seven balloon catheters (forty-three 8 mm in diameter and 20 mm in length, fourteen 20 mm in diameter and 60 mm in length) were inflated to 50% of their nominal inflation pressure and wiped with an ethanol wipe to clean the balloon surface. The balloons were coated using various formulations (1-6) in Example 1 with sufficient coating solution to achieve 3.5 microgram paclitaxel per square mm of balloon surface. The balloons were then dried, folded, sheathed, packaged in a Tyvek pouch and ethylene oxide sterilized in preparation for animal testing.

Example 18. Preclinical Study 7 Treatments

For this study male dogs were used. These treatments were conducted under direct visualization using a 2.4 mm outer diameter endoscope. The endoscope utilized constant saline irrigation to flush visual obstructions away from the field of view, thus the treatment zones were constantly being flushed at all times. The first step in the treatment was to use cutting balloons (balloon catheters that have blades running longitudinally along the length of the balloon) in the prostatic urethra, middle urethra, and distal urethra. Next, uncoated balloons were used to dilate the treatment locations where the cutting balloons were used. Then baseline urethrograms were taken to measure the inner diameter of the urethra treatment sites before drug coated balloon treatment. Finally drug coated balloon catheters prepared in Example 17 and uncoated balloon catheters (as controls) were used. The 20 mm diameter balloons were used in the prostatic urethra and the 8 mm diameter balloons were used in the anterior urethra. The prostatic urethra balloons were inflated to 4-5 atmospheres at the treatment sites for 2 min to release drug and additive, then deflated and withdraw from the dogs. The 8 mm diameter balloons were inflated to 10 atmospheres at the treatment sites for 2 min to release drug and additive, then deflated and withdraw from the dogs. The overstretch ratio (the ratio of balloon diameter to urethra diameter) for the prostatic urethra balloons was 2.9 to 9.7. The overstretch ratio for the anterior urethra balloons was 1.3 to 3.8. The tissue drug content was measured after 3 day, 7 days, and 28 days and the residual drug remaining on the balloon after use was analyzed. Histology samples were taken at 3 and 28 days to compare direct drug coated balloon treatment to cutting balloon pretreatment followed by drug coated balloon treatment.

Example 19. Preclinical Study 7 Pharmacokinetics, Balloon Residual Drug Content, Lumen Gain, and Histology The dog tissue average drug concentration from the samples in Example 18 was 100 µg/g at day 3 and 62 µg/g at day 7 and 33 µg/g at day 28. The residual balloon content as a percent of the original drug loading from the samples in Example 18 ranged from 2-50%.

Example 20. Preclinical Study 8 Sample Preparation

Thirty nine balloon catheters (8 mm in diameter and 30 mm in length) were inflated to 3 atmospheres and wiped with an ethanol wipe to clean the balloon surface. The balloons were coated using Formulations 18, 19, and 23 from Example 1 with sufficient coating solution to achieve 2.5 microgram paclitaxel per square mm of balloon surface. The balloons were then dried, folded, sheathed, packaged in a Tyvek pouch and ethylene oxide sterilized in preparation for animal testing.

Example 21. Preclinical Study 8 Treatments

For this study male dogs were used. Baseline urethrograms were taken to measure the inner diameter of the urethra treatment sites before drug coated balloon treatment. The treatment site diameters were approximately 3.5-4.5 mm. The balloon catheters were chosen such that the nominal overstretch ratio (the ratio of balloon diameter at nominal inflation pressure to urethra diameter) for the anterior urethra balloons was approximately 1.8-2.3. Drug coated balloon catheters prepared in Example 20 were used with nonoverlapping treatments in the pelvic, bulbar, and distal urethra just proximal of the os penis. The os penis urethra was not treated. Prior to inserting the catheter approximately 5 mL of saline was used to flush the urethra. The 8 mm diameter balloons were inflated to 12 atmospheres at the treatment sites for 2 min to release drug and additive, then deflated and withdraw from the dogs. The inflated overstretch ratio (the ratio of inflated balloon diameter to urethra diameter) for the anterior urethra balloons was approximately 2.0-2.5. The tissue drug content was measured after 1 day and the residual drug remaining on the balloon after use was analyzed.

Example 22. Preclinical Study 8 Tissue Drug Content and Balloon Residual Drug Content The dog tissue drug concentration from the pelvic urethra samples in Example 21 was 0.305, 1.17, 17.3, 33.4 µg/g at day 1. The dog tissue drug concentration from the bulbar urethra samples in Example 21 was 0.28, 4.31, 44.5, 57.8 µg/g at day 1. The dog tissue drug concentration from the distal urethra samples in Example 21 was 7.37, 38.9, 238, 268 µg/g at day 1. The average drug concentration from Formulations 18, 19, and 23 was 6.5, 33.6, and 137.7 µg/g, respectively, at day 1. The residual balloon content as a percent of the original drug loading from the samples in Example 21 ranged from 20.4-81.7%. The average residual balloon content as a percentage of the original drug loading from Formulations 18, 19, and 23 was 57.7%, 68.7%, and 51.9%, respectively.

Example 23. Bench-Top Drug Release Testing Sample Preparation

Forty nine balloon catheters (thirty-one 8 mm in diameter and 30 mm in length, six 10 mm in diameter and 20 mm in length, thirteen 12 mm in diameter and 20 mm in length) were inflated to 3 atmospheres and wiped with an ethanol wipe to clean the balloon surface. The balloons were coated using various formulations (1-34) in Example 1 with sufficient coating solution to achieve either 2.5 or 3.5 microgram paclitaxel per square mm of balloon surface. The balloons were then dried, folded, sheathed, packaged in a Tyvek pouch and ethylene oxide sterilized in preparation for bench testing.

Example 24. Bench-Top Drug Release Testing

A bench top drug release apparatus was developed that consisted of a 10 inch long by 2 inch diameter cylindrical vessel placed inside a temperature controlled water bath. The cylindrical vessel was filled with 0.9% saline and maintained at 37° C., for the testing. An 8 French (i.e., wherein 3 French is 1 mm) by 13 cm long introducer sheath penetrated the top of the cylindrical vessel and was used as a conduit to pass balloon catheter samples into the cylindrical vessel. The samples developed in Example 22 were individually passed into the cylindrical vessel where they soaked for 1 minute prior to being inflated to 10 atmospheres for 1 minute and then withdrawn. The remaining drug on the balloon was analyzed to determine how much drug was released. The amount of drug released during this testing ranged from 37% to 97%.

Additional Embodiments

The following exemplary embodiments are provided, the numbering of which is not to be construed as designating levels of importance:

Embodiment 1 provides a balloon catheter for delivering a therapeutic agent to a target site of a nonvascular body lumen, the balloon catheter comprising:
a coating layer overlying an exterior surface of a balloon, wherein the coating layer comprises one or more water-soluble additives, and an initial drug load of a hydrophobic therapeutic agent;
wherein
the hydrophobic therapeutic agent is selected from the group consisting of paclitaxel, paclitaxel analogues, rapamycin, rapamycin analogues, and combinations thereof,
the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galalocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof.

Embodiment 2 provides the balloon catheter of Embodiment 1, wherein the one or more water-soluble additives promote a rapid release of the hydrophobic therapeutic agent from the balloon, and whereby the rapid release comprises a residual drug amount of the hydrophobic therapeutic agent remaining on the balloon after the balloon is inflated at the target site of the nonvascular body lumen for an inflation period of from about 0.1 minutes to about 10 minutes and subsequently removed from the nonvascular lumen.

Embodiment 3 provides the balloon catheter of Embodiment 2, wherein the residual drug amount is about 70% or less of the initial drug load.

Embodiment 4 provides the balloon catheter of any one of Embodiments 1-3, wherein the initial drug load is from about 1 microgram to about 20 micrograms of the hydrophobic therapeutic agent per square millimeter of the balloon.

Embodiment 5 provides the balloon catheter of any one of Embodiments 1-4, wherein the initial drug load is from about 2 to about 6 micrograms of the hydrophobic therapeutic agent per square millimeter of the balloon.

Embodiment 6 provides the balloon catheter of any one of Embodiments 1-5, wherein the nonvascular body lumen is one of esophagus, airways, sinus, trachea, colon, biliary tract, urinary tract, prostate, urethral, ureteral, and other nonvascular lumens.

Embodiment 7 provides the balloon catheter of any one of Embodiments 1-6, wherein the ratio by weight of the hydrophobic therapeutic agent in the coating layer to the total weight of the one or more water-soluble additives in the coating layer is from about 0.05 to about 20.

Embodiment 8 provides the balloon catheter of any one of Embodiments 1-7, wherein the ratio by weight of the hydrophobic therapeutic agent in the coating layer to the total weight of the one or more water-soluble additives in the coating layer is from about 2 to about 6.

Embodiment 9 provides the balloon catheter of any one of Embodiments 1-8, wherein the balloon catheter has a ratio of an inflated balloon diameter at one or more pressures equal to or greater than 3 atm (304 kPa) atm and equal to or less than 30 atm (3040 kPa) to the nonvascular body lumen diameter of about 1.01 to about 30.

Embodiment 10 provides the balloon catheter of any one of Embodiments 1-9, wherein the balloon catheter has a ratio of an inflated balloon diameter at about 6 atm (608 kPa) to the nonvascular body lumen diameter of about 1.01 to about 30.

Embodiment 11 provides the balloon catheter of any one of Embodiments 1-10, wherein the balloon catheter has a ratio of a nominal inflated balloon diameter to the undilated nonvascular body lumen diameter of about 1.01 to about 30.

Embodiment 12 provides the balloon catheter of any one of Embodiments 1-11, wherein the balloon catheter is for delivering the therapeutic agent to the target site of the nonvascular body lumen after the nonvascular body lumen has been flushed with water, saline solution, or a water solution comprising at least one water soluble additive.

Embodiment 13 provides a method for treating a stricture in a nonvascular body lumen, the method comprising:
flushing the nonvascular body lumen with water, saline solution, or a water solution comprising at least one water soluble additive;
inserting a balloon catheter to a target site in the stricture in the nonvascular body lumen having a diameter, the balloon catheter comprising a balloon and a coating layer overlying external surfaces of the balloon, wherein
the coating layer comprises one or more water-soluble additives and an initial drug load of a hydrophobic therapeutic agent,
the hydrophobic therapeutic agent is selected from the group consisting of paclitaxel, paclitaxel analogues, rapamycin, rapamycin analogues, and combinations thereof,
the water-soluble additive is chosen from N-acetylglucosamine, N-octyl-D-gluconamide, N-Nonanoyl-N-methylglycamine, N-octanoyl-N-methyl glutamine C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-Lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof;
inflating the balloon until the coating layer contacts walls of the stricture in the nonvascular body lumen at the target site for an inflation period, wherein the ratio of the inflated balloon diameter to the nonvascular body lumen diameter is about 1.01 to about 30;
deflating the balloon after the inflation period, wherein the inflation period is from about 0.1 minutes to about 10 minutes; and
withdrawing the balloon catheter from the stricture in the nonvascular body lumen.

Embodiment 14 provides the method of Embodiment 13, wherein the one or more water-soluble additives promote rapid release of the hydrophobic therapeutic agent from the balloon at the target site during an inflation period.

Embodiment 15 provides the method of any one of Embodiments 13-14, wherein the balloon has thereon a residual drug amount after the withdrawing.

Embodiment 16 provides the method of any one of Embodiments 13-15, wherein the stricture in the nonvascular body lumen is one of urethral strictures, benign prostatic hyperplasia (BPH) strictures, ureteral strictures, esophageal strictures, sinus strictures, and biliary tract strictures.

Embodiment 17 provides the method of any one of Embodiments 13-16, wherein the ratio by weight of the therapeutic agent in the coating layer to the total weight of the one or more water-soluble additives in the coating layer is from about 0.05 to about 20.

Embodiment 18 provides the method of any one of Embodiments 13-17, wherein the ratio by weight of the hydrophobic therapeutic agent in the coating layer to the total weight of the one or more water-soluble additives in the coating layer is from about 2 to about 6.

Embodiment 19 provides the method of any one of Embodiments 13-18, wherein the initial drug load is from about 1 microgram to about 20 micrograms of the hydrophobic therapeutic agent per square millimeter of the balloon.

Embodiment 20 provides the method of any one of Embodiments 13-19, wherein the initial drug load is from about 1 to about 6 micrograms of the hydrophobic therapeutic agent per square millimeter of the balloon.

Embodiment 21 provides the method of any one of Embodiments 13-20, wherein the balloon has thereon a residual drug amount of less than about 70% of the initial drug load after the withdrawing.

Embodiment 22 provides the method of any one of Embodiments 13-21, wherein the balloon catheter has a ratio of an inflated balloon diameter at one or more pressures equal to or greater than 3 atm (304 kPa) atm and equal to or less than 30 atm (3040 kPa) to the undilated nonvascular body lumen diameter of about 1.01 to about 30.

Embodiment 23 provides the method of any one of Embodiments 13-22, wherein the balloon catheter has a ratio of an inflated balloon diameter at about 6 atm (608 kPa) to the undilated nonvascular body lumen diameter of about 1.01 to about 30.

Embodiment 24 provides the balloon catheter of any one of Embodiments 13-23, wherein the balloon catheter has a ratio of a nominal inflated balloon diameter to the undilated nonvascular body lumen diameter of about 1.01 to about 30.

Embodiment 25 provides a method for treating at least one of benign prostatic hyperplasia and prostate cancer, the method comprising:
  flushing a prostate with water, saline solution, or a water solution comprising at least one water soluble additive;
  inserting a balloon catheter to a target site in the prostate, the balloon catheter comprising a balloon and a coating layer overlying external surfaces of the balloon, wherein the coating layer comprises one or more water-soluble additives and an initial drug load of a hydrophobic therapeutic agent, wherein
    the hydrophobic therapeutic agent is selected from the group consisting of paclitaxel, paclitaxel analogues, rapamycin, rapamycin analogues, and combinations thereof,
    the water-soluble additive is chosen from N-acetylglucosamine, N-octyl-D-gluconamide, N-nonanoyl-N-methylglucamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof;
  inflating the balloon until the coating layer contacts walls of the benign prostatic hyperplasia or the prostate cancer at the target site for an inflation period;
  deflating the balloon after the inflation period, wherein the inflation period is from about 0.1 minutes to about 10 minutes; and
  withdrawing the balloon catheter from the prostate.

Embodiment 26 provides the method of Embodiment 25, wherein the one or more water-soluble additives promote rapid release of the hydrophobic therapeutic agent from the balloon at the target site during an inflation period.

Embodiment 27 provides the method of any one of Embodiments 25-26, wherein the balloon has thereon a residual drug amount after the withdrawing.

Embodiment 28 provides the method of any one of Embodiments 25-27, wherein the ratio by weight of the therapeutic agent in the coating layer to the total weight of the one or more water-soluble additives in the coating layer is from about 0.05 to about 20.

Embodiment 29 provides the method of any one of Embodiments 25-28, wherein the ratio by weight of the therapeutic agent in the coating layer to the total weight of the one or more water-soluble additives in the coating layer is from about 2 to about 6.

Embodiment 30 provides the method of any one of Embodiments 25-29, wherein the initial drug load is from about 1 to about 20 micrograms of the hydrophobic therapeutic agent per square millimeter of the balloon.

Embodiment 31 provides the method of any one of Embodiments 25-30, wherein the initial drug load is from about 1 to about 6 micrograms of the hydrophobic therapeutic agent per square millimeter of the balloon; and the residual drug amount is about 70% or less of the initial drug load.

Embodiment 32 provides the method of any one of Embodiments 25-31, wherein during the inflating the balloon catheter has a ratio of inflated balloon diameter to the undilated diameter of the benign prostatic hyperplasia or the prostate cancer at the target site of about 1.01 to about 30.

Embodiment 33 provides the method of any one of Embodiments 25-32, wherein the balloon catheter has a ratio of an inflated balloon diameter at one or more pressures equal to or greater than 3 atm (304 kPa) atm and equal to or less than 30 atm (3040 kPa) to the undilated diameter of the benign prostatic hyperplasia or the prostate cancer at the target site of about 1.01 to about 30.

Embodiment 34 provides the method of any one of Embodiments 25-33, wherein the balloon catheter has a ratio of an inflated balloon diameter at about 6 atm (608 kPa) to the undilated diameter of the benign prostatic hyperplasia or the prostate cancer at the target site of about 1.01 to about 30.

Embodiment 35 provides the method of any one of Embodiments 25-34, wherein the balloon catheter has a ratio of a nominal inflated balloon diameter to the undilated diameter of the benign prostatic hyperplasia or the prostate cancer at the target site of about 1.01 to about 30.

Embodiment 36 provides a method for treating a urethral stricture, the method comprising:
  flushing the urethral stricture with water, saline solution, or a water solution comprising at least one water soluble additive;

inserting a balloon catheter to a target site in the urethral stricture, the balloon catheter comprising a balloon and a coating layer overlying external surfaces of the balloon, wherein the coating layer comprises one or more water-soluble additives and an initial drug load of a hydrophobic therapeutic agent, the hydrophobic therapeutic agent is selected from the group consisting of paclitaxel, paclitaxel analogues, rapamycin, rapamycin analogues, and combinations thereof, the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof, and the ratio by weight of the hydrophobic therapeutic agent in the coating layer to the total weight of the one or more water-soluble additives in the coating layer is from about 0.05 to about 20;

inflating the balloon until the coating layer contacts walls of the urethral stricture at the target site for an inflation period;

deflating the balloon after the inflation period, wherein the inflation period is from about 0.1 minutes to about 10 minutes; and withdrawing the balloon catheter from the urethral stricture.

Embodiment 37 provides the method of Embodiment 36, wherein the one or more water-soluble additives promote rapid release of the hydrophobic therapeutic agent from the balloon at the target site during an inflation period.

Embodiment 38 provides the method of any one of Embodiments 36-37, wherein the balloon has thereon a residual drug amount of less than about 70% of the initial drug load after the withdrawing.

Embodiment 39 provides the method of any one of Embodiments 36-38, wherein the ratio by weight of the therapeutic agent in the coating layer to the total weight of the one or more water-soluble additives in the coating layer is from about 0.5 to about 8.

Embodiment 40 provides the method of any one of Embodiments 36-39, wherein the ratio by weight of the therapeutic agent in the coating layer to the total weight of the one or more water-soluble additives in the coating layer is from about 2 to about 6.

Embodiment 41 provides the method of any one of Embodiments 36-40, wherein the initial drug load is from about 1 to about 20 micrograms of the hydrophobic therapeutic agent per square millimeter of the balloon.

Embodiment 42 provides the method of any one of Embodiments 36-41, wherein the initial drug load is from about 1 to about 6 micrograms of the hydrophobic therapeutic agent per square millimeter of the balloon.

Embodiment 43 provides the method of any one of Embodiments 3642, wherein during the inflating the balloon catheter has a ratio of inflated balloon diameter to the undilated diameter of the urethral stricture at the target site of about 1.01 to about 30.

Embodiment 44 provides the method of any one of Embodiments 36-43, wherein the balloon catheter has a ratio of an inflated balloon diameter at one or more pressures equal to or greater than 3 atm (304 kPa) atm and equal to or less than 30 atm (3040 kPa) to the undilated diameter of the urethral stricture at the target site of about 1.01 to about 30.

Embodiment 45 provides the method of any one of Embodiments 3644, wherein the balloon catheter has a ratio of an inflated balloon diameter at about 6 atm (608 kPa) to the undilated diameter of the urethral stricture at the target site of about 1.01 to about 30.

Embodiment 46 provides the method of any one of Embodiments 36-45, wherein the balloon catheter has a ratio of a nominal inflated balloon diameter to the undilated diameter of the urethral stricture at the target site of about 1.01 to about 30.

Embodiment 47 provides a method for treating an esophageal stricture, the method comprising:

flushing the esophageal stricture with water, saline solution or a water solution comprising at least one water soluble additive;

inserting a balloon catheter to a target site in the esophageal stricture, the balloon catheter comprising a balloon and a coating layer overlying external surfaces of the balloon, wherein the coating layer comprises one or more water-soluble additives and an initial drug load of a hydrophobic therapeutic agent.

the hydrophobic therapeutic agent is selected from the group consisting of paclitaxel, paclitaxel analogues, rapamycin, rapamycin analogues, and combinations thereof, the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof, and the ratio by weight of the hydrophobic therapeutic agent in the coating layer to the total weight of the one or more water-soluble additives in the coating layer is from about 0.05 to about 20;

inflating the balloon until the coating layer contacts walls of the esophageal stricture at the target site for an inflation period; and deflating the balloon after the inflation period, wherein the inflation period is from about 0.1 minutes to about 10 minutes' and withdrawing the balloon catheter from the esophageal stricture.

Embodiment 48 provides the method of Embodiment 47, wherein the one or more water-soluble additives promote rapid release of the hydrophobic therapeutic agent from the balloon at the target site during an inflation period.

Embodiment 49 provides the method of any one of Embodiments 47-48, wherein the balloon has thereon a residual drug amount of less than about 70% of the initial drug load after the withdrawing.

Embodiment 50 provides the method of any one of Embodiments 47-49, wherein the ratio by weight of the therapeutic agent in the coating layer to the total weight of the one or more water-soluble additives in the coating layer is from about about 0.5 to about 8.

Embodiment 51 provides the method of any one of Embodiments 47-50, wherein the ratio by weight of the therapeutic agent in the coating layer to the total weight of the one or more water-soluble additives in the coating layer is from about 2 to about 6.

Embodiment 52 provides the method of any one of Embodiments 47-51, wherein the initial drug load is from about 1 to about 20 micrograms of the hydrophobic therapeutic agent per square millimeter of the balloon.

Embodiment 53 provides the method of any one of Embodiments 47-52, wherein the initial drug load is from about 1 to about 6 micrograms of the hydrophobic therapeutic agent per square millimeter of the balloon.

Embodiment 54 provides the method of any one of Embodiments 47-53, wherein during the inflating the balloon catheter has a ratio of inflated balloon diameter to the diameter of the esophageal structure at the target site of about 1.01 to about 30.

Embodiment 55 provides the method of any one of Embodiments 47-54, wherein the balloon catheter has a ratio of an inflated balloon diameter at one or more pressures equal to or greater than 3 atm (304 kPa) atm and equal to or less than 30 atm (3040 kPa) to the undilated diameter of the esophageal stricture at the target site of about 1.01 to about 30.

Embodiment 56 provides the method of any one of Embodiments 47-55, wherein the balloon catheter has a ratio of an inflated balloon diameter at about 6 atm (608 kPa) to the undilated diameter of the esophageal stricture at the target site of about 1.01 to about 30.

Embodiment 57 provides the method of any one of Embodiments 47-56, wherein the balloon catheter has a ratio of a nominal inflated balloon diameter to the undilated diameter of the esophageal stricture at the target site of about 1.01 to about 30.

Embodiment 58 provides the balloon catheter or method of any one or any combination of Embodiments 1-57 optionally configured such that all elements or options recited are available to use or select from.

What is claimed is:

1. A method of treating a nonvascular body lumen stricture, the method comprising:
   contacting a coating on a medical device in a body lumen with walls of the body lumen stricture, the coating comprising at least one additive and an initial drug load of a therapeutic agent comprising paclitaxel, a paclitaxel analogue, docetaxel, a docetaxel analogue, taxol, a taxol analogue, rapamycin, a rapamycin analogue, everolimus, an everolimus analogue, tacrolimus, a tacrolimus analogue, or a combination thereof, wherein the coating is flushed or soaked in a solution comprising water or saline.

2. The method of claim 1, wherein the medical device comprises a balloon catheter or a stent.

3. The method of claim 1, wherein the coating is soaked in the solution outside the body.

4. The method of claim 1, wherein the coating is soaked in the solution in the body lumen.

5. The method of claim 1, wherein the coating is flushed or soaked in the solution prior to the contacting of the coating with the walls of the body lumen stricture.

6. The method of claim 1, wherein the coating is flushed or soaked in the solution after the contacting of the coating with the walls of the body lumen stricture.

7. The method of claim 1, further comprising prior the contacting of the coating with the walls of the body lumen stricture:
   inserting an uncoated balloon catheter into the body lumen stricture;
   inflating the uncoated balloon catheter until the balloon contacts the walls of the body lumen stricture;
   deflating the uncoated balloon; and
   withdrawing the uncoated balloon from the body lumen.

8. The method of claim 1, wherein the flushing or soaking in the solution in combination with the contacting of the coating with the stricture is sufficient to release 37% to 97% of the initial drug load.

9. The method of claim 1, wherein the coating is flushed or soaked in the solution for a time of at least 1 minute.

10. The method of claim 1, wherein the body lumen stricture comprises a stricture in a urethra, a ureter, a prostatic urethra, an esophagus, a biliary tract, a stomach, a colon, an intestine, a sinus, a trachea, or an airway.

11. The method of claim 1, wherein the body lumen stricture comprises a stricture in a prostatic urethra.

12. The method of claim 1, wherein the body lumen stricture comprises a urethral stricture, a benign prostatic hyperplasia (BPH) stricture, or a ureteral stricture.

13. The method of claim 1, wherein a ratio by weight of the therapeutic agent to the total weight of the additive in the coating is from 2 to 6, and wherein the initial drug load of the therapeutic agent is from 1 microgram to 20 micrograms per square millimeter of the medical device.

14. The method of claim 1, wherein the additive in the coating comprises one or more water-soluble additives.

15. The method of claim 1, wherein the additive in the coating comprises a surfactant.

16. The method of claim 1, wherein the additive in the coating comprises a protein.

17. The method of claim 1, wherein the additive in the coating comprises pentaerythritol ethoxylate, pentaerythritol propoxylate, pentaerythritol propoxylate/ethoxylate, or combinations thereof.

18. The method of claim 1, further comprising visualizing the medical device comprising the coating in the body lumen stricture with a scope during the contacting.

19. The method of claim 1, wherein the contacting of the coating on the medical device in the body lumen with walls of the body lumen stricture comprises dilating the body lumen stricture to a desired size.

20. A method of treating benign prostatic hyperplasia (BPH), the method comprising:
   contacting a coating on a medical device in a prostatic urethra with walls of the prostatic urethra, the coating comprising at least one additive and an initial drug load of a therapeutic agent comprising paclitaxel, a paclitaxel analogue, docetaxel, a docetaxel analogue, taxol, a taxol analogue, rapamycin, a rapamycin analogue, everolimus, an everolimus analogue, tacrolimus, a tacrolimus analogue, or a combination thereof, wherein the coating is flushed or soaked in a solution comprising water or saline; and
   visualizing the medical device comprising the coating in the prostatic urethra with a scope during the contacting.

* * * * *